US009075018B2

(12) United States Patent
Geddes et al.

(10) Patent No.: US 9,075,018 B2
(45) Date of Patent: *Jul. 7, 2015

(54) MICROWAVE TRIGGER METAL-ENHANCED CHEMILUMINESCENCE (MT MEC) AND SPATIAL AND TEMPORAL CONTROL OF SAME

(75) Inventors: Chris D. Geddes, Bel-Air, MD (US); Michael Previte, Peabody, MA (US)

(73) Assignee: UNIVERSITY OF MARYLAND, BALTIMORE COUNTY, Baltimore, MD (US)

( * ) Notice: Subject to any disclaimer, the term of this patent is extended or adjusted under 35 U.S.C. 154(b) by 456 days.

This patent is subject to a terminal disclaimer.

(21) Appl. No.: 13/218,890

(22) Filed: Aug. 26, 2011

(65) Prior Publication Data

US 2013/0137167 A1 May 30, 2013

Related U.S. Application Data

(63) Continuation of application No. 12/036,402, filed on Feb. 25, 2008, now Pat. No. 8,008,067, application No. 13/218,890, which is a continuation-in-part of application No. PCT/US2007/062041, filed on Feb. 13, 2007.

(Continued)

(51) Int. Cl.
*G01N 21/01* (2006.01)
*G01N 21/76* (2006.01)
(Continued)

(52) U.S. Cl.
CPC ..... *G01N 21/763* (2013.01); *Y10T 436/143333* (2015.01); *Y10T 436/23* (2015.01);
(Continued)

(58) Field of Classification Search
CPC ............ G01N 33/553; G01N 33/5438; G01N 33/54346; G01N 33/54373; G01N 33/54313; G01N 33/54353; G01N 33/582; G01N 21/648; G01N 21/76; G01N 21/554; G01N 21/763; G01N 21/6408; G01N 21/6486; G01N 21/01; G01N 21/64; G01N 21/658; B82Y 15/00; B26F 1/31; Y10S 436/805; Y10S 436/807
USPC .................... 422/82.08, 407, 52, 68.1, 82.05; 435/287.1, 288.4, 288.7, 808; 436/525, 436/172, 518, 164, 174, 805, 809; 359/321, 359/585; 250/361 C; 977/902
See application file for complete search history.

(56) References Cited

U.S. PATENT DOCUMENTS 4,662,969 A 5/1987 Wang et al.
4,672,040 A 6/1987 Josephson
(Continued)

FOREIGN PATENT DOCUMENTS

WO 89/09408 10/1989

OTHER PUBLICATIONS

Schuck et al. Improving the mismatch between light and nanoscale objects with gold bowtie nanoantennas. Jan. 2005, Phys Rev Letters, 94: pp. 017402-1-017402-4.

(Continued)

*Primary Examiner* — Melanie Y Brown
*Assistant Examiner* — Erik B Crawford
(74) *Attorney, Agent, or Firm* — Marianne Fuierer; Moore & Van Allen, PLLC

(57) ABSTRACT

The present invention relates to a method of imaging structures and features using plasmonic emissions from metallic surfaces caused by chemiluminescence based chemical and biological reactions wherein imaging of the reactions is enhanced by the use of microwave energy and further enhanced by using metallic geometric structures for spatially and temporally controlling the biological and chemical reactions.

4 Claims, 49 Drawing Sheets

Related U.S. Application Data

(60) Provisional application No. 60/902,982, filed on Feb. 23, 2007, provisional application No. 60/773,037, filed on Feb. 13, 2006.

(51) Int. Cl.
  *G01N 33/543* (2006.01)
  *G01N 33/553* (2006.01)

(52) U.S. Cl.
  CPC ..... *Y10T 436/21* (2015.01); *Y10T 436/147777* (2015.01); *Y10T 436/201666* (2015.01); *Y10T 436/145555* (2015.01); *Y10T 436/144444* (2015.01); *G01N 21/76* (2013.01); *G01N 33/54306* (2013.01); *G01N 33/5438* (2013.01); *G01N 33/553* (2013.01)

(56) References Cited

U.S. PATENT DOCUMENTS

| | | |
|---|---|---|
| 4,735,778 A | 4/1988 | Maruyama et al. |
| 5,017,009 A | 5/1991 | Schutt et al. |
| 5,049,434 A | 9/1991 | Wasulko |
| 5,449,918 A | 9/1995 | Krull et al. |
| 5,779,976 A | 7/1998 | Leland et al. |
| 5,780,249 A | 7/1998 | Wang et al. |
| 5,866,433 A | 2/1999 | Schalkhammer et al. |
| 6,066,448 A | 5/2000 | Wohlstadter et al. |
| 6,140,045 A | 10/2000 | Wohlstadter et al. |
| 6,329,209 B1 | 12/2001 | Wagner et al. |
| 6,362,011 B1 | 3/2002 | Massey et al. |
| 7,253,452 B2 | 8/2007 | Steckel et al. |
| 7,348,182 B2 | 3/2008 | Martin et al. |
| 7,351,590 B2 | 4/2008 | Martin |
| 7,564,546 B2 | 7/2009 | Maier et al. |
| 7,718,445 B2 | 5/2010 | Martin |
| 2004/0038388 A1 | 2/2004 | Yamamoto et al. |
| 2005/0244977 A1 | 11/2005 | Drachev et al. |

OTHER PUBLICATIONS

Aslan, Kadir et al. "Microwave-Accelerated Metal-Enhanced Fluorescence: Platform Technology for Ultrafast and Ultrabright Assays," Analytical Chemistry, vol. 77, No. 24, Dec. 1, 2005, pp. 8057-8067.

Zhang, Jian et al. "First observation of surface plasmon-coupled electrochemiluminescence," Chemical Physics Letters, vol. 393, No. 4-6, Aug. 1, 2004, pp. 483-487.

MICROWAVE TRIGGER METAL-ENHANCED CHEMILUMINESCENCE (MT MEC) AND SPATIAL AND TEMPORAL CONTROL OF SAME

CROSS REFERENCE TO RELATED APPLICATIONS

The present application is a continuation application of U.S. patent application Ser. No. 12/036,402 filed on Feb. 25, 2008, now U.S. Pat. No. 8,008,067, which in turn claims priority to U.S. Provisional Patent Application No. 60/902,982 filed on Feb. 23, 2007 and PCT Application No. PCT/US2007/062041 filed on Feb. 13, 2007 which in turn claims priority to U.S. Provisional Patent Application No. 60/773,037 filed on Feb. 13, 2006, the contents of all applications are hereby incorporated by reference herein.

BACKGROUND OF THE INVENTION

1. Field of the Invention

The present invention relates to bioassays, and more particularly, to the use of metallized surfaces to enhance intensity of chemiluminescence species or reactions in assays thereby increasing sensitivity and detectability of same.

2. Background of the Related Art

The use of light-producing chemical reactions for quantitative detection in biotechnology is increasing [1-7], especially with regard to chemiluminescence based ligand-binding assays [1-7]. The attractiveness of chemiluminescence as an analytical tool lies primarily in the simplicity of detection [8]; the fact that most samples have no unwanted background luminescence, as is typically observed in fluorescence-based assays [9]; and the fact that no optical filters are required to separate the excitation wavelengths and scatter [8], as is also required for fluorescence-based detection [9].

However, chemiluminescent based detection is currently limited by the availability of chemiluminescent probes, which is not a factor governing fluorescence based detection [9]. Both fluorescence and chemiluminescence based technologies do however suffer from an inherent need for increased sensitivity/detection limits [8, 9]. For fluorescence, this is governed by the quantum yield of the tagging fluorophore, the level of unwanted background fluorescence and the photostability of the fluorophore [9], where as for chemiluminescence, detection is limited by the quantum efficiency of the chemiluminescence reaction or probe, and the time before depletion of the reactants [8]. For both detection systems, an increased luminescence yield would clearly benefit overall detectability and therefore for bioassays, the sensitivity towards a particular analyte.

Recent developments have provided new technology to enhance fluorescence and that can increase the system quantum yield [10-13], the photostability of the fluorophore [10-13] and by using spatially localized excitation can readily remove unwanted background fluorescence [14]. Specifically, techniques such as Metal-Enhanced Fluorescence (MEF) [10-20] also called Radiative Decay Engineering [21] and Surface Enhanced fluorescence (SEF) [22], have used nanosecond decay time fluorophores in close proximity to a variety of different sized [15] and shape [16,17] noble metal nanostructures to overcome the shortcomings of fluorescence technique.

However, to date no one has found any comparable systems to overcome the shortcomings of using chemiluminescent based reaction detection methods.

SUMMARY OF THE INVENTION

The present invention relates to surface plasmon-coupled chemiluminescence (SPCC), where the luminescence from chemically induced electronic excited states couple to surface plasmons in metallized particles or surfaces. Importantly, these plasmonic emissions emitted from a metallic particle or surface are generated without an external excitation source but instead from chemically induced electronically excited states.

Further, the present invention provides for a system comprising conducting geometric structures positioned on a substrate to control electromagnetic fields for spatially and temporally controlling biological and chemical reactions, wherein the biological and chemical reactions are enhanced by focusing low power microwave energy at the system.

In one aspect, the present invention relates to bioassay systems comprising metallic surfaces for the enhancement of effects of chemiluminescence based reactions positioned near the metallic surfaces, wherein metallic surface plasmons are excited by a chemically induced electronically excited state of a chemiluminescent species and radiation emitted therefrom providing an enhanced signal.

In another aspect, the present invention relates to a system for measuring a target molecule in a test sample, the method comprising:
  i) immobilizing metallic structures on a surface substrate;
  ii) positioning a capture molecule having affinity for the target molecule on the metallic structures or adjacent to the metallic structures;
  iii) contacting the capture molecule with the test sample suspected of comprising the target molecules, wherein the target molecule will bind to the capture molecule to form a complex;
  iv) contacting the complex with a detector molecule having affinity for the target molecule, wherein the detector molecule comprises a chemiluminescent label;
  v) exposing the chemiluminescent label to a trigger molecule that will chemically react with the chemiluminescent label to induce a chemical reaction that produces a chemically electronically excited state;
  vi) exposing the chemical reaction to microwave energy in an amount to enhance emissions; and
  vii) measuring the intensity of emissions.

The metallic structure may comprise a single layer of metallic material or numerous layers of materials including silver, gold, copper, zinc, aluminum, platinum or any metal exhibiting plasmonic emission. Further, the metallic structures may include layer of a dielectric material such as, silicon oxide. The metallic structures may take the form of metallic islands, nanostructures, colloids, porous matrix, metallic particles impregnated within a glass or polymeric surface and/or a metallic surface in a patterned shape. The patterned shape includes metallic containing shapes having at least one apex wherein the shape includes but is not limited to a triangle, square, rectangle, trapezoid, polygon, elliptical, oblong or combinations thereof. The surface substrate may be fabricated of a polymeric material, glass, paper, nitrocellulose, combinations thereof or any material that provides sufficient stability for placement of the metallic structures.

This embodiment can be enhanced by placement of metallic structures having a shape with an apex area and positioning such apex areas adjacent to each other and creating a reactive zone therebetween. The reactive zone therebetween is prepare for placement of the immobilized capture molecule complementary to a target molecules. Further, the apex area and reactive zone can be exposed to microwave energy in an amount to increase the reaction rate in biological and clinical assay; increases intensity of emissions from the chemiluminescence reaction in both biosensing and chemical sensing technologies; enhance electric fields by focusing electromagnetic fields in the reactive zone and/increase Brownian motion in molecules contained within the reactive zone.

The metallic structures when fabricated into geometric shapes comprising an apex area for forming a reactive zone can be positioned on assay system with multiple wells wherein the reactive zone includes the wells and exposure to microwave energy enhances the reactions therein.

In yet another aspect, the present invention relates to a bioassay for measuring concentration of receptor-ligand binding in a test sample, the method comprising:
  i) preparing metallic structures immobilized on a surface wherein the metallic structures have positioned thereon or adjacent thereto a receptor molecule having affinity for a ligand of interest;
  ii) contacting the receptor molecule with the test sample suspected of comprising the ligand of interest, wherein the ligand of interest will bind to the receptor molecule to form a receptor-ligand complex;
  iii) contacting the receptor-ligand complex with a detector molecule having affinity for the ligand to form a receptor-ligand-detector complex, wherein the detector molecule comprises a chemiluminescent label;
  iv) exposing the chemiluminescent label to a trigger solution that will chemically react with the chemiluminescent label metal complex to induce a chemically electronically excited state; and
  v) measuring the intensity of radiation.

Optionally, the metallic structures and/or area near such metallic structures is exposed to microwave energy in an amount to enhance emissions.

Preferably, the metallic surfaces take the form of metallic islands, nanostructures, colloids, porous matrix, metallic particles impregnated within a glass or polymeric surface and/or a metallic surface in a patterned shape. The patterned shape includes at least one apex wherein the shape includes but is not limited to a triangle, square, rectangle, trapezoid, polygon, elliptical, oblong or combinations thereof. The metallic element may include any metal, including silver, gold, platinum, aluminum, copper and metallic exhibiting plasmonic emissions.

In another aspect, the present invention relates to a method of metal-enhanced chemiluminescence sensing, comprising:
  i) applying a metallic material to a surface used in a detection system;
  ii) introducing a solution containing at least one biomolecule for disposing near the metallic surface, wherein the biomolecule comprises a chemiluminescent label;
  iii) triggering the chemiluminescent label to induce a chemically electronically excited state thereby generating metallic surface plasmons and optionally applying microwave energy to the detection system; and
  iv) measuring the chemiluminescence signal.

In a still further aspect, the present invention provides a method for detecting a targeted pathogen in a sample, the method comprising:
  providing a system comprising:
    a metallic surface, wherein the metallic surface is positioned near an immobilized capture nucleic acid sequence probe complementary to a known nucleic acid sequence of the target pathogen; and
    a free capture nucleic acid sequence probe complementary to the known nucleic acid sequence of the target pathogen, wherein the free capture nucleic acid sequence probe has attached thereto a chemiluminescent label;
  contacting the sample with the immobilized capture nucleic acid sequence probe,
    wherein the nucleic acid sequence of the target pathogen binds to the immobilized capture nucleic acid sequence probe;
  contacting the bound nucleic acid sequence of the target pathogen with the free capture nucleic acid sequence probe for binding therewith;
  introducing a trigger component to chemically react with the chemiluminescent label thereby creating a chemically induce electronically excited state that induces excited metallic surface plasmons; and
  measuring the chemiluminescence signal intensity, wherein the signal is enhanced relative to system that does not include metallic surfaces.

The surface plasmon-coupled chemiluminescence signal may include unpolarized, p-polarized and/or s-polarized signals.

This embodiment can be enhanced by placement of metallic structures having a shape with an apex area and positioning such apex areas adjacent to each other and creating a reactive zone therebetween. The reactive zone therebetween is prepare for placement of the immobilized capture nucleic acid sequence probe that is complementary to a known nucleic acid sequence of the target pathogen. Further, the apex area and reactive zone can be exposed to microwave energy in an amount to increase the reaction and/or increase intensity of emissions from the chemiluminescence reaction.

In another aspect, the present invention relates to a system for measuring chemiluminescence, the system comprising:
  a metallized surface positioned on a surface substrate;
  a connector molecule attached to the metallized surface or near the metallized surface for binding or capture of a desired molecule in a testing sample;
  a detector molecule having an affinity for the desired molecule, wherein the detector molecule comprises a chemiluminescence label;
  a triggering component that chemically reacts with the chemiluminescence label to generate a chemically induced electronically exited state; and
  a measuring device to measure surface plasmon coupled emissions.

Yet another aspect of the present invention relates to a system for measuring chemiluminescence, the system comprising:
  a substrate surface comprising at least an area of metallized surface;
  a capture molecule attached to the metallized surface or positioned adjacent thereto for capture of a target molecule in a testing sample;
  a detector molecule having an affinity for the target molecule, wherein the detector molecule comprises a chemiluminescence label;
  a triggering agent that chemically reacts with the chemiluminescence label to generate a chemically induced electronically exited state;
  a source of microwave energy; and
  a measuring device to measure electromagnetic emissions from the metallized surfaces.

The use of low power microwave energy directed at the assay or detection system comprising at least metallic surfaces for heating of the metallic and/or chemical components therein enhances the detection system and increases the speed of chemical reactions therein.

Thus, another aspect of the present invention relates to a method for increasing and enhancing chemiluminescence signals, the method comprising;
  i) applying at least one metallic structure to a substrate surface including but not limited to glass, plastic, paper, nitrocellulose, wherein the metallic structure is fabricated of silver, gold, aluminum, copper or combinations thereof;
  ii) introducing a solution containing at least one biomolecule for disposing near the metallic surface, wherein the biomolecule comprises a chemiluminescent label;
  iii) triggering the chemiluminescent label with a reactive compound to induce a chemically electronically excited state thereby generating metallic surface plasmons;
  iv) irradiating the system with microwave energy; and
  v) measuring the chemiluminescence signal.

In a preferred embodiment, the metallic structures are in a formed pattern, wherein an area of the formed pattern includes an apex area which is positioned near the apex of another formed pattern, thereby providing a reactive zone positioned between the two apex areas. Additional structures that include an apex area may be added and positioned adjacent to the reactive zone. The reactive zone can have a diameter or distance between the adjacent apex areas from about 0.05 mm to 5 mm. Notably the reactive zone positioned between the two apexes may be used to modify, perturb or mutate any of the physical, chemical or molecular integrity of cells, pathogen, bugs, bacteria. etc. Further the reactive zone may be used to extract DNA/RNA from both prokaryote and eukaryote organisms.

Other features and advantages of the invention will be apparent from the following detailed description, drawings and claims.

DETAILED DESCRIPTION OF THE INVENTION

Figure 1:
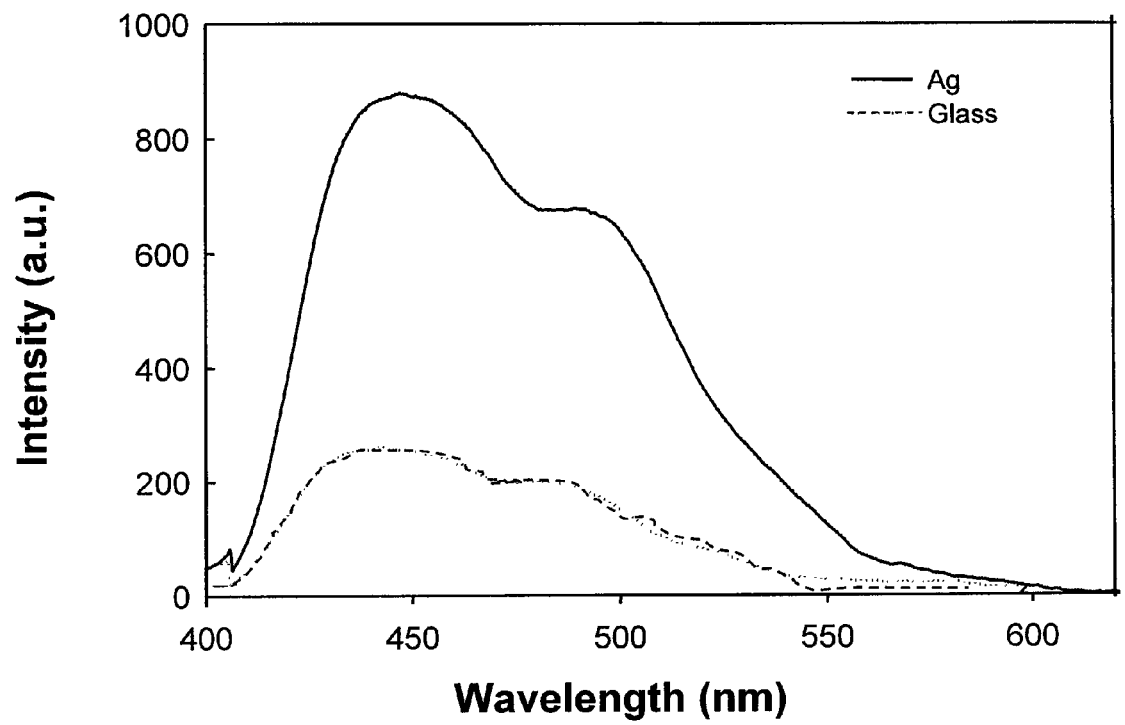
FIG. 1 shows Metal-Enhanced Chemiluminescence (MEC) on a silvered surface, Top, and photographs showing the enhanced luminescence, Bottom.
Figure 1:
Figure 1:
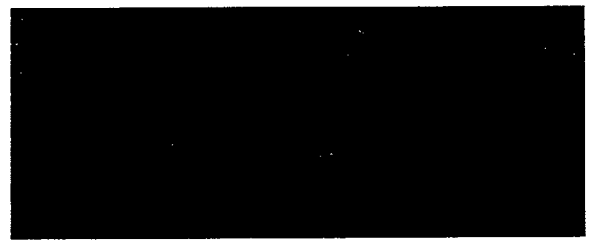

Surface plasmons are collective oscillations of free electrons at metallic surfaces. When a metallic article or surface is exposed to an electromagnetic wave, the electrons in the metal (plasmons) oscillate at the same frequency as the incident wave. Subsequently, the oscillating electrons radiate electromagnetic radiation with the same frequency as the oscillating electrons. It is this re-radiation of light at the same incident wavelength that is often referred to as plasmon emission. In the present invention chemically induced electronic excited states (chemiluminescence species) couple to surface plasmons to produce emission intensities greater than from about 5 to 1000-fold, as compared to a control sample containing no metallic surface. This approach is of significance for optically amplifying chemiluminescence based clinical assays, potentially increasing analyte/biospecies detectability.

The present invention applies microwave pulses to 'trigger' chemiluminescent reactions and create large 'on demand' photon bursts (i.e., flux) from the reaction. In addition, in the presence of silver island films, the chemiluminescence emission is not only enhanced from the plasmon effects of chemiluminescence coupled to silver surfaces, but also the reaction is further accelerated and 'triggered' by the localized heating of the metal colloids. Subsequently, the present invention provides for improvements in the fundamental detection limits of chemiluminescent reactions.

It is shown herein that the extent of microwave field enhancement for solution and surface based chemiluminescent reactions is due to "lightning rod" effects that give rise to different electric field distributions on planar aluminum geometries. Consistent with these findings, it is experimentally shown herein that it is possible to spatially and temporally control the extent of triggered chemiluminescence from solution and surface based reactions with low power microwave (Mw) pulses and maximize localized microwave field enhancements with optimized planar aluminum geometries.

Due to increased reaction rates for these triggered chemiluminescent reactions on aluminum substrates, the 'on-demand' nature of light emission provides substantial improvements in signal-to-noise ratios and a spatially localized amplified photon flux for discrete time intervals. The extent of microwave field enhancement for solution and surface based chemiluminescent reactions can be ascribed to "lightning rod" effects that give rise to different electric field distributions for microwaves incident on planar aluminum geometries. Thus, the extent of triggered chemiluminescence can be spatially and temporally control with low power microwave (Mw) pulses. Further, localized microwave triggered metal-enhanced chemiluminescence (MT-MEC) can be maximized with optimized planar aluminum geometries. As such, the sensitivity of immunoassays will be improved with significantly enhanced signal-to-noise ratios.

The term "biomolecule" means any molecule occurring in nature or a derivative of such a molecule. The biomolecule can be in active or inactive form. "Active form" means the biomolecule is in a form that can perform a biological function. "Inactive form" means the biomolecule must be processed either naturally or synthetically before the biomolecule can perform a biological function. Exemplary biomolecules include nucleic acids, aromatic carbon ring structures, NADH, FAD, amino acids, carbohydrates, steroids, flavins, proteins, DNA, RNA, oligonucleotides, peptide, nucleic acids, fatty acids, myoglobin, sugar groups such as glucose etc., vitamins, cofactors, purines, pyrimidines, formycin, lipids, phytochrome, phytofluor, peptides, lipids, antibodies and phycobiliproptein.

The term "receptor-ligand" as used herein means any naturally occurring or unnaturally occurring binding couple wherein the components have affinity for each other. For example, the binding couple may include an antibody/antigen complex, viral coat ligand/protein cell receptor or any combination of probe and binding partner. The term "receptor" refers to a chemical group, molecule, biological agent, naturally occurring or synthetic that has an affinity for a specific chemical group, molecule, virus, probe or any biological agent target in a sample. The choice of a receptor-ligand for use in the present invention will be determined by nature of the disease, condition, or infection to be assayed.

Embodiments of the present invention are applicable to chemiluminescence labels or moieties which participate in light-producing reactions in the presence of a triggering agent or cofactor. In the present application, for purposes of example and without limitation, a preferred embodiment will be discussed in terms of chemiluminescence labels and triggering agent. The label affixed to the detector molecule will be referred to as the "label" or "label agent". For purposes herein, "triggering agent or cofactor" is broadly used to describe any chemical species, other than the chemiluminescence labels which participates in a reaction and which produces a detectable response. Chemiluminescence labels and triggering agents produce a light response.

Examples of suitable chemiluminescence labels include but without limitation, peroxidase, bacterial luciferase, firefly luciferase, functionalized iron-porphyrin derivatives, luminal, isoluminol, acridinium esters, sulfonamide and others. A recent chemiluminescent label includes xanthine oxidase with hypoxanthine as substrate. The triggering agent contains perborate, an Fe-EDTA complex and luminol Choice of the particular chemiluminescence labels depends upon several factors which include the cost of preparing labeled members, the method to be used for covalent coupling to the detector molecule, and the size of the detector molecules and/or chemiluminescence label. Correspondingly, the choice of chemiluminescence triggering agent will depend upon the particular chemiluminescence label being used.

Chemiluminescent reactions have been intensely studied and are well documented in the literature [39]. For example, peroxidase is well suited for attachment to the detector molecule for use as a chemiluminescence. The triggering agent effective for inducing light emission in the first reaction would then comprise hydrogen peroxide and luminol Other triggering agents which could also be used to induce a light response in the presence of peroxidase include isobutyraldehyde and oxygen.

Procedures for labeling detector molecules, such as antibodies or antigens with peroxidase are known in the art. For example, to prepare peroxidase-labeled antibodies or antigens, peroxidase and antigens or antibodies are each reacted with N-succinimidyl 3-(2-pyridyldithio) proprionate (hereinafter SPDP) separately. SPDP-labeled peroxidase, or SPDP-labeled antigen or antibody is then reacted with dithiothreitol to produce thiol-labeled peroxidase, or thiol-labeled antigen or antibody. The thiol derivative is then allowed to couple with the SPDP-labeled antigen or antibody, or SPDP-labeled peroxidase.

Techniques for attaching antibodies or antigens to solid substrates are also well known in the art. For example, antibodies may be coupled covalently using glutaraldehyde to a silane derivative of borosilicate glass.

Although chemiluminescence detection has been successfully implemented, the sensitivity and specificity of these reactions require further improvements to facilitate early diagnosis of the prevalence of disease. In addition, most protein detection methodologies, most notably western blotting, are still not reliable methods for accurate quantification of low protein concentrations without investing in high-sensitivity detection schemes. Protein detection methodologies are also limited by antigen-antibody recognition steps that are generally kinetically very slow and require long incubation times; e.g., western blots require processing times in excess of 4 h. Thus, both the rapidity and sensitivity of small-molecule assays are still critical issues to be addressed to improve assay detection.

Thus, in one embodiment, the application of low level microwave heating of the sample may be used to speed up any biological/biochemical kinetics within the system. Notably, low level microwaves do not destroy or denature proteins, DNA, or RNA, but instead heat the sample sufficiently to provide for accelerated kinetics such as binding or hybridization. In addition, the microwaves are not scattered by the low density silver metal, which is contrary to most metal objects, such as that recognized by placing a spoon in a microwave oven.

Microwaves (about 0.3 to about 300 GHz) lie between the infrared and radio frequency electromagnetic radiations. It is widely thought that microwaves accelerate chemical and biochemical reactions by the heating effect, where the heating essentially follows the principle of microwave dielectric loss. Polar molecules absorb microwave radiation through dipole rotations and hence are heated, where as non-polar molecules do not absorb due to lower dielectric constants are thus not heated. The polar molecules align themselves with the external applied field. In the conventional microwave oven cavity employed in this work, the radiation frequency (2450 MHz) changes sign $2.45 \times 10^9$ times per second. Heating occurs due to the tortional effect as the polar molecules rotate back and forth, continually realigning with the changing field, the molecular rotations being slower than the changing electric field. The dielectric constant, the ability of a molecule to be polarized by an electric field, indicates the capacity of the medium to be microwave heated. Thus, solvents such as water, methanol and dimethyl formamide are easily heated, where as microwaves are effectively transparent to hexane, toluene and diethylether.

For metals, the attenuation of microwave radiation arises from the creation of currents resulting from charge carriers being displaced by the electric field. These conductance electrons are extremely mobile and unlike water molecules can be completely polarized in 10-18 s. In microwave cavity used in the present invention, the time required for the applied electric field to be reversed is far longer than this, in fact many orders of magnitude. If the metal particles are large, or form continuous strips, then large potential differences can result, which can produce dramatic discharges if they are large enough to break down the electric resistance of the medium separating the large metal particles.

Interestingly, and most appropriate for the new assay platform described herein, small metal particles do not generate sufficiently large potential differences for this "arcing" phenomenon to occur. However, as discuss hereinbelow, the charge carriers which are displaced by the electric field are subject to resistance in the medium in which they travel due to collisions with the lattice phonons. This leads to Ohmic heating of the metal nanoparticles in addition to the heating of any surface polar molecules. Intuitively, this leads to localized heating around the metallic nanostructures in addition to the solvent, thereby rapidly accelerating assay kinetics.

In the present invention, microwave radiation may be provided by an electromagnetic source having a frequency in a range between 0.3 and 10 GHz, more preferably from about 1 GHz and 5 GHz, and a power level in a range between about 10 mwatts and 400 watts, preferably from 30 mwatts to about 200 watts, and more preferably from about 50 watts to 300 watts. Any source, known to one skilled in the art may be used, such as a laser having the capacity to emit energy in the microwave range. The microwave radiation may be emitted continuously or intermittently (pulsed), as desired, to maintain the metallic particles at a predetermined temperature such that it is capable of increasing the speed of chemical reactions not only in the assay system but also the chemiluminescence species.

In the alternative, microwave energy can be supplied through a hollow wave guide for conveying microwave energy from a suitable magnetron. The microwave energy is preferably adjusted to cause an increase of heat within the metallic material without causing damage to any biological materials in the assay system.

In one embodiment the present invention provides for a metallic surface and a biomolecule capable of chemiluminescing, wherein the metallic surface and the biomolecule are separated by at least one film spacer layer. The thickness of said film may be chosen so as to enhance the chemiluminescence of the biomolecule by positioning the biomolecule an optimal distance from the metallic surface. The film spacer layer may be one or multiple layers of a polymer film, a layer formed from a fatty acid or a layer formed from an oxide. In a preferable embodiment, the film spacer layers and the metallic surface are chemically inert and do not bind to the biomolecules to be detected or to intermediates that are bound to the compounds to be detected, for example covalently bound. The layer formed from a fatty acid may be formed by a Langmuir-Blodgett technique. The film spacer layer may be a spin coated polymer film. The oxide layer may be formed from a deposition technique, such as vapor deposition.

Further, the metallic surface may be in the form of a porous three dimensional matrix. The three dimensional matrix may be a nano-porous three dimensional matrix. The metallic surface may include metal colloid particles and/or metal-silica composite particles. The metallic surface may comprise agglomerated metal particles and/or binary linked particles or metal particles in a polymer matrix. The three dimensional matrix may be formed from controlled pore glasses or using matrices assembled from the aggregation of silver-silica composites themselves. The matrices may be metallic nanoporous matrix, through which species will flow and be both detected and counted more efficiently. The ability to quantitatively count single flowing molecules under practical conditions may have many implications for medical diagnostics, the detection of biohazard organisms and new and quicker methods for DNA sequencing.

In yet another embodiment, a surface substate is modified by adhering metallic surfaces fabricated to form a geometric shape such as triangle, square, oblong, elliptical, rectangle, or any shape that provides at least one apex area of the metallic surface. Further multiple metallic geometric shapes may be adhered to a surface in the form of a pattern to provide at least one reactive zone positioned between the apex areas. It is envisioned that the apex area includes not only pointed regions but regions with rounded edges such as found in an oblong or elipitical shape. The apex areas are preferably arranged so that one apex area is opposite from another apex area and aligned to cause the reactive zone to be positioned therebetween. The thickness of the metallic geometric shaped forms ranges from 25 nm to about 1000 nm, and more preferably from about 45 nm to about 250 nm.

The geometric shapes can be formed on the surface substrate by any means known to those skilled in the art, including masking the surface substrate with subsequent deposition of the metallic material, fixing preformed metallic geometric shapes directly onto the substrate surface, or impregnating a geometric shaped recess in the surface substrate with a metallic material that provides for a continuous planar surface on the substrate.

In one embodiment the geometric shapes include a diversity of material including dielectric materials. For example a lay of metallic material can be deposited on a substrate surface with a layer of $SiO_2$ deposited thereon.

The emission enhancement may be observed at distances according to the type of chemiluminescence species to be detected and the type of metal. For example, emission enhancement may be observed when a chemiluminescence species is positioned about 4 nm to about 200 nm to metal surfaces. Preferable distances are about 4 nm to about 30 nm, and more preferably, 4 nm to about 20 nm to metal surfaces. At this scale, there are few phenomena that provide opportunities for new levels of sensing, manipulation, and control. In addition, devices at this scale may lead to dramatically enhanced performance, sensitivity, and reliability with dramatically decreased size, weight, and therefore cost.

Different effects are expected for mirrors, sub-wavelength or semi-transparent metal surfaces, silver island films or metal colloids. More dramatic effects are typically observed for islands and colloids as compared to continuous metallic surfaces. The silver islands have the remarkable effect of increasing the emission intensity at least 5-fold while decreasing the lifetime 100-fold.

Light from the chemiluminescence reaction generated by the random depopulation of a chemically induced electronic state of a luminophore and/or the plasmon coupled emissions from the metallic components can be detected using an optical detector, positioned above and/or below reaction sites. Various optical detectors, such as photodiode, charge-coupled device (CCD), photomultiplier tube (PMT), or photon counting detector, have different degree of sensitivity. PMT and photon counting detectors can achieve an electronic amplification factor as high as $10^6$-$10^8$. Conventional PMTs require a ˜1 kV power source, but new miniaturized detector requires only a 5 V. Most of the chemiluminescence emission wavelengths are in the visible region. A narrow-band optical filter may be used to ensure detecting luminescence wavelengths. The system may include a microactuator, detector, microprocessor, electronics, a display, and translation stage. The output of the detector may be interfaced to an analog to digital converter and a microprocessor to calculate analyte concentration.

It is known that the extinction properties ($C_E$) of metal particles can be expressed as both a combination of both absorption ($C_A$) and scattering ($C_S$) factors, when the particles are spherical and have sizes comparable to the incident wavelength of light, i.e. in the Mie limit[26].

$$C_E = C_A + C_S = k_1 \text{Im}(\alpha) + \frac{k_1^4}{6\pi}|\alpha|^2 \quad (1)$$

where $k_1 = 2\pi n_1/\lambda_0$ is the wavevector of the incident light in medium I and $\alpha$ is the polarizability of a sphere with radius r, $n_1$ is the refractive index and the incident wavelength. The term $|\alpha|^2$ is square of the modulus of $\alpha$.

$$\alpha = 4\pi r^3 (\epsilon_m - \epsilon_1)/(\epsilon_m + 2\epsilon_1) \quad (2)$$

where $\epsilon_1$ and $\epsilon_m$ are the dielectric and the complex dielectric constants of the metal respectively. The first term in equation 1 represents the cross section due to absorption, $C_A$, and the second term, the cross section due to scattering, $C_S$. Current interpretation of metal-enhanced fluorescence [23] is one underpinned by the scattering component of the metal extinction, i.e. the ability of fluorophore-coupled plasmons to radiate (plasmon scatter) [11]. Intuitively, larger particles have wavelength distinctive scattering spectra ($C_S$) as compared to their absorption spectra ($C_A$) [26], facilitating plasmon coupled emission from the larger nanoparticles.

Surprisingly, the present invention shows that chemically induced electronic excited states (chemiluminescence species) also couple to surface plasmons, producing emission intensities from about 5 to about 1000 fold, as compared to a control sample containing no surface silver nanostructures. Thus, the present invention further shows that surface plasmons can be directly excited by chemically induced electronically excited luminophores.

The present invention provides enhanced emissions using metallized nanostructures, islands of elliptical, spherical, triangular or rod-like forms. In exemplary cases, the elliptical islands have aspect ratios of 3/2, and the spherical colloids have diameters of 20-60 nm. However, the invention is not limited to any particular geometry. Using known coating techniques, the placement of metallic islands could be controlled precisely, as close as 50 nm apart.

Metal island particles may be prepared in clean beakers by reduction of metal ions using various reducing agents [10-13 and 27]. For example, sodium hydroxide is added to a rapidly stirred silver nitrate solution forming a brown precipitate. Ammonium hydroxide is added to re-dissolve the precipitate. The solution is cooled and dried quartz slides are added to the beaker, followed by glucose. After stirring for 2 minutes, the mixture is warmed to 30° C. After 10-15 minutes, the mixture turns yellow-green and becomes cloudy. A thin film of silver particles has formed on the slides as can be seen from their brown green color. The slides are rinsed with pure water prior to use.

Alternative procedures for preparing metal particles are also available [28-32]. Silver is primarily used because of the familiar color from the longer surface plasmon absorption of silver.

Colloids can be prepared as suspensions by citrate reduction metals. Preferred metals are silver and gold. The size of the colloids and their homogeneity can be determined by the extensive publications on the optical properties of metal particles available and the effects of interface chemistry on the optical property of colloids [33].

Silver island films can be formed by a chemical reduction of a silver salt on the quartz surface and that are relatively simple to fabricate. However, this approach does not provide a control of particle size, or distance of the chemiluminescent species from the metallic surface.

Metal particles can be bound to a surface by placing functional chemical groups such as cyanide (CN), amine ($NH_2$) or thiol (SH), on a glass or polymer substrate. Metal colloids are known to spontaneously bind to such surfaces with high affinity [34-35].

Positioning of the biomolecule or metal particle at a desired distance can be achieved by using a film. The film may be a polymer film, a Langmuir-Blodgett film or an oxide film. Proper distances may be achieved by using Langmuir-Blodgett films with fatty acid spacers. The fatty acids may be from natural sources, including concentrated cuts or fractionations, or synthetic alkyl carboxylic acids. Examples of the fatty acids include, but not limited to, caprylic ($C_8$), capric ($C_{10}$), lauric ($C_{12}$), myristic ($C_{14}$), palmitic ($C_{16}$), stearic ($C_{18}$), oleic ($C_{18}$), linoleic ($C_{18}$), linolenic ($C_{18}$), ricinoleic ($C_{18}$) arachidic ($C_{20}$), gadolic ($C_{20}$), behenic ($C_{22}$) and erucic ($C_{22}$). The fatty acids with even numbered carbon chain lengths are given as illustrative though the odd numbered fatty acids can also be used.

Also, metal-chemiluminescence species distances may be achieved by using polymer films. Examples of the polymer include, but not limited to, polyvinyl alcohol (PVA). Absorbance measurements and ellipsometry may be used to determine polymer film thickness. One type of polymer films is spin coated polymer films. The technology of spin coated polymer spacer films readily allows films to be coated onto a variety of surfaces, with varied thickness from >0.1 um. The coating can be performed on a spin coater, which allows uniform surface thickness by varying polymer concentration (viscosity) and spin speed. For example, Model P6700 spin coater (Specialty Coating Systems Inc.) allows uniform surface thickness by varying polymer concentration (viscosity) and spin speed.

Metallic colloids (or various other non-spherical shapes/particles) may also be incorporated into organic polymers, covalently or non-covalently, to form polymeric matrices, wherein the distance from diffusing species affords an increase in radiative decay rate and thus, an increase in quantum yield. Such polymeric matrices are ideal for sensing/flowing sensing applications of low concentration species.

Any chemiluminescent species may be used in the present invention that provides for a chemical reaction which produces the excited state responsible for the observed emission including, but not limited to the following excitation mechanisms:

R.+R'.→R–R+$h\nu$(single bond formation(radical-radical reaction))

.R.+.R.'→R=R+$h\nu$(double bond formation(radical-radical reaction))

$RO_2$→.R.+$O_2$→R+$h\nu$ $R^+$+$e^-$→R+$h\nu$(electron capture)

This embodiment of the present invention may have vast applications in clinical medicine, environmental monitoring applications, homeland security such as rapid detection of low concentration species, industrial processes, pharmaceutical industries such as monitoring species, and sensors for use in reduced atmospheres such as biohazard clean rooms and environments using space light.

EXAMPLES

1. Radiating Plasmons Generated from Chemically Induced Electronic Excited States 1.1 Materials Silver nitrate (99.9%), sodium hydroxide (99.996%), ammonium hydroxide (30%), trisodium citrate, D-glucose and premium quality APS-coated glass slides (75×25 mm) were obtained from Sigma-Aldrich (St. Loius, Mo.). The blue-glow chemiluminescence sticks used were the "Color Bright" light sticks, obtained from Omniglow (West Springfield, Mass.).

1.2 Chemiluminescence

The chemiluminescent materials used in this study were obtained from commercial light glow sticks. These glow sticks contain the necessary reacting chemicals encapsulated within a plastic tube. The plastic tube contains a phenyl oxalate ester and a fluorescent probe, where the choice of dye simply determines the color of the luminescence [9]. For the examples set forth herein, this choice is arbitrary as long as the luminophore emits in the visible spectral region, consistent with previous reports [10-13]. Inside the plastic tube lies a glass capsule containing the activating agent (hydrogen peroxide). Activation of the chemicals is accomplished with a bend, snap, and a vigorous shake of the plastic tube which breaks the glass capsule containing the peroxide and mixes the chemicals to begin the chemiluminescence reaction. The hydrogen peroxide oxidizes the phenyl oxalate ester to a peroxyacid ester and phenol. The unstable peroxyacid ester decomposes to a peroxy compound and phenol, the process chemically inducing an electronic excited state.

1.3. Formation of Silver Island Films (SiFs) on APS-Coated Glass Substrates

The silver island films were made according to previously published procedures employing the chemical reduction of silver nitrate on glass microscope slides using sodium hydroxide, ammonium hydroxide and glucose [10-13].

1.4. Chemiluminescence from SiFs and Glass

The chemiluminescence experiments were performed using a blue emission glow stick. After chemiluminescence initiation, approximately 70 µl of the glow stick fluid was placed between two APS-coated microscope glass slides, clamped together. The glass slides contained silver island films on one end and were bare glass on the other end. The bare end of the glass served as the control sample by which to compare the benefits of using the metal-enhanced chemiluminescence phenomenon. Subsequently, the enhancement ratio, the intensity from silver/intensity from glass, could be determined.

1.5. Chemiluminescence Measurements

Chemiluminescence spectra were collected using an Ocean Optics spectrometer, model SD 2000 (Dunedin, Fla.), connected to an Ocean Optics 1000 µm diameter fiber with an NA of 0.22 (Dunedin, Fla.). The fiber was positioned vertically on top of the slides containing the luminescening material. Spectra were collected with an integration time ranging from between 4 and 10 seconds. The integration time was kept constant between the control and silver island film sample measurements.

1.6. Results

Figure 4:
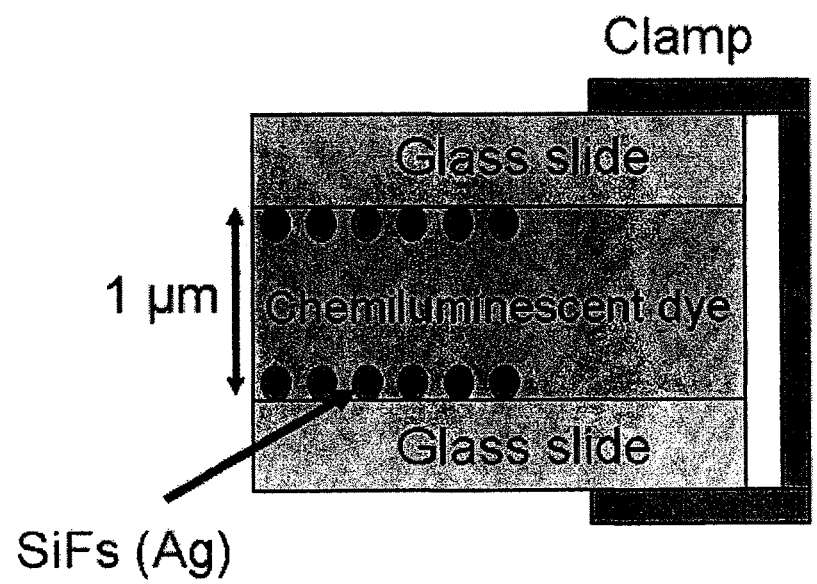
FIG. 4 shows the experimental sample set-up wherein the chemiluminescence species is placed between two glass slides comprising silver islands deposited thereon.

FIG. 1 top shows the luminescence emission spectra from between the silvered glass and glass plates. The emission from the silvered portion of the slide was spatially averaged to be about 4-5 times greater than the glass control side of the sample. In addition, the volume between both the sandwiched glass and silver slides was identical. FIG. 1—bottom shows the photographs of the slides, both before and after the addition of the chemiluminescent material. Approximately 70 µL of fluid was enough to form a thin coating across both portions of the slide, held by capillary action as the slides were sandwiched as shown in FIG. 4. The enhanced chemiluminescence is clearly visible on the silvered portion as shown in FIG. 1 (bottom). Interestingly, the digital camera was not able to capture the blue emission from the thin fluid layer of the glass region of the slide, the intensity quite weak as also shown in FIG. 1—top.

Figure 2:
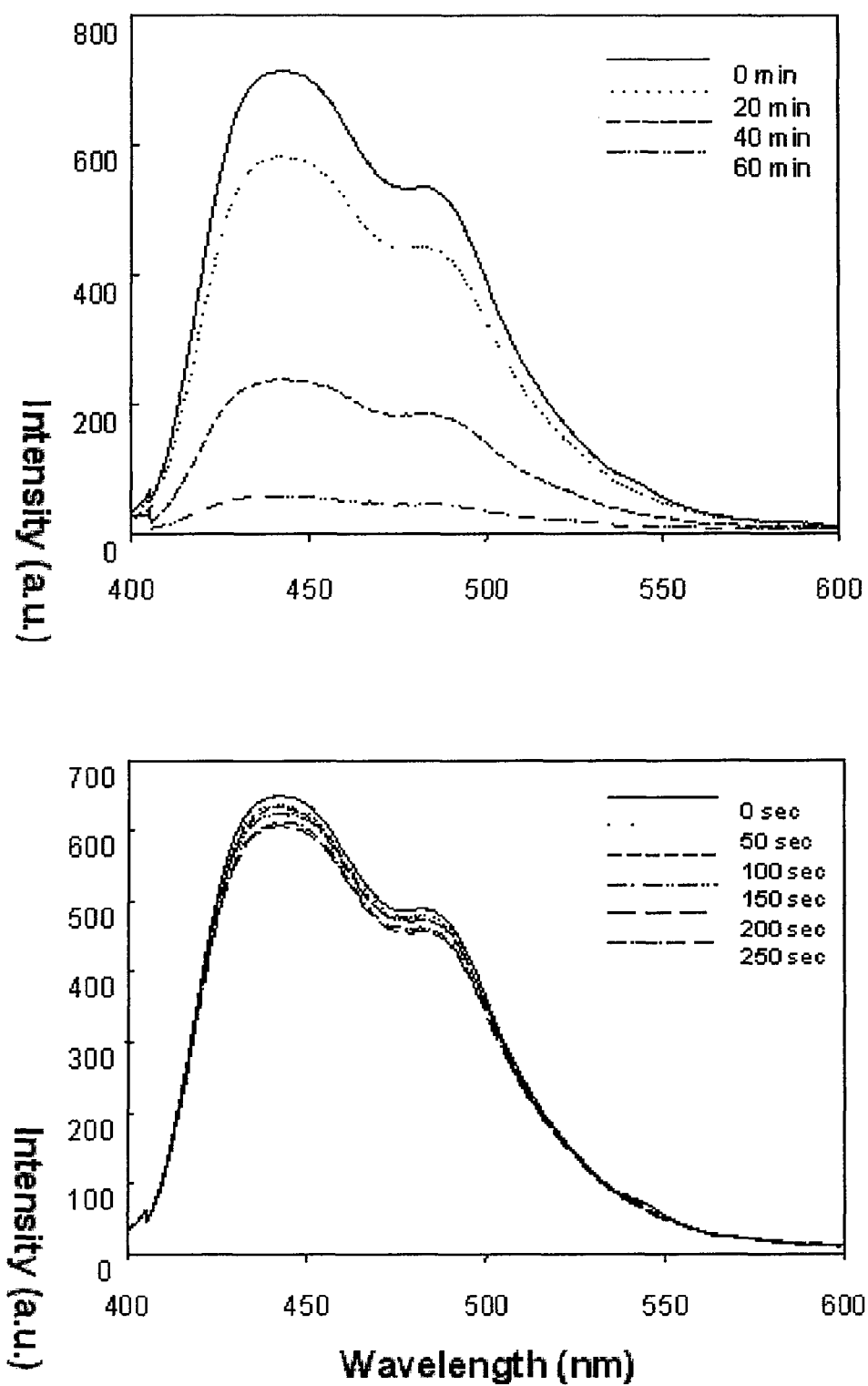
FIG. 2 shows the metal-enhanced chemiluminescence on a silvered surface as a function of time, Top, and the intensity of luminescence in terms of seconds, Bottom.

Several control experiments were performed to determine the loss of chemiluminescent intensity, due to the depletion of the reactants, FIG. 2. After a period of 60 minutes, most of the emission from the silvered plates had gone, FIG. 2-T*op*. Interestingly, the luminescence emission intensity changed very little in several tens of seconds, FIG. 2—bottom, which was the time needed to measure both the intensity on silver and glass shown in FIG. 1, making the comparison between both silver and glass a valid one. Finally, while not shown here, the rate of loss of luminescence was measured from both the silvered and glass portions of the slide. For both, the rate of chemiluminescence was almost identical, suggesting that no chemical interaction between the chemiluminescent reagents and silver occurred, the enhanced luminescence signals observed due to interactions with surface plasmons as discussed below [23].

Figure 5:
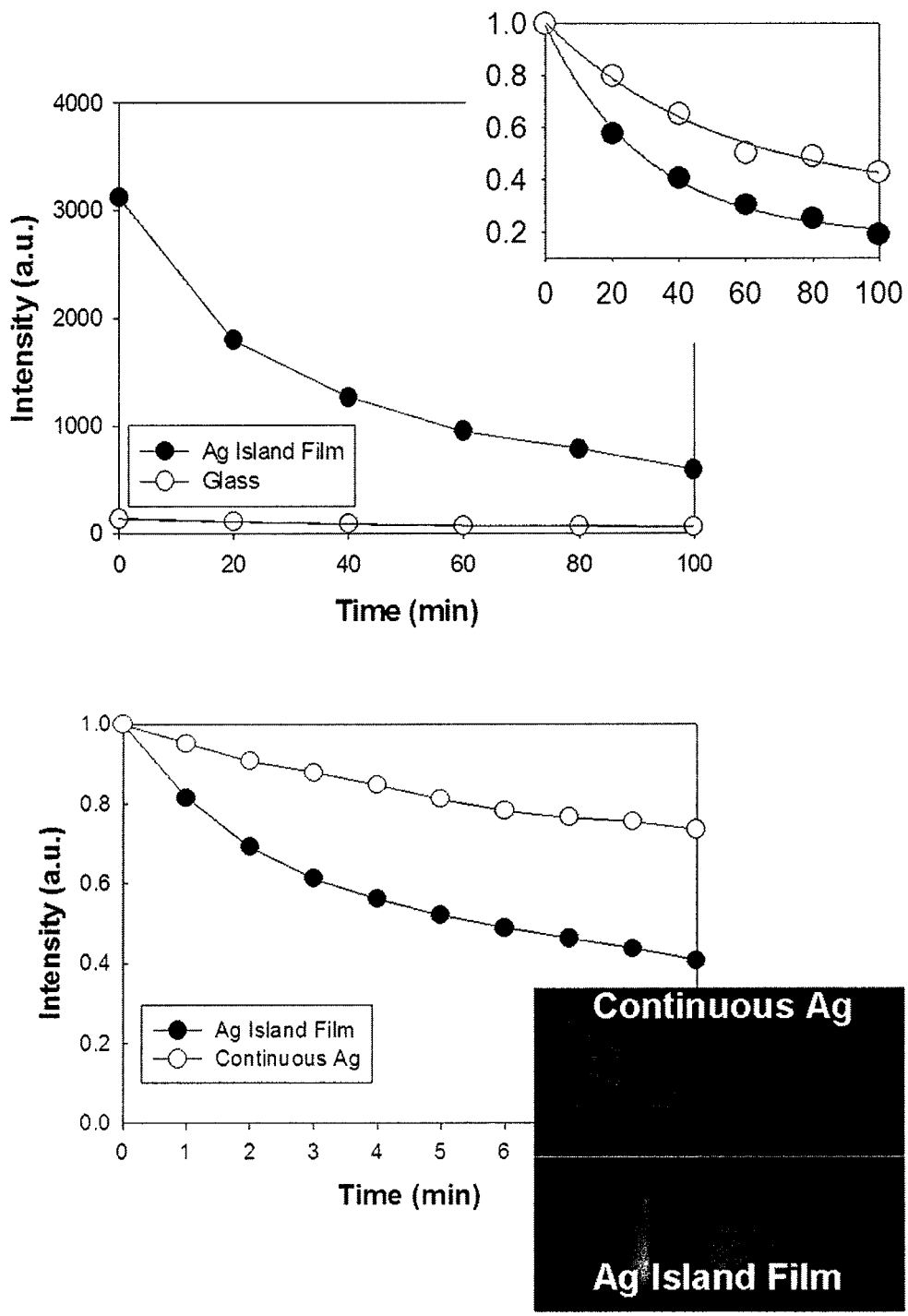
FIG. 5 shows the chemiluminescence intensity measured on both SiFs and glass as a function of time (Top) and the data normalized (Top-insert). Normalized chemiluminescence intensity on both SiFs and a continuous silver film (Bottom). Photograph of the emission from both the continuous silver film and the SiFs (Bottom—insert). Ag—Silver. SiFs—Silver Island Film.

Several detailed control experiments were undertaken to ascertain whether silver could catalyze the chemiluminescence reaction and account for the enhanced optical signatures observed, as compared to an interpretation in terms of a chemiluminescence-based radiating plasmon model. FIG. 5—top shows the luminescence intensity as a function of time. Clearly the enhanced luminescence from the SiFs is visible, with the initial intensity on silver ≈3100 a.u. (at t=0) as compared to <150 on glass. Subsequently the rates of loss of luminescence were compared after the curves were normalized, FIG. 5—top insert. The rate of loss of luminescence, which is due to the depletion of solution reactants and therefore depletion over time of excited states, was found to follow first order decay kinetics and could simply be modeled to an exponential function of the form:

$$\text{Luminescence Intensity}, I=C+B^{-kt} \quad (3)$$

where C is the intensity at time t=∞, B is a pre-exponential factor and k the rate of luminescence depletion, units $S^{-1}$. From FIG. 5—Top insert, the rate of depletion on silver was found to be 1.7 times faster than on glass, 0.034 vs 0.019 $s^{-1}$ respectively. Two explanations could initially describe this observation: Firstly, silver catalysis of the chemiluminescence reaction, or secondly, the high rate of transfer/coupling of the chemiluminescence to surface plasmons, rapidly reducing the excited state lifetime of the chemiluminescence species.

To eliminate silver based catalysis of the chemiluminescence reaction as an explanation for the enhanced signals, the luminescence rates were measured on both SiFs and a continuous silver strip. Interestingly, the rate of loss of luminescence was still found to be greater on the SiFs as compared to the continuous silver strip, FIG. 5—bottom. In addition, the emission intensity was very low indeed from the continuous strip of silver, FIG. 5—bottom insert. Given that the continuous strip is indeed darker and that the rate is slower than on SiFs, then silver based catalysis can be eliminated as a possible explanation of the observation of increased signal intensities on the SiFs. Subsequently, these observations suggest that chemically induced electronic excited states (chemiluminescence species) can readily induce/couple to surface plasmons, facilitating metal-enhanced chemiluminescence.

1.7. Discussion

Figure 3:
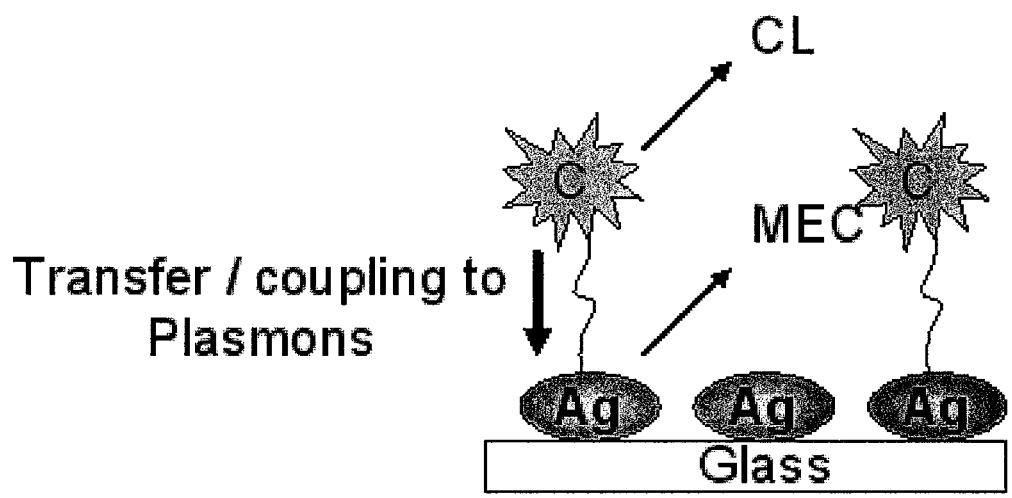
FIG. 3 shows the proposed model for Metal-Enhanced Chemiluminescence (MEC). The chemically induced electronically excited luminophore (C) transfers energy to silver plasmons (a resonance coupling interaction), which themselves radiate the photophysical properties of the excited species. CL—Chemiluminescence, MEC—Metal-Enhanced Chemiluminescence, Ag—Silver.

With the chemiluminescence species shown here, it is theorized that excited chemiluminescence species couple to surface plasmons, which is turn radiate the photophysical properties of the chemically excited state, as shown in FIG. 3. Interestingly, the chemiluminescent system described herein, wherein there is no external excitation source for direct illumination and no direct mode of excitation of the surface plasmons suggests that the surface plasmons are indeed excited from a chemically induced electronically excited state of a luminophore. It is believed that this is the first observation of the chemically induced electronic excitation of surface plasmons.

2. Directional and Polarized Emission of the Luminescence

Figure 6:
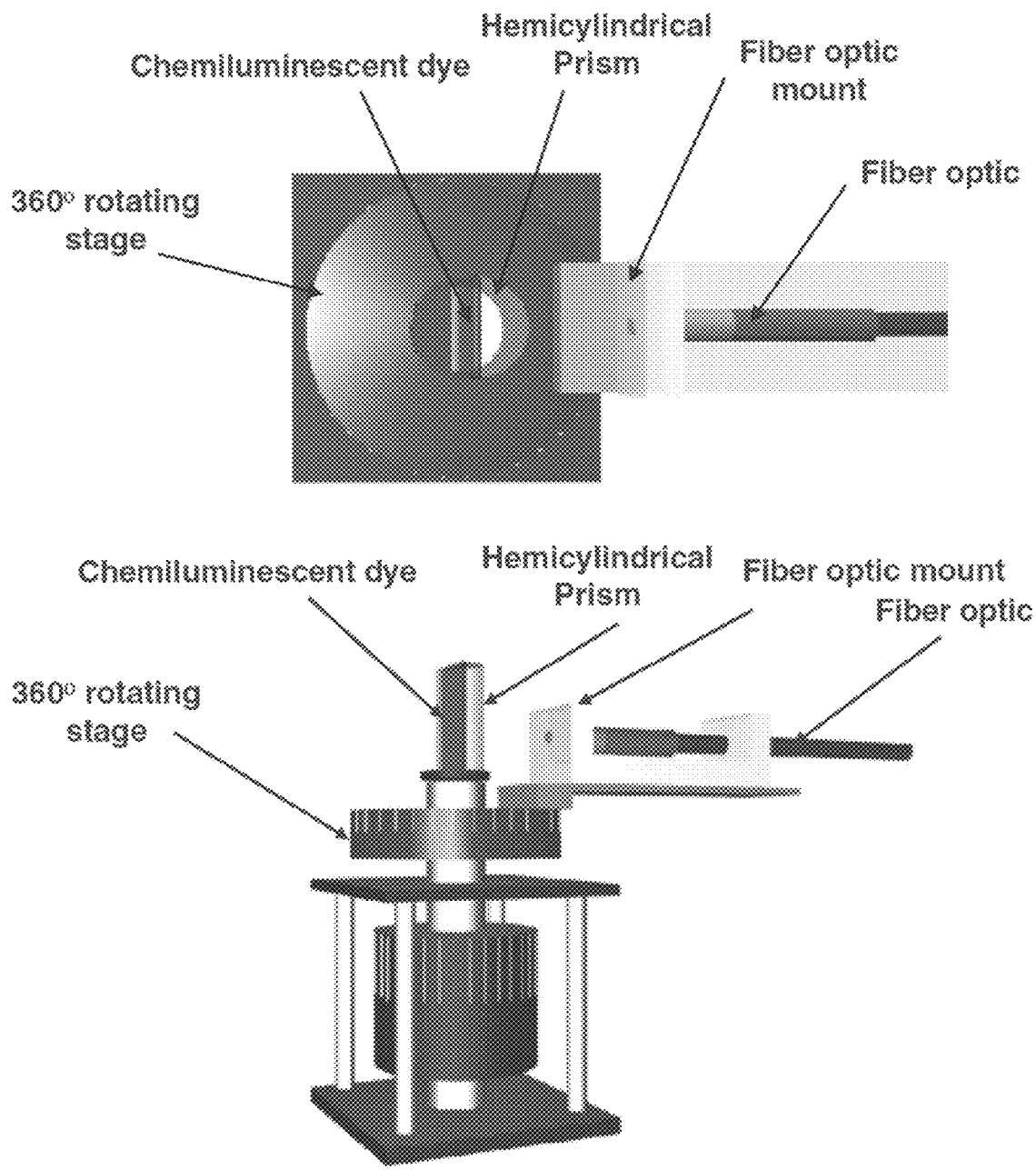
FIG. 6 shows the Experimental geometry used for measuring and/or detecting surface plasmon-coupled chemiluminescence (SPCC). Top, view from the top; bottom, side view.

The experimental geometry used for the surface plasmon-coupled chemiluminescence (SPCC) studies is shown in FIG. 6.

2.1 Materials and Methods

Premium quality APS-coated glass slides (75×25 mm), silver wire (99.99+% purity), aluminum evaporation slugs (99.999% purity), and silicon monoxide pieces (99.99% purity) were obtained from Sigma-Aldrich (St. Loius, Mo.). Gold evaporation slugs (99.999% purity) were obtained from Research and PVD Material Corporation (Wayne, N.J.). CoverWell imaging chamber gaskets with adhesive (20-mm diameter, 1-mm deep) were obtained from Molecular Probes (Eugene, Oreg.). The smaller imaging chambers were built in-house using electrical black tape, double sticky tape, and microscope coverslips. Several standard chemiluminescence kits from Omnioglow (West Springfield, Mass.) and Night Magic (Union City, Ohio) were used as the source of chemiluminescence.

2.2 Chemiluminescent Dyes

The chemiluminescent materials used in this study were obtained from commercially available kits and previously described in Example 1.

2.3 Formation of Continuous Thin Films of Metal on APS-Coated Glass Substrates

Twenty nanometers of aluminum, 45 nm of silver, and 40 nm of gold were deposited on separate APS-coated glass slides using an Edwards Auto 306 Vacuum Evaporation chamber (West Sussex, U.K.) under ultrahigh vacuum (<$3 \times 10^{-6}$ Torr). In each case, the metal deposition step was followed by the deposition of 5 nm of silica via evaporation without breaking vacuum. This step served to protect the metal surface from attack by the various chemical species present in the chemiluminescence assay.

2.4 Surface Plasmon-Coupled Chemiluminescence (SPCC) of Dyes on Continuous Metal Films The surface plasmon-coupled chemiluminescence (SPCC) experiments were performed using several different colors of the chemiluminescent dyes ranging from blue to red. They were carried out by first bending the plastic tube of the chemiluminescence kit and shaking it vigorously. This allowed the reaction mixtures to mix and begin to luminesce. The tubes were then cut with a scissor, and the reacting fluid was poured into a glass vial. Approximately 150 µL of the reacting fluid was then placed in an imaging chamber gasket with adhesive (20-mm diameter, 1-mm deep). This gasket was then pressed against an (APS-coated) continuous metal-coated and silica-capped microscope glass slide until they were stuck together creating a chamber containing the chemiluminescent dyes on the surface of the metal-coated glass slide. For smaller samples, approximately 50 µL of the reacting fluid was placed in an imaging chamber built in-house attached to an (APS-coated) continuous metal-coated and silica-capped microscope glass slide.

2.5 Surface Plasmon-Coupled Chemiluminescence (SPCC) Measurements

The metal-coated slides containing the chemiluminescent dyes were attached to a hemicylindrical prism made with BK7 glass (n=1.52), and the refractive index was matched using spectrophotometric grade glycerol (n=1.475) between the back of the glass slide (uncoated side) and the prism. This unit was then placed on a precise 360° rotatory stage which was built in-house. The rotatory stage allowed the collection of light at all angles around the sample chamber. An Ocean Optics low OH 1000 µm diameter optical fiber with NA of 0.22 (Dunedin, Fla.) used for collecting the chemiluminescence signals was mounted on a holder that was screwed onto the base of the rotatory stage. A pictorial representation of the top and side view of the setup is presented in FIG. 6. Surface plasmon-coupled chemiluminescence (SPCC) spectra were collected using a model SD 2000 Ocean Optics spectrometer (Dunedin, Fla.) connected to the above-mentioned optical fiber. The spectra were collected with an integration time between 0.5 and 2 s (depending on the intensity of the various SPCC signals). Both unpolarized and p- and s-polarized signal information was collected for the SPCC signal (from 0 to 180° with respect to the front of the prism) and for the free-space signal (from 180 to 360° with respect to the front of the prism). A separate time-dependent decay study was performed on each chemiluminescent dye to study the comparative time-dependent decay profile of the SPCC signal and the free-space signal.

2.6. Results

Figure 7:
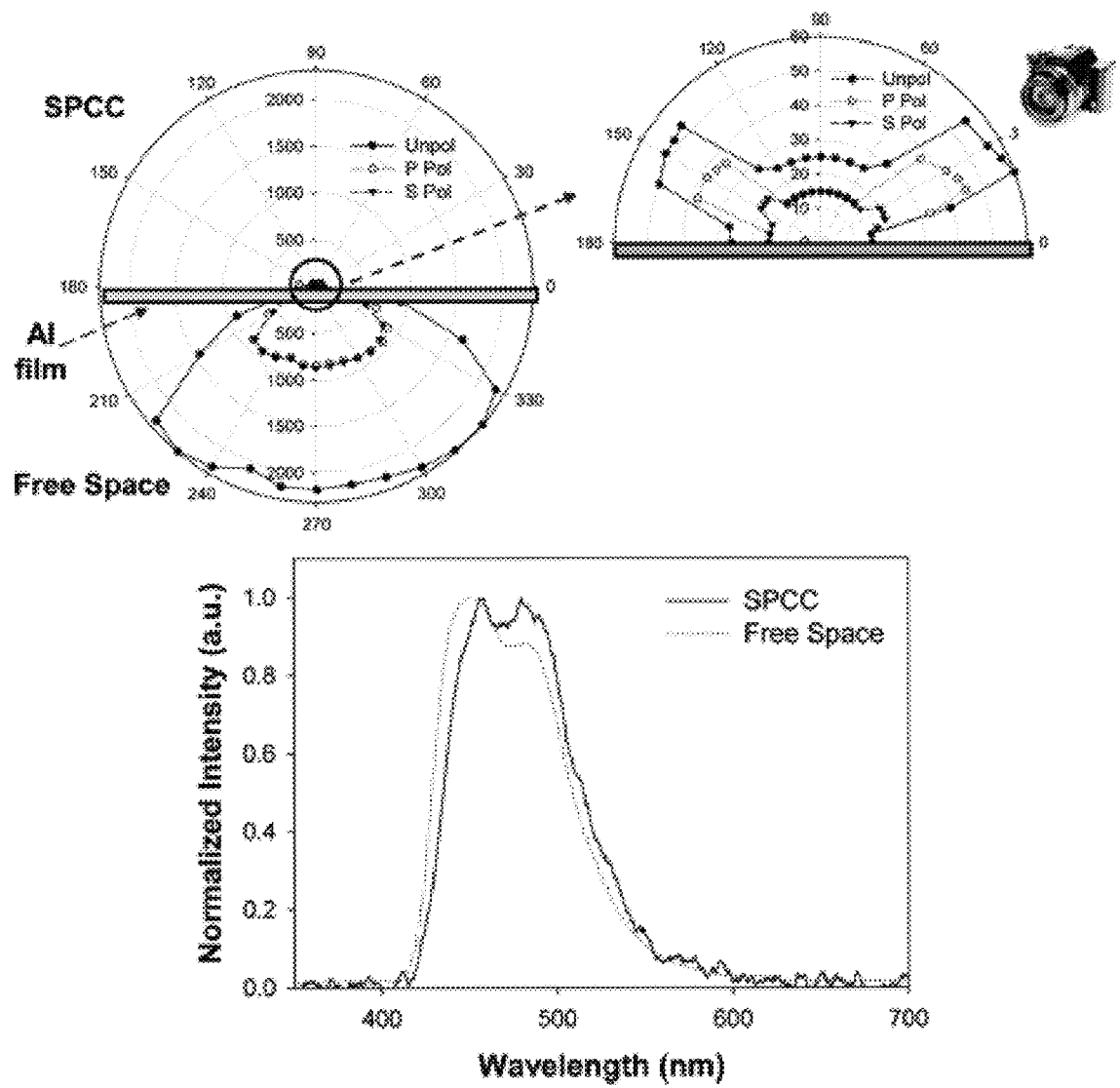
FIG. 7 shows surface plasmon-coupled chemiluminescence from 20-nm-thick aluminum films. Top right, enlarged directional SPCC; top left, free-space chemiluminescence and SPCC; bottom, emission spectra of both the free-space chemiluminescence and SPCC.

FIG. 7 (top left) shows the surface plasmon-coupled chemiluminescence (SPCC) and the free-space emission from the blue chemiluminescent dye on a 20-nm aluminum layer. It can be seen that the free-space emission is of much higher magnitude than the SPCC signal. This is because the sample chamber is 1-mm thick and only the luminophores within approximately 250 nm of the surface of silver are known to excite surface plasmons [36, 24]. Hence, the majority of the luminophores in the chamber do not couple to plasmons and so radiate their energy in the form of free-space emission. Subsequently there was an attempt to use very thin films of liquid to alleviate this effect. However, the hydrophobic nature of the surface globulated the chemiluminescence liquid, preventing films <250 nm thick to be produced.

Figure 10:
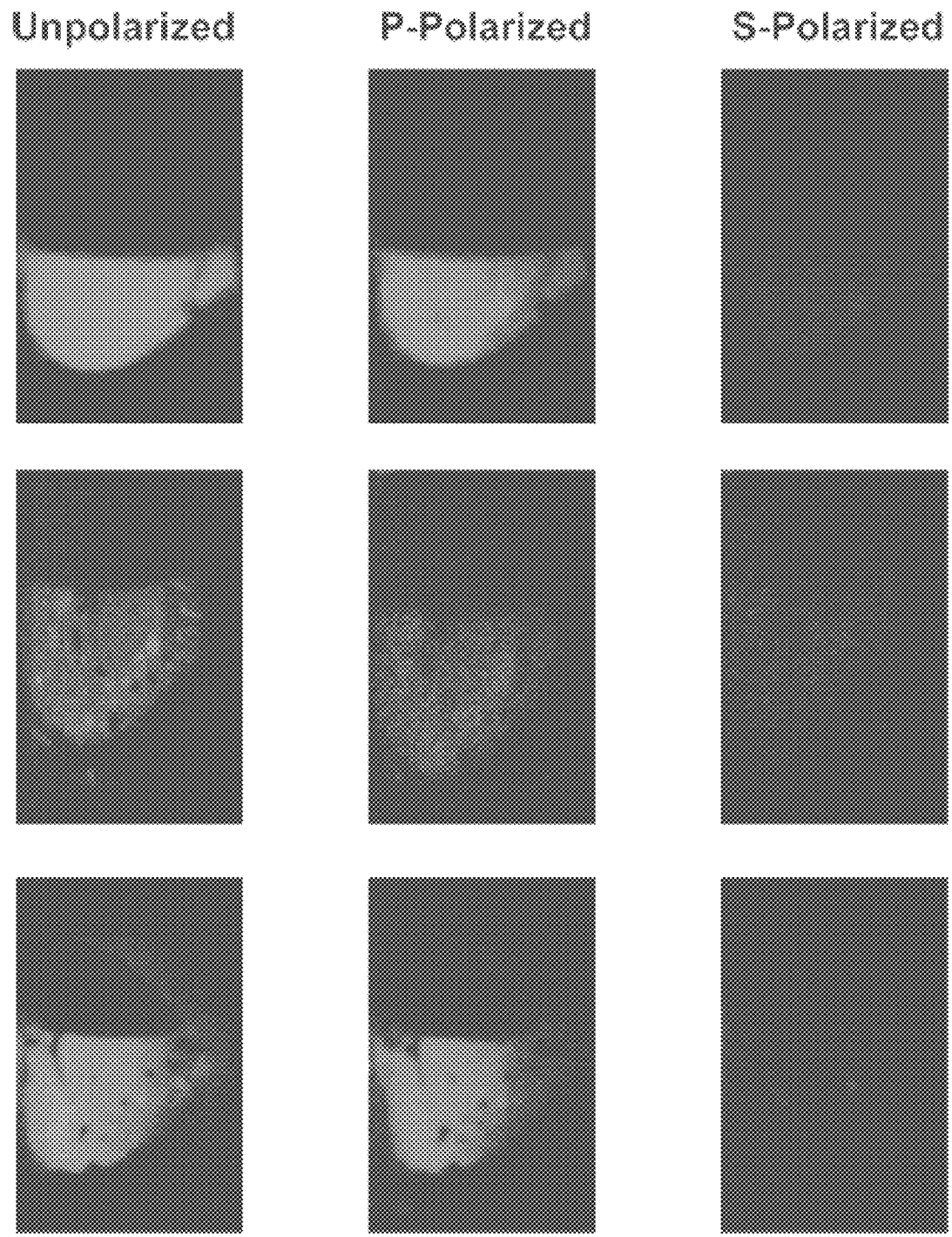
FIG. 10 shows photographs of the coupled emission at various polarizations for gold, silver, and aluminum films, top to bottom, respectively, taken at their respective SPCC peak angles. See location of camera in FIGS. 7-9 (top right).

FIG. 7 (top right) is an enlarged figure showing the highly directional and predominantly p-polarized SPCC emission only, suggesting that the observed signal is due to surface plasmons. This is in stark contrast to the free-space emission which does not show any polarization or directional preference. However, the signal at the SPCC peak angle is not entirely p-polarized. The camera located at the SPCC peak angle of the figure depicts the approximate angular position where photographs of the coupled emission at various polarizations were taken. These photographs are shown in FIG. 10. FIG. 7 (bottom) is the normalized SPCC and free-space emission spectra showing a high degree of overlap between the spectra. This suggests the plasmon-coupled chemiluminescence has not undergone any changes in its spectral properties because of the interaction between the luminescent species and the metal surface.

Figure 8:
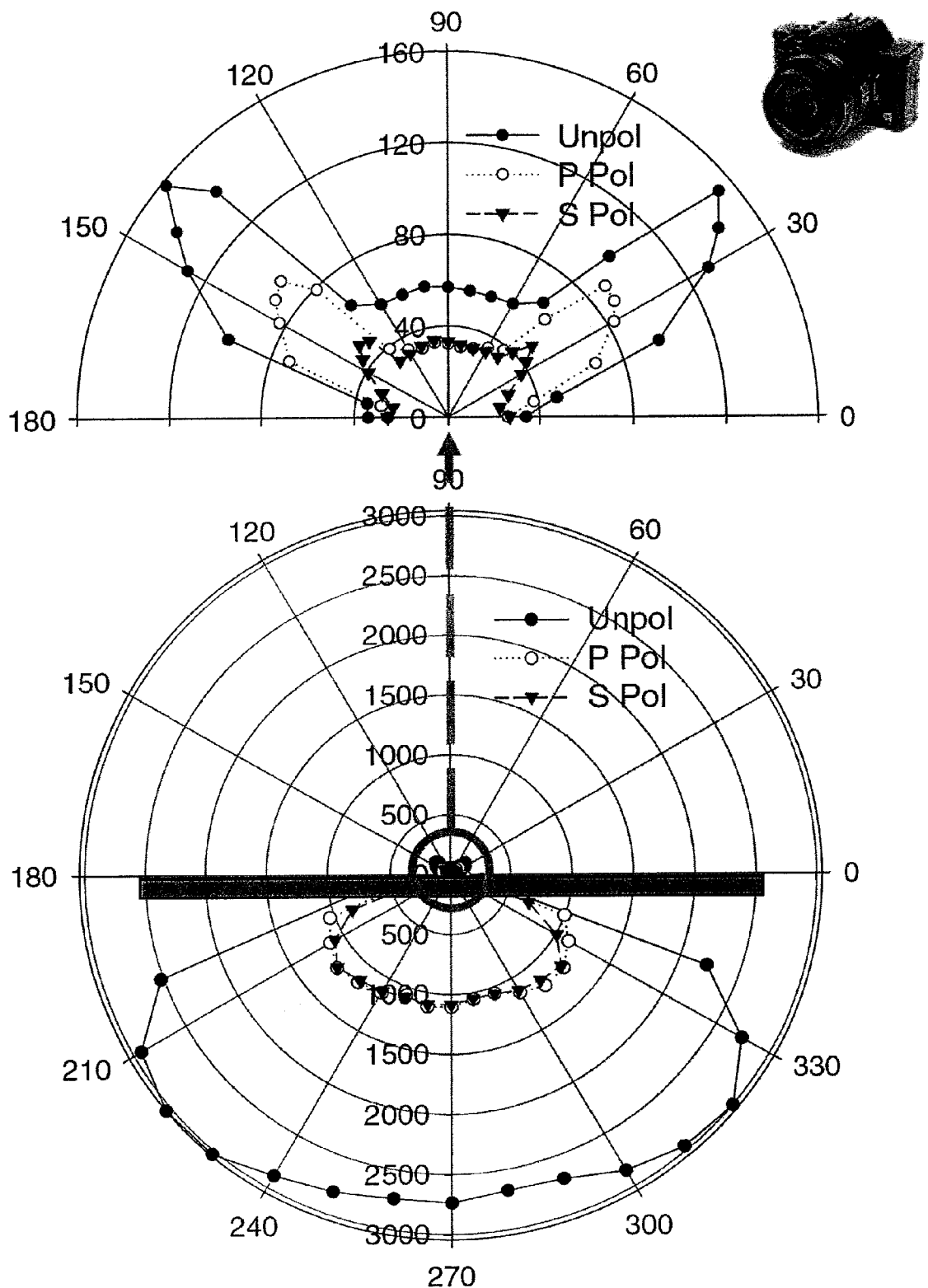
FIG. 8 shows surface plasmon-coupled chemiluminescence from 45-nm-thick silver films. Top right, enlarged directional SPCC; top left, free-space chemiluminescence and SPCC; bottom, emission spectra of both the free-space chemiluminescence and SPCC.
Figure 8:
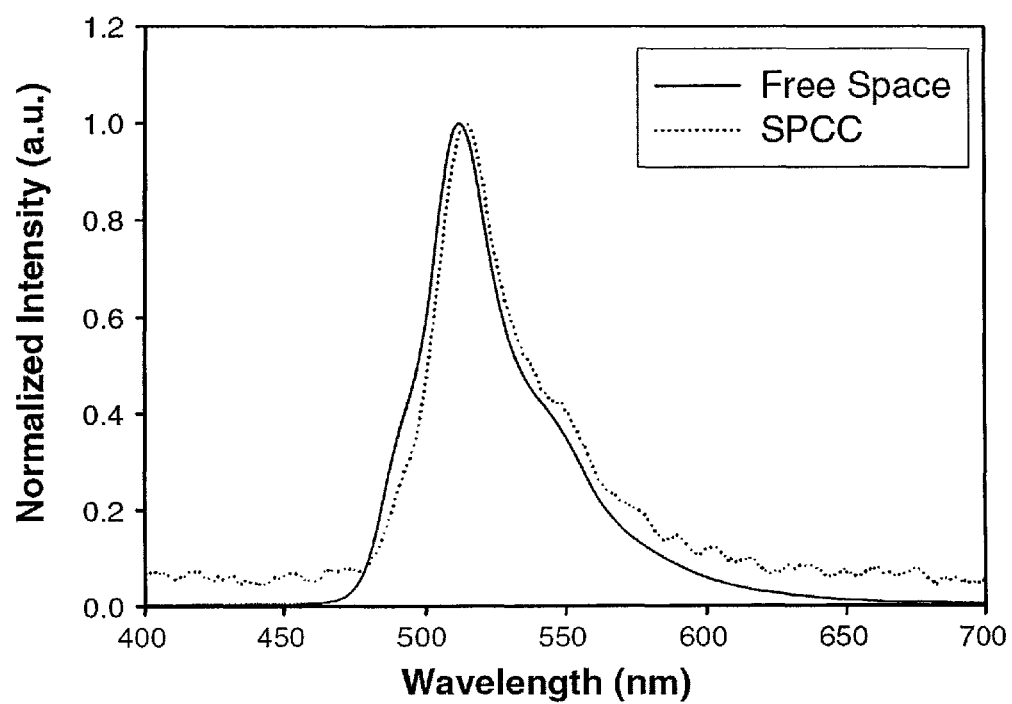

FIG. 8 (top left) shows the surface plasmon-coupled chemiluminescence (SPCC) and the free-space emission from the green chemiluminescent dye on a 45-nm silver layer. Similar to the case of the blue dye on aluminum, it can also be seen here that the free-space emission is of greater magnitude than the SPCC signal. FIG. 8 (top right) is an enlarged figure showing the highly directional and predominantly p-polarized SPCC emission only, suggesting that the observed signal is due to surface plasmons. This again is in stark contrast to the free-space emission which does not show any polarization or directional preference. FIG. 8 (bottom) is the normalized SPCC and free-space emission spectra showing a high degree of overlap between the spectra, suggesting no additional interaction between the luminescent species and the metal surface.

Figure 9:
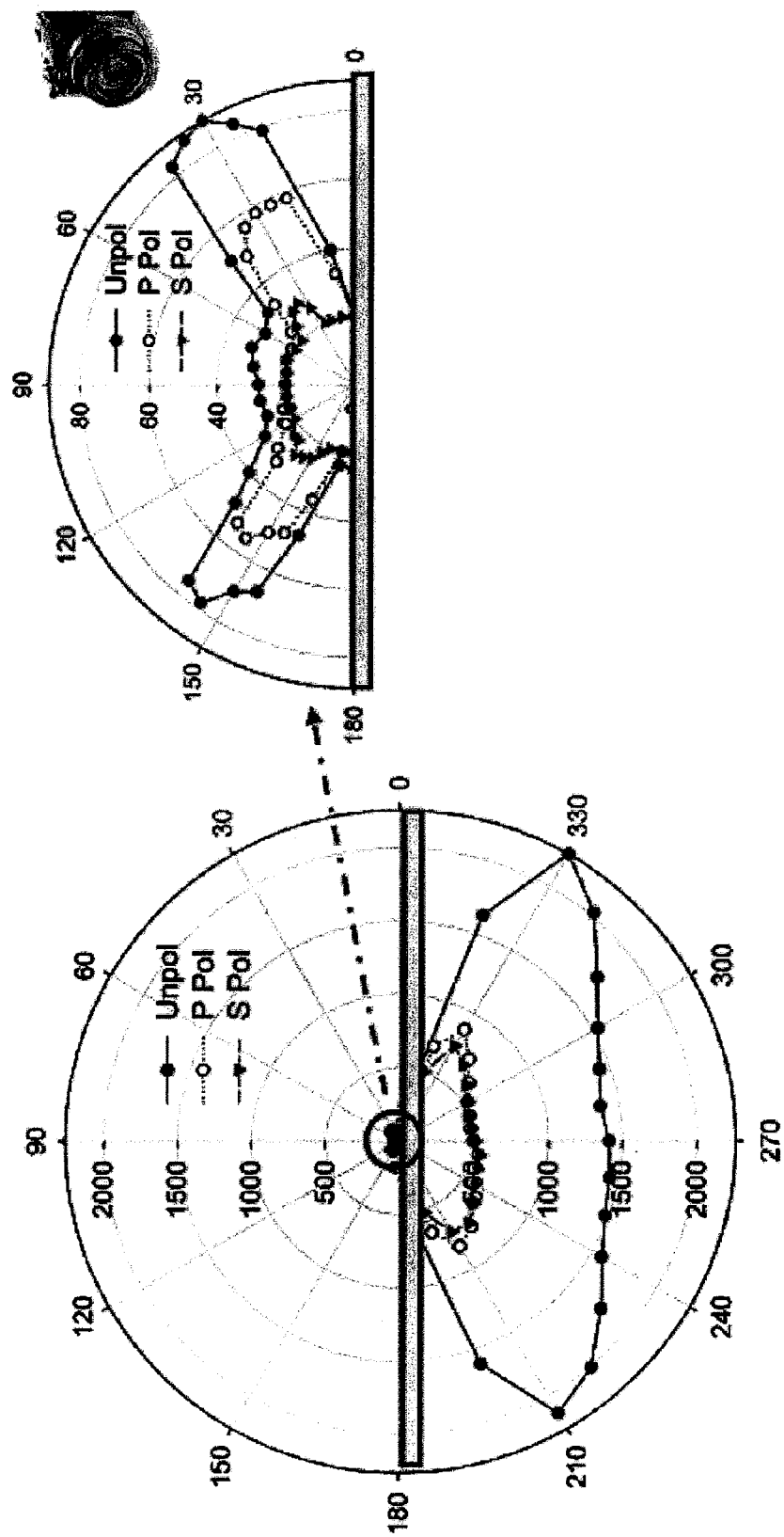
FIG. 9 shows surface plasmon-coupled chemiluminescence from 42-nm-thick gold films. Top right, enlarged directional SPCC; top left, free-space chemiluminescence and SPCC; bottom, emission spectra of both the free-space chemiluminescence and SPCC.
Figure 9:
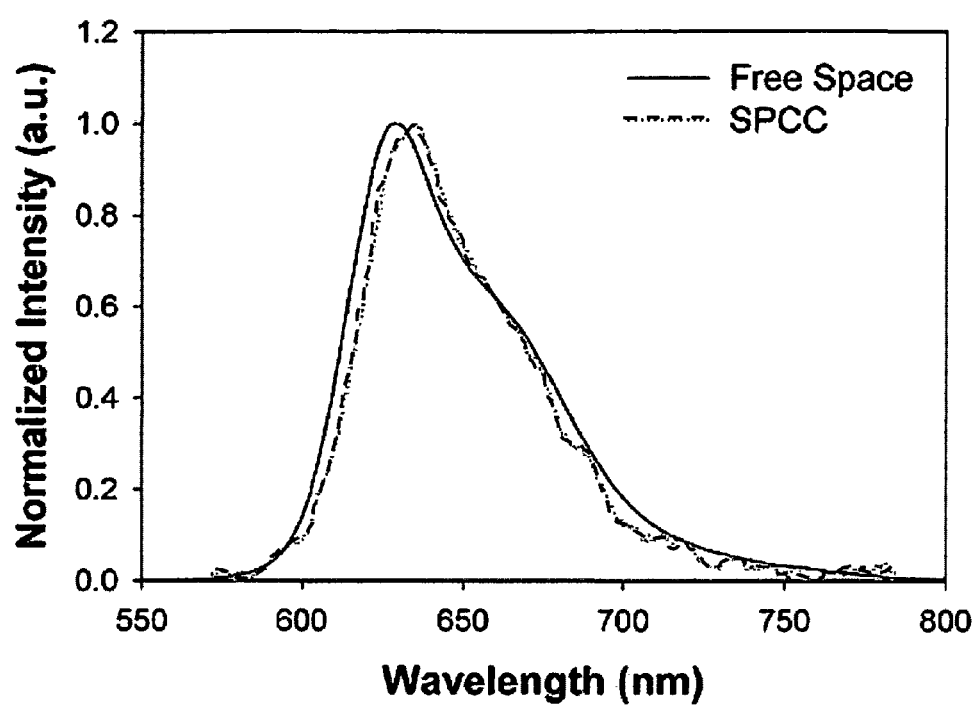

FIG. 9 (top left) shows the surface plasmon-coupled chemiluminescence (SPCC) and the free-space emission from the red chemiluminescent dye on a 42-nm gold layer. FIG. 9 (top right) is an enlarged figure showing the highly directional and predominantly p-polarized SPCC emission only, suggesting that the observed signal is due to surface plasmons. The SPCC again is in stark contrast to the free-space emission which does not show any polarization or directional preference. FIG. 9 (bottom) is the normalized SPCC and free-space emission spectra showing a high degree of overlap between the spectra, suggesting no other interaction between the luminescent species and the metal surface.

FIG. 10 shows photographs of the coupled emission (from the prism side) at the respective SPCC peak angle from the various dyes at both s- and p-polarizations as well as with no polarization. The approximate angular location of the camera used obtaining these photographs is marked in FIGS. 7-9 (top right). This figure clearly shows that the emission at the SPCC peak angle is predominantly p-polarized for all three dyes (on all three metals) thus suggesting that surface plasmons are responsible for the SPCC signal. It can be seen that the p-polarized signal intensity at the SPCC peak angle is lower in magnitude than the unpolarized signal. This occurs because the entire SPCC signal consists of both p- and to a lesser degree s-polarized light, and also because the sheet polarizers used in the experiment have only 30-40% peak transmission efficiency for both polarizations.

Figure 11:
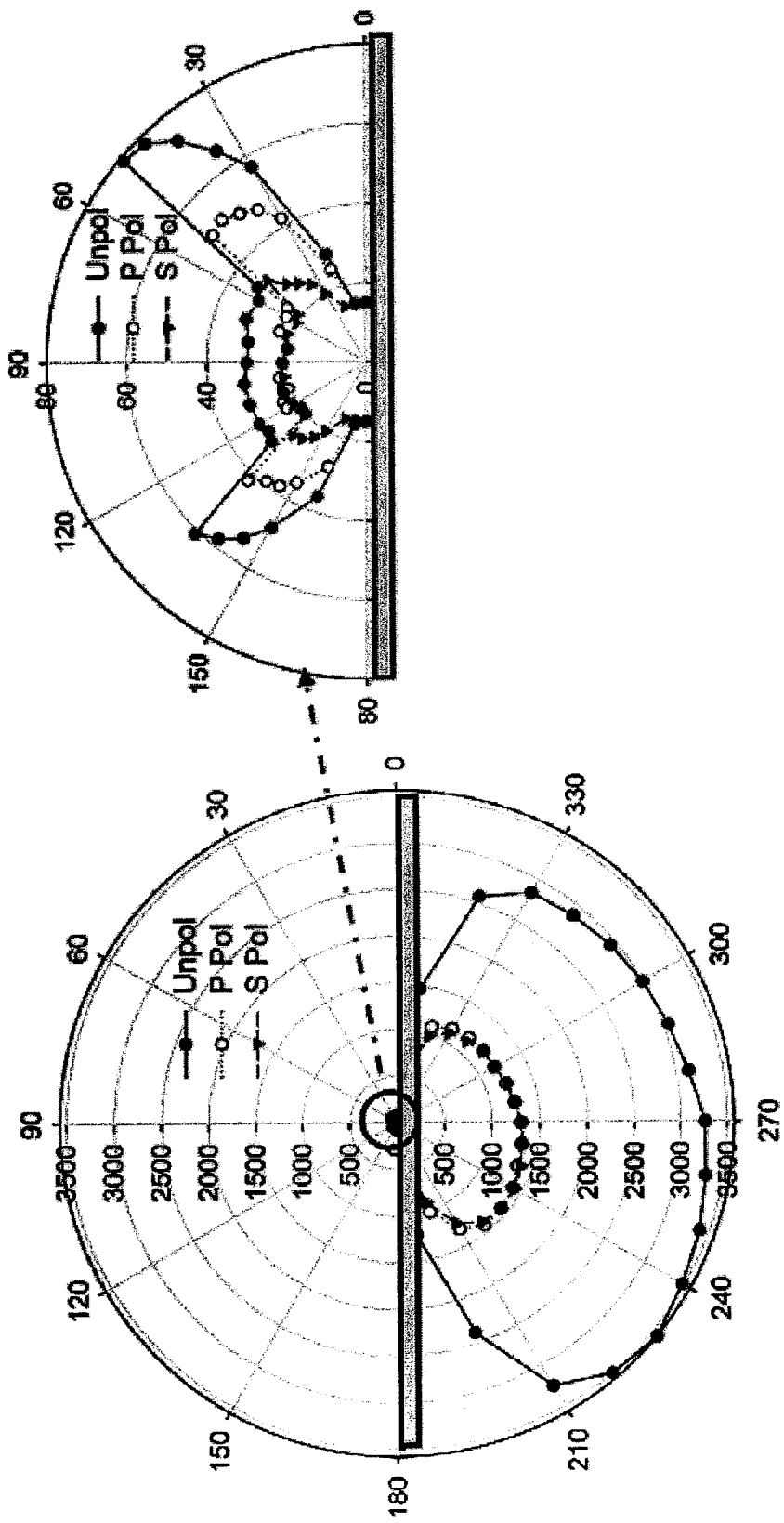
FIG. 11 shows surface plasmon-coupled chemiluminescence (SPCC) and free-space chemiluminescence from a small sample chamber, top left, and the enlarged coupled region, top right. Bottom, emission spectra of both free-space chemiluminescence and SPCC from the small chamber.
Figure 11:
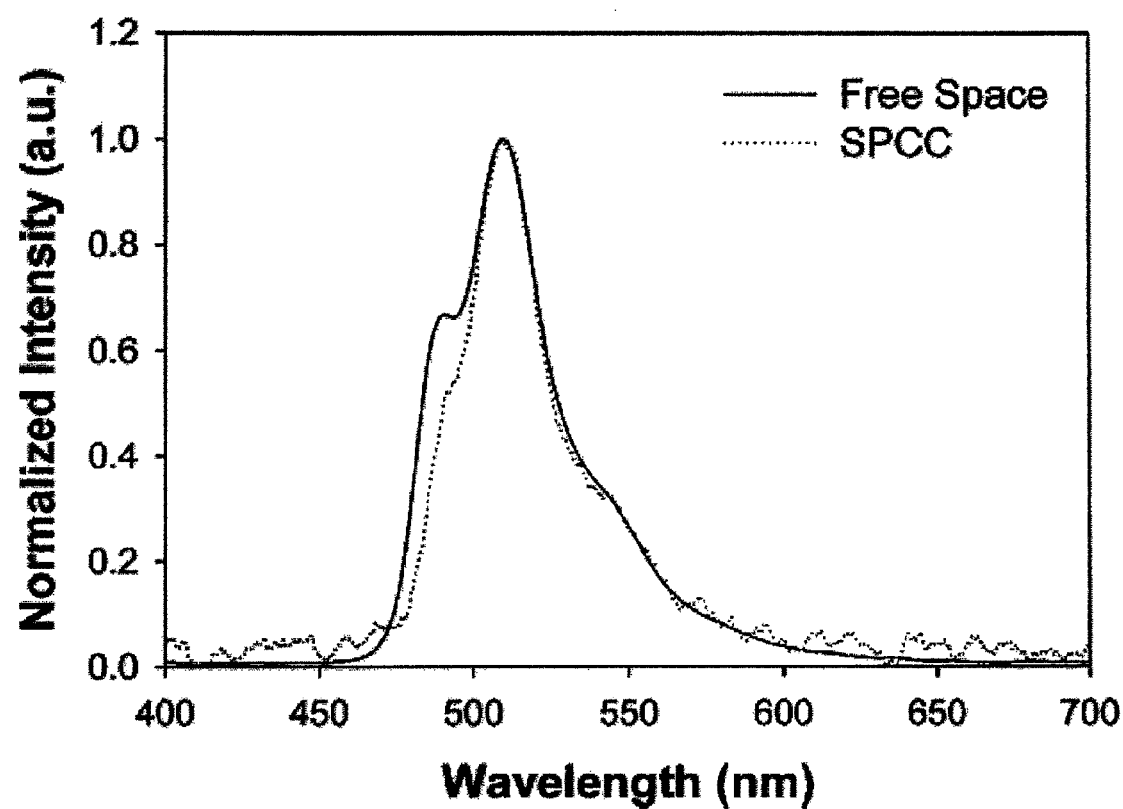

Initially, the broadness of the SPCC peak angles for all three dyes which varied between 20 and 25 degrees. Hence, to investigate whether the broadness of the SPCC peak angle is a function of the surface area of the sample, the experiments were repeated on silver using the green chemiluminescent dye with a sample chamber that had approximately half the surface area when compared to the samples made with commercially available imaging chambers that had been used thus far. FIG. 11 (top left) shows the surface plasmon-coupled chemiluminescence (SPCC) and the free-space emission from the green chemiluminescent dye on a 45-nm silver layer for the small imaging chambers. FIG. 11 (top right) is an enlarged figure showing the highly directional and predominantly p-polarized SPCC emission only. Here, the broadness of the SPCC peak angle is approximately 20 degrees. It is clear from this figure that the broadness of the SPCC peak angle is not significantly affected by the surface area of the sample. An interesting observation in FIG. 11 (top right) is the decay in the SPCC signal in the region between 90 and 180 degrees when compared to that in the 0-90 degrees. This is because the data was collected sequentially from 0 through 360 degrees. As a result, for the small chamber with a lower volume of reactants, by the time the data in the region between 90 and 180 degrees was collected, a signal reduction is observed because of the depletion of reactants (depletion of excited states) over time. The broad angle distribution shown in FIGS. 7-9 and 11 is attributed to the waveguide effect, given that our solution of chemiluminescence occupied a sample chamber of 1-mm thickness. FIG. 11 (bottom) is the normalized SPCC and free-space emission spectra showing a high degree of overlap between the spectra, suggesting no additional interaction between the luminescent species and the metal surface in the smaller imaging chambers built in-house.

Figure 12:
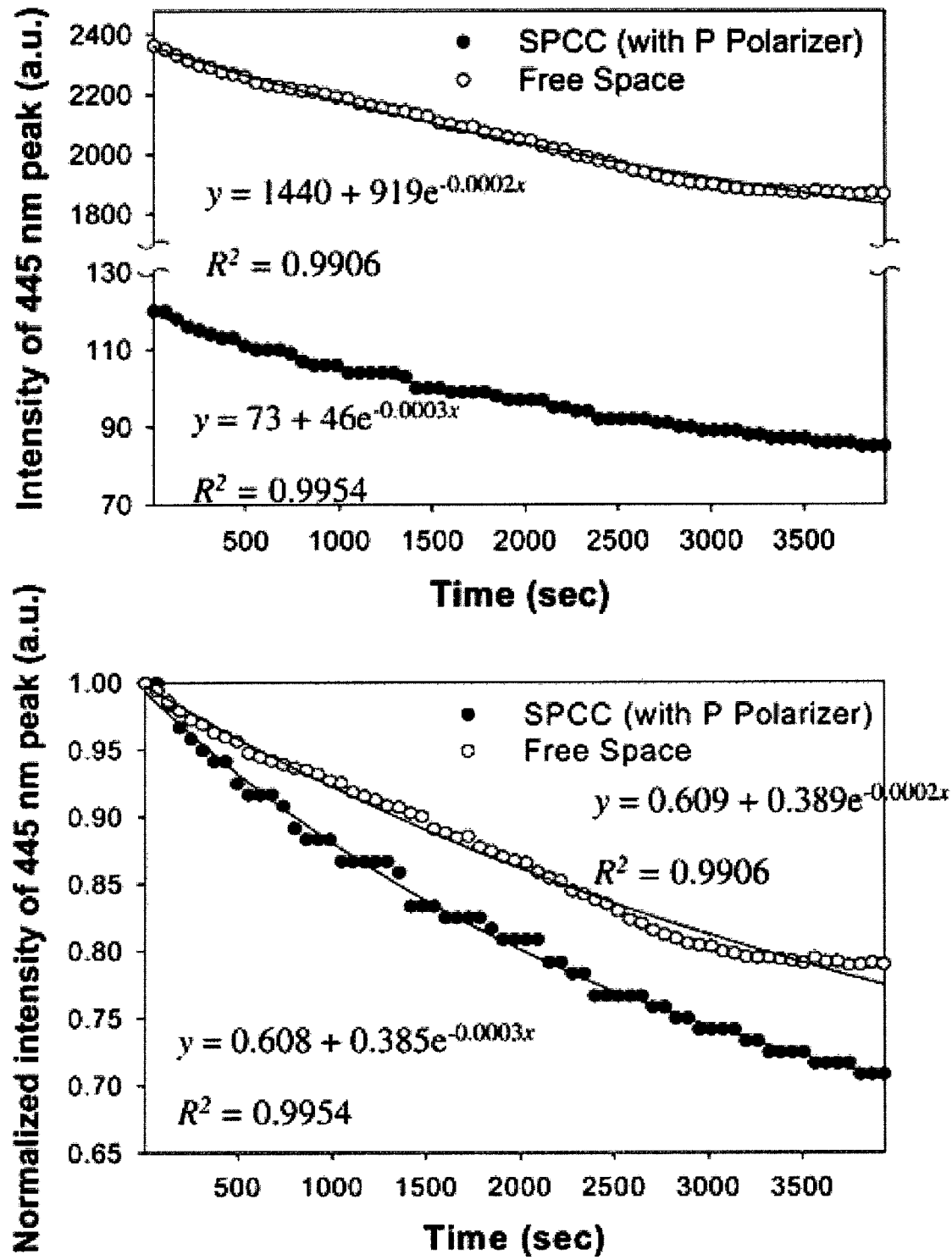
FIG. 12 shows that chemiluminescence intensity decays from aluminum films for both free space and coupled (top) and normalized to the same initial intensity (bottom).
Figure 13:
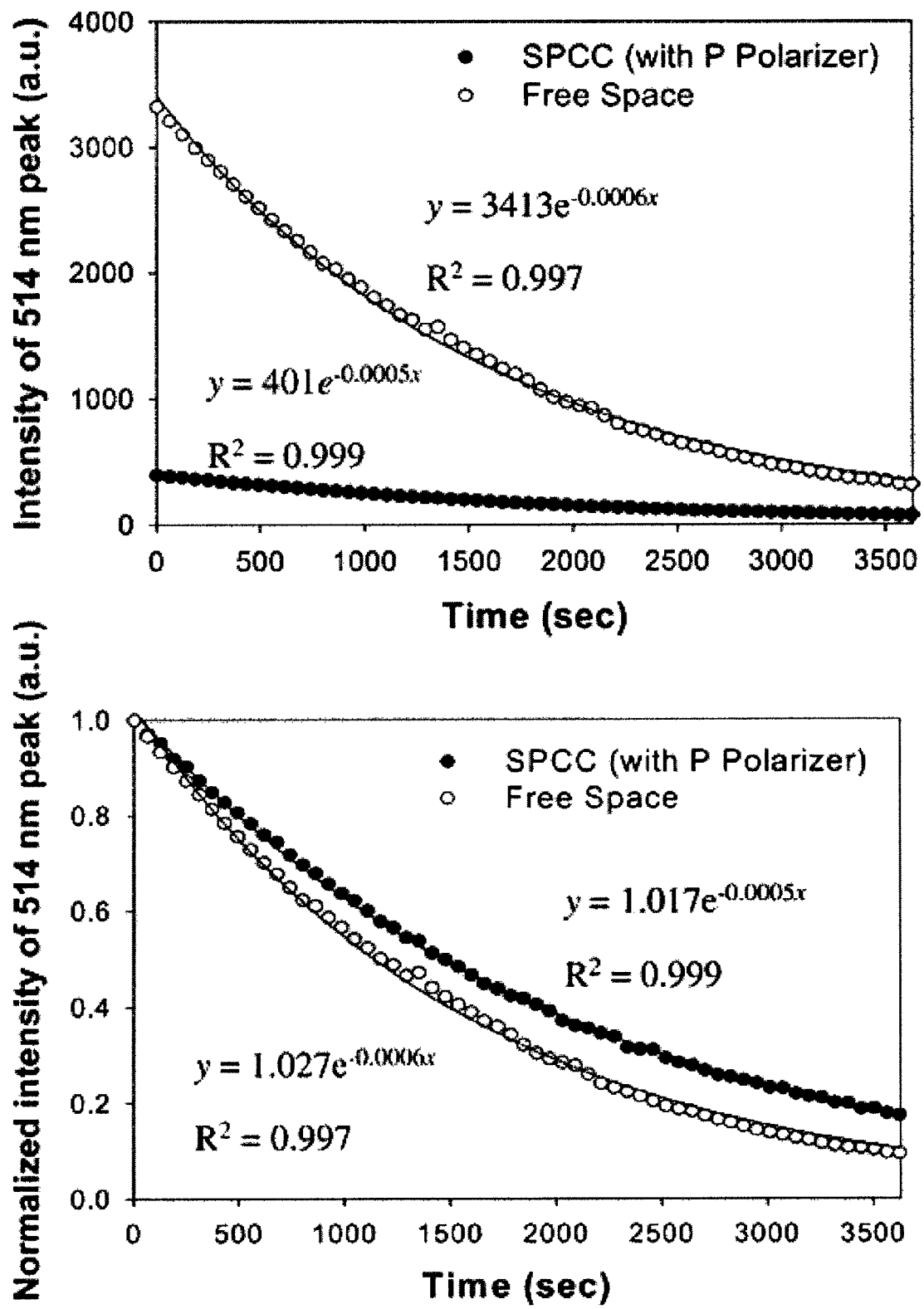
FIG. 13 shows that chemiluminescence intensity decays from silver films for both free space and coupled (top) and normalized to the same initial intensity (bottom).

The next round of experiments was performed to determine the rate of decay of luminescence for the blue and green chemiluminescent dyes as a function of time for both the free-space emission and the SPCC emission (with p-polarizers so that only plasmon-coupled emission was measured). By decay rate, it is meant the decrease in intensity because of depletion of reagents. The results of these experiments for the blue dye on aluminum and green dye on silver are shown in FIGS. 12 and 13, respectively. FIG. 12 (top) shows the decay of free-space and SPCC emission as a function of time for the blue dye on aluminum, with FIG. 12 (bottom) image showing both the decay intensities normalized to their respective values at t=0. The rate of loss of luminescence, which is due to the depletion of solution reactants and therefore a depletion over time of excited states, was found to follow first-order decay kinetics as shown herein above in formula (3).

The rate of depletion of the SPCC signal for the blue dye on aluminum was found to be only minimally greater than the free-space emission, 0.0003 versus 0.0002 $s^{-1}$, respectively. Since both the SPCC signal and the free-space emission signal decay are highly dependent on the rate of depletion of the same reactants (depletion of excited states) in the sample chamber over time, it is not surprising that the measured decay rates for both the signals as shown in FIG. 12 are almost identical. However, this finding does indicate that there are no localized catalytic effects of the aluminum on the chemiluminescence reaction, as this would be expected to manifest in a larger difference in the SPCC luminescence decay rate (from the free-space decay rate) than is currently observed.

FIG. 13 (top) shows the decay of free-space and SPCC emission as a function of time for the green chemiluminescent dye on silver, and FIG. 13 (bottom) shows both the decay intensities normalized to their respective values at t=0. The rate of depletion of the SPCC signal for the green dye on silver was found to be only minimally smaller than the free-space emission, 0.0005 versus 0.0006 $s^{-1}$, respectively. It is again not surprising that the measured decay rates for both the signals as shown in FIG. 12 are almost identical, since both the SPCC signal and the free-space emission signal decay are highly dependent on the rate of depletion of the same reactants in the sample chamber over time. This finding again indicates no localized catalytic or chemical effects of the silver on the chemiluminescence reaction studied.

2.7. Conclusions

The results of this study lead us to conclude that chemically induced electronic excited states of luminophores can excite surface plasmons on thin films of continuous metal, producing highly polarized and directional emission. This phenomenon is not restricted to the commercially available kits that were used in this study but rather can be extended to the myriad of chemiluminescent reactions employed in biotechnology today to increase signal collection efficiency and hence the sensitivity of such assays. The typical thickness of the functional surface of such assays are compatible with an approximately 250-nm coupling region, potentially alleviating unwanted background signals caused by spontaneous reaction of reagents or unwanted enzymatic activity and therefore increasing assay sensitivity.

Another interesting observation is that SPCC occurs with gold films. Since luminophores within approximately 250 nm of the surface of metal are known to excite surface plasmons, which is longer than the distances required for nonradiative quenching of luminescence, the potential of using gold as the metal surface becomes an advantage. This is because gold is chemically more stable than silver and the surface chemistry of gold is well-known and characterized [37]. Also, since gold films are widely used in surface plasmon resonance (SPR), this provides a robust technology base for the mass production of suitable gold films.

3. Microwave Triggered Metal Enhanced Chemiluminescence 3.1 Materials

Bovine-biotinamidocaproyl-labeled albumin (biotinlyated BSA), HRP-labeled avidin, silver nitrate (99.9%), sodium hydroxide (99.996%), ammonium hydroxide (30%), trisodium citrate, D-glucose, and premium quality APS-coated glass slides (75×25 mm) were obtained from Sigma-Aldrich. CoverWell imaging chamber gaskets with adhesive (20-mm diameter, 1 mm deep) were obtained from Molecular Probes (Eugene, Oreg.). Steptavidin-HRP prediluted solution was obtained from Chemicon International Inc. Chemiluminescence materials were purchased from Amersham Biosciences (ECL Plus Western blotting detection kit, RPN2132). ECL Plus utilizes a new technology, developed by Lumigen Inc., based on the enzymatic generation of an acridinium ester, which produces intense light emission at ~430 nm.

3.2. Formation of Silver Island Films on APS-Coated Glass Substrates

In a typical SiF preparation, a solution of silver nitrate (0.5 g in 60 mL of deionized water) in a clean 100-mL glass beaker, equipped with a Teflon-coated stir bar, is prepared and placed on a Corning stirring/hot plate. While stirring at the quickest speed, 8 drops (~200 μL) of freshly prepared 5% (w/v) sodium hydroxide solution are added. This results in the formation of dark brown precipitates of silver particles. Approximately 2 mL of ammonium hydroxide is then added, drop by drop, to redissolve the precipitates. The clear solution is cooled to 5° C. by placing the beaker in an ice bath, followed by soaking the APS-coated glass slides in the solution. While keeping the slides at 5 C, a fresh solution of D-glucose (0.72 g in 15 mL of water) is added. Subsequently, the temperature of the mixture is then warmed to 30° C. s the color of the mixture turns from yellow-green to yellow-brown, and the color of the slides become green, the slides are removed from the mixture, washed with water, and sonicated for 1 min at room temperature. SiF-deposited slides were then rinsed with deionized water several times and dried under a stream of nitrogen gas. Prior to assay fabrication and subsequent chemiluminescent experiments, imaging chamber gaskets with adhesive (20-mm diameter, 1 mm deep) were pressed against the silver-coated and silica-capped microscope glass slides until they were stuck together, creating a chamber.

3.3. Preparation of the Model Protein Assay (Biotin-Avidin) on Silver Island Films and on Glass The model assay used in the present experiment is based on the well-known interactions of biotin and avidin. Biotin groups are introduced to the glass and silvered surfaces through biotinylated BSA, which readily forms a monolayer on the surfaces of glass and SiFs. Biotinylated BSA is bound to SiFs and the glass by incubating 20 μL of biotinylated BSA solutions with different concentrations in the imaging for ~1 h. Chambers were washed with water to remove the unbound material. Imaging chambers were then incubated with 20 μL of 1% aqueous BSA (w/v) for 1 h to minimize nonspecific binding of HRP-streptavidin to surfaces. Chambers were again washed with water to remove the BSA blocking solution. Stock solutions of HRP-streptavidin were diluted 1:10 to a final concentration of 100 μg/mL. Twenty microliters of the HRP-streptavidin solution was subsequently added into the biotinylated BSA-coated glass and SiF-coated imaging chambers and typically microwaved for 20 s in the microwave cavity (0.7 ft$^3$, GE compact microwave model JES735BF, max power 700 W). The power setting was set to 2, which corresponded to 140 W over the entire cavity. In all the experiments performed with low-power microwaves, there was no evidence of surface drying. Following incubation, imaging chambers were again washed with water to remove unbound HRP-streptavidin material prior to the chemiluminescence experiments.

3.4. Chemiluminescence Reagents

The ECL Western blotting detection kit contained two reagents that yield a bright chemiluminescent emission at 430 nm upon mixing. Solution A contained the substrate solution (peroxide formulation), and solution B contained the solution of the luminescent compound, acridan in dioxane and ethanol. HRP and hydrogen peroxide solution (solution A) catalyze the oxidation of the acridan substrate (solution B). As a result, acridinium ester intermediates are formed and further react with peroxide to generate light emission with a maximum wavelength centered around 430 nm.

3.5. Chemiluminescence from Reagents on SiFs and Glass Surfaces

The chemiluminescence experiments were performed with and without microwave heating inside the microwave cavity. During microwave heating, 30-s pulses were applied at three 100-s intervals. The pulses were applied at 30% power, which corresponded to 210 W over the entire cavity. In order to obtain the same initial chemiluminescence emission for all measurements, all chemiluminescent assays were undertaken by combining 40 μL of solution A with 2.0 μL of solution B and immediately adding the entire solution to the imaging chamber.

Data collection commenced immediately following addition of reagents and terminated when the photon count returned to baseline. Since the rate of photon emission is directly proportional to enzyme concentration, the photon flux was summed for a fixed time interval for the points shown in FIG. 16 to determine the relationship between protein concentration and signal intensity, cf. FIGS. 19 and 20.

3.6. Chemiluminescence Detection

Chemiluminescence spectra were collected using an Ocean Optics spectrometer, model SD 2000 (Dunedin, Fla.), connected to an Ocean Optics 1000-mm-diameter fiber with an NA of 0.22. The fiber was positioned vertically on top of the slides containing the chemiluminescent reagents inside the microwave cavity. Chemiluminescent spectra and time-dependent emission intensities were collected with an integration time of 1000 ms for ~500 s unless otherwise noted. The integration time was kept constant between the control and silver island film sample measurements. The real-color photographs were taken with an Olympus Digital camera (C-740, 3.2 Mega Pixel, 10× Optical Zoom) without the need for optical filters.

3.7. Results

Figure 14:
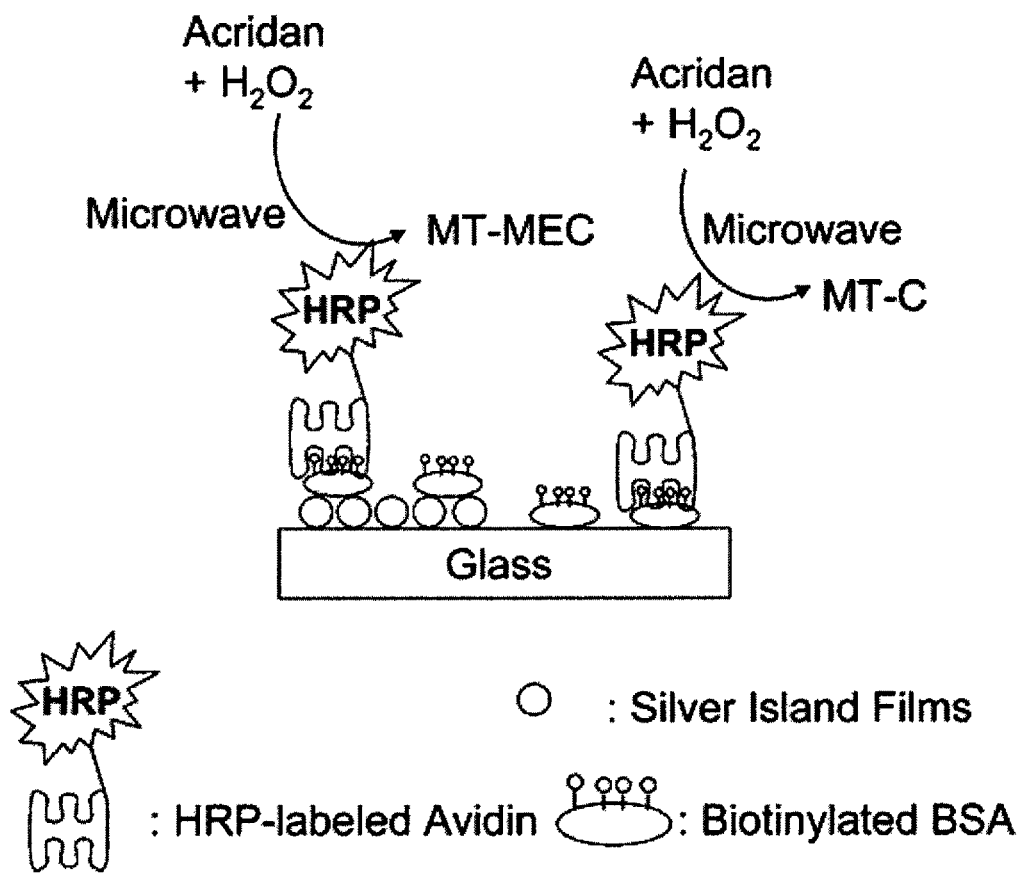
FIG. 14 shows a setup for HRP-acridan chemiluminescence assay on both glass and silvered slides.

To demonstrate protein detection with microwave triggered metal enhanced chemiluminescence (MT-MEC) on silver island films (SiFs), commercially available chemiluminescent reagents (acridan and peroxide) from Amersham Biosciences was used. The model protein assay was constructed with biotinylated BSA surface-modified substrates (SiFs or glass), horseradish peroxidase-streptavidin (HRP-avidin) and chemiluminescent reagents, as demonstrated in FIG. 14.

Biotinylated BSA was incubated on silvered or glass substrates for ~1 h. A 1% aqueous BSA solution was subsequently added to minimize nonspecific binding of HRP-streptavidin to the surfaces. HRP-streptavidin was then added to the surfaces with bound biotinylated BSA. The strong binding affinity of streptavidin for biotin served as the basis for the quantitative determination of the BSA-biotin species on the glass and silvered surfaces. As a result, chemiluminescent reaction rates for these experiments are proportional to the quantity of bound biotinylated BSA HRP-streptavidin complexes, [38] where the dynamic range of protein concentration is proportional to the total luminescent photon flux for a defined time interval.

Following surface modification of glass and silver surfaces, a comparison was made between traditional chemiluminescence reaction yields with microwave (Mw) "trigger" reaction yields. With the addition of the chemiluminescent mixtures to the functionalized surfaces, the emission data was collected for the MT-MEC assays within the microwave cavity using a fiber optic that is connected to a spectrofluorometer and a computer (not shown). The microwave cavity power was ~140 W. Detection was accomplished through a fiber delivered through a small opening on the top of the microwave cavity. Imaging chambers were placed in the microwave, and wells of interest were aligned with the tip of the fiber to optimize collection efficiencies.

Figure 15:
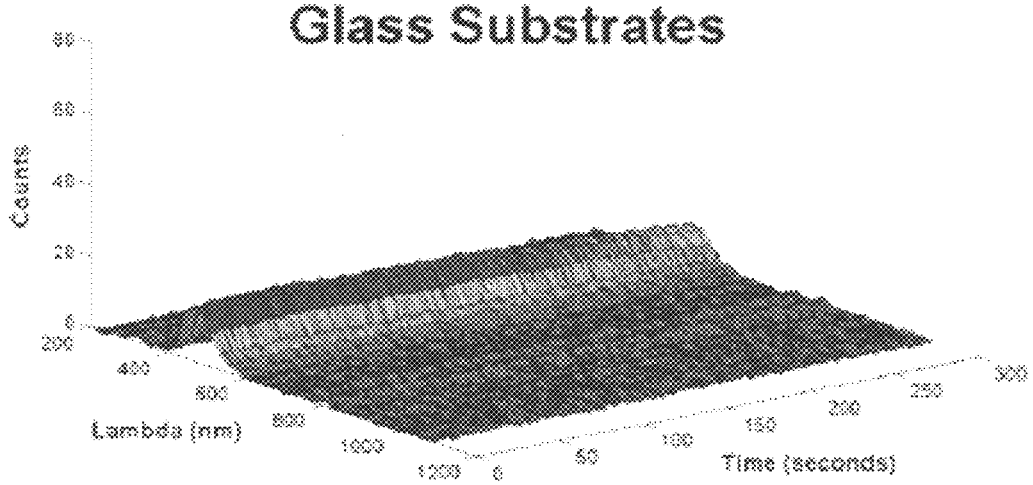
FIG. 15 shows 3D plots of acridan assay emission as a function of time from glass slides without (top) and with low-power microwave exposure/pulses (middle). (Bottom) Photographs showing the acridan emission both before (a) and after a low-power microwave pulse (b). Mw, microwave pulse. The concentration of BSA-biotin was 1.56 pM.
Figure 15:
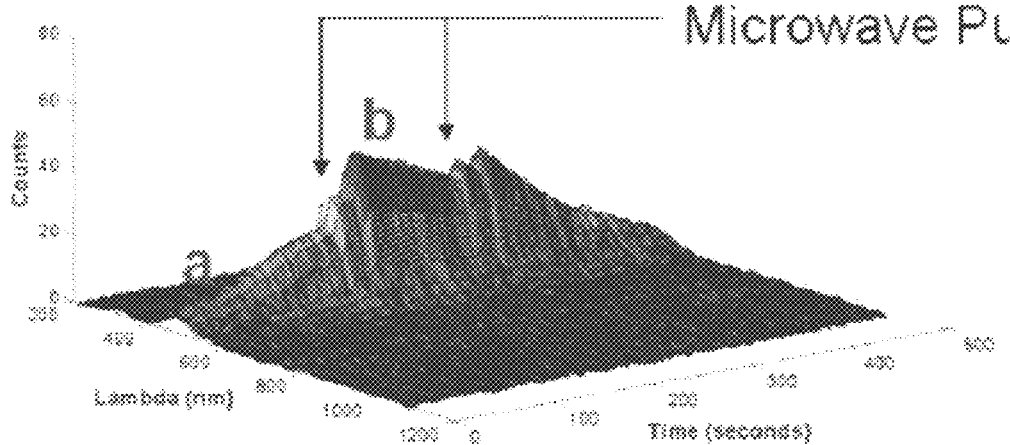
Figure 15:
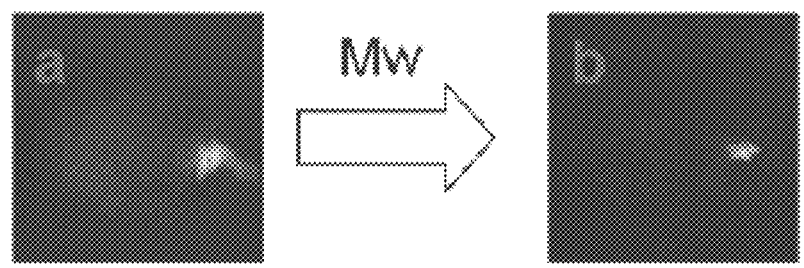

FIG. 15 top shows the first 500 s of collection time for the chemiluminescence emission from the glass surfaces. FIG. 15, bottom, shows the chemiluminescence emission from the glass substrate under the same initial conditions, but the sample is subjected to 30-s microwave pulses at ~100-s intervals. These results clearly show the "on-demand" nature of microwave-triggered chemiluminescence reactions. The most striking feature of FIG. 15 is the enhancement of the photon flux upon the application of discrete microwave pulses. In essence, these results demonstrate the feasibility of increasing reaction rates of chemiluminescent reactions and dramatically improving photon flux for finite time intervals. As a result, chemiluminescent reactions that typically generate limited light emission over extended periods of time can be subsequently accelerated with the addition of low-power microwave pulses.

Figure 16:
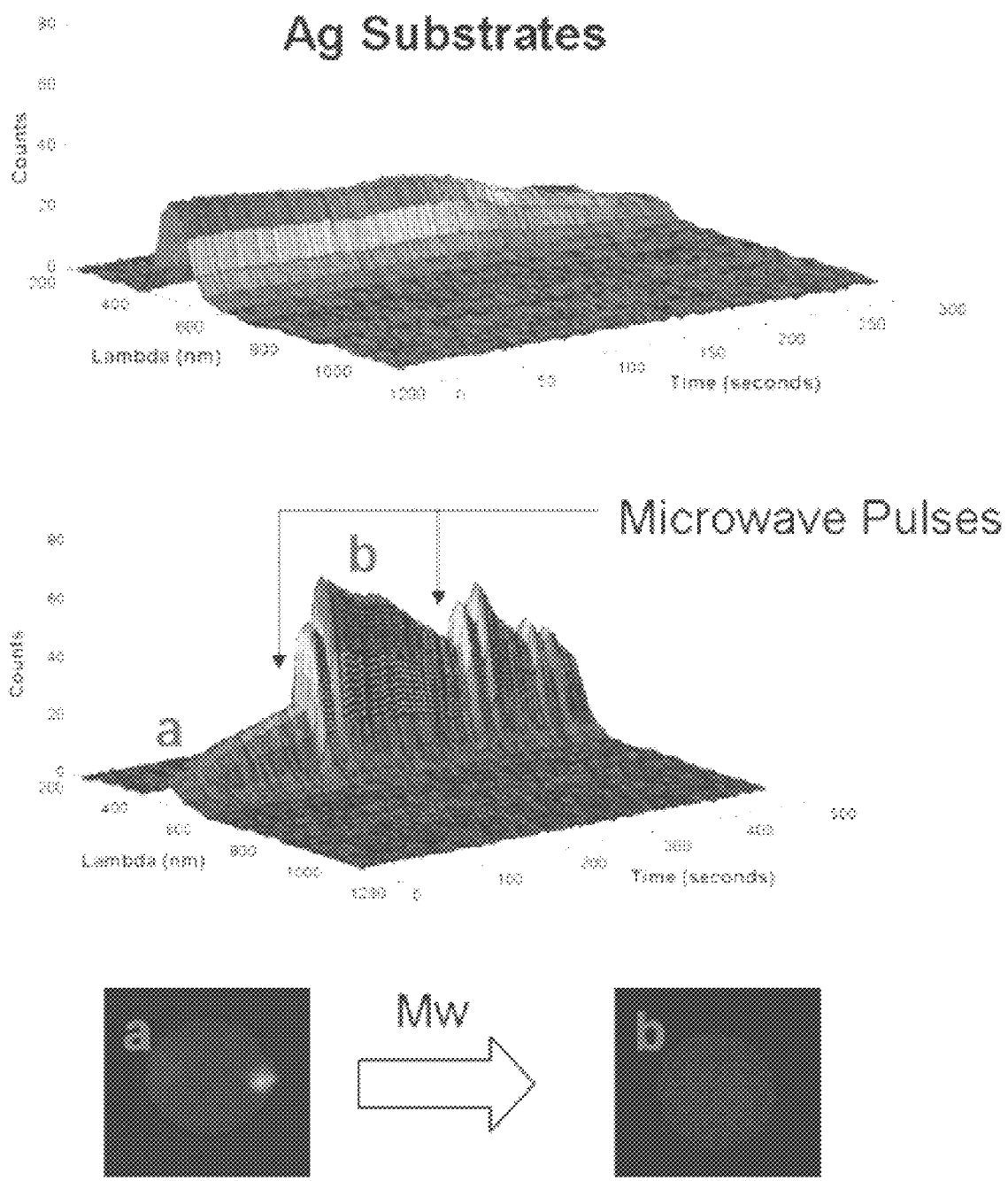
FIG. 16 shows 3D plots of the acridan assay chemiluminescence emission as a function of time from silvered glass slides (Ag) without (top) and with low-power microwave exposure/pulses (middle). (Bottom) Photographs showing the acridan emission both before (a) and after a low-power microwave pulse (b). Mw, microwave pulse. The concentration of BSA-biotin was 1.56 pM.

FIG. 16 demonstrates significant enhancement with microwave pulses from silver island films. FIG. 16, top, shows metal-enhanced chemiluminescence. As compared to the results of FIG. 15 top, it is evident that there is a pronounced increase in photon flux from the metal surfaces; cf. FIG. 15, top, a 3-fold enhancement in signal is observed from the silvered surfaces shown in FIG. 16. These results are further demonstrated with the insets in FIGS. 15 and 16 that show the real-color photographs of the chemiluminescent reagents (before and after Mw exposure) on glass and the SiF surfaces. When subjected to low-power microwaves as shown in FIG. 16, bottom, chemiluminescence from the silver island films is even further enhanced for the microwave pulse time intervals. It is theorized that the high photon flux evident upon delivery of microwave pulses to the metal surface is attributed to localized heating of the metal surfaces. The local temperature increase not only accelerates the rate of the chemiluminescence reactions, but the proximity to the silver allows for metal-enhanced chemiluminescence. Thus, a reaction that traditionally is followed over extended periods of time can be "triggered" in short discrete time intervals with low-power microwaves.

The microwave heating of the whole sample (SiFs, HRP, and bulk solution) affects the enzyme-catalyzed chemiluminescence reactions in two ways: (1) since the enzyme is only on the surface of the silver nanoparticles, the chemiluminescence reactions only happen on SiFs, and the dissipated energy by SiFs is thought to lower the energy required for these reactions; (2) the heating of the solution increases the diffusion of chemiluminescent species so that the chemiluminescence reactions go faster. Although, the percent contribution of these factors to the overall reaction rate is unknown, it is believed that the localized heating effect is more dominant.

Figure 17:
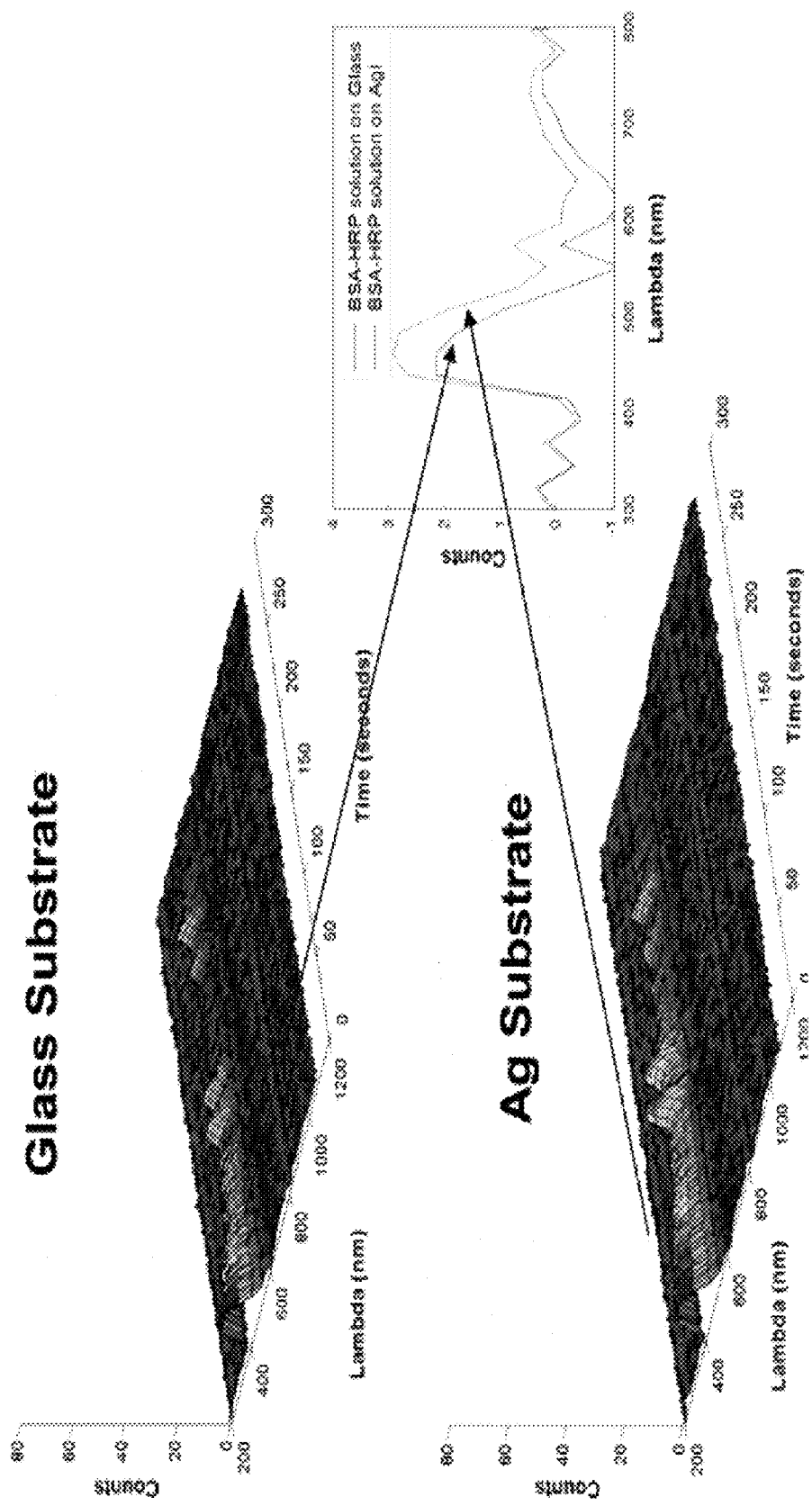
FIG. 17 shows 3D plots of the acridan assay chemiluminescence emission from both glass (top) and silvered substrates (bottom). (Right) Emission spectra are the average of 400 1-s time points. In both cases, BSA-biotin was not immobilized to the surfaces, which were exposed to microwave pulses at 100- and 200-s time points. The final concentration of HRP-streptavidin in the assay was ~10 µg/mL.

The chemiluminescent reactants and HRP-streptavidin were mixed in solution (100 μg/mL) to demonstrate that the localized chemiluminescent enhancement in the presence of silver island films is no longer observed. Data were collected for 400 s, and solutions were pulsed with low-power microwaves for 30 s at the 100- and 200-s time points during the course of the reaction. FIG. 17, top and bottom, depict a fast signal decay for the reactions in solution above both glass and silver. In addition, upon application of the first microwave pulse, a small signal enhancement was evident, which is due to the few HRP molecules and chemiluminescent reactants that have settled close to the surfaces. For the second microwave pulse, very little signal enhancement is seen and, eventually, no signal observed at longer times. It is theorized that this result affirms the assertion that preferential heating of the nanostructures by microwaves affords for MT-MEC to be localized in proximity to the silvered surfaces, alleviating unwanted emission from the distal solution.

Figure 18:
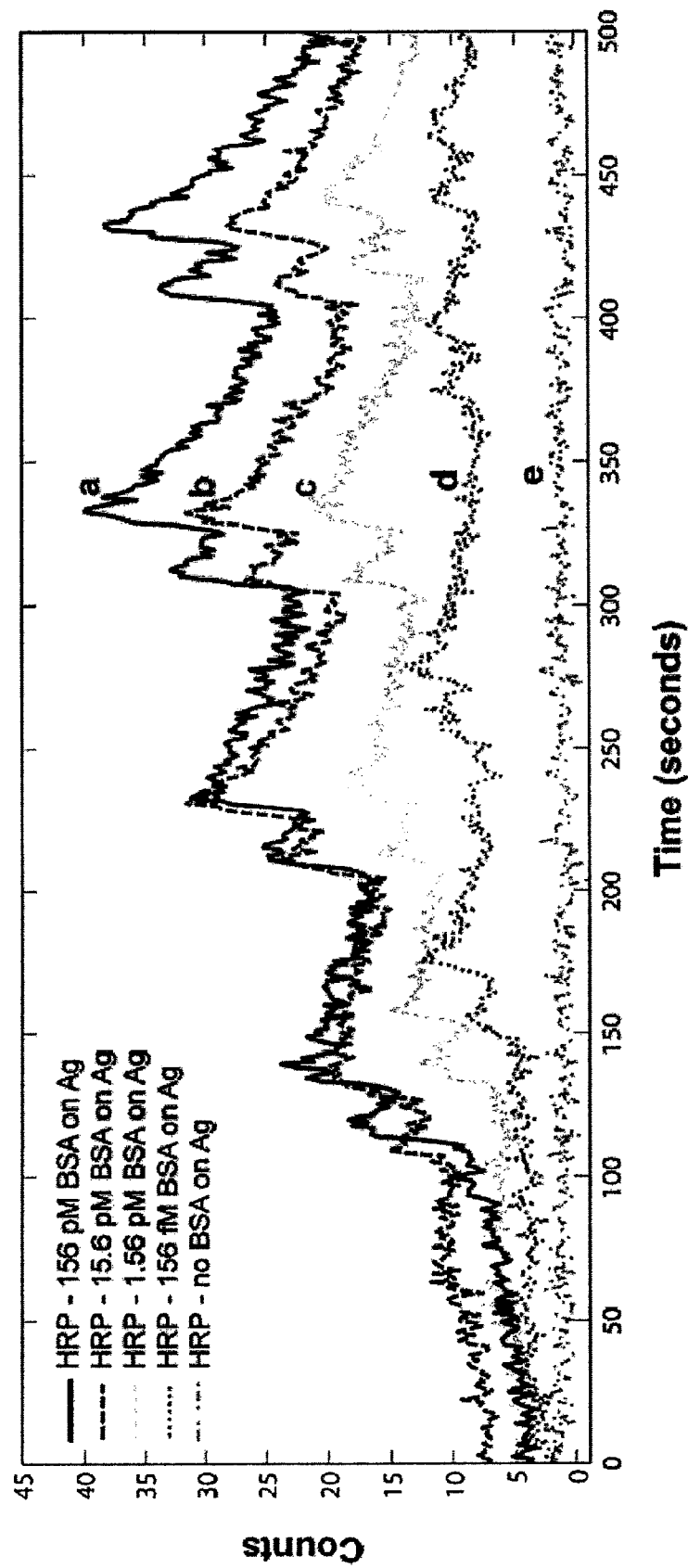
FIG. 18 shows the acridan chemiluminescence emission intensity as a function of time for different concentrations of surface-bound BSA-biotin. a, 156 pM BSA-biotin; b, 15.6 pM BSA-biotin; c, 1.56 pM BSA-biotin; d, 156 fM BSA-biotin; and e, no BSA-biotin.

In order to demonstrate the "on-demand" nature of MT-MEC and induce the higher sensitivity of detection, the amount of biotinylated BSA incubated on the substrate surfaces was varied to demonstrate the concentration dependence for MT-MEC. FIG. 18 shows the time-dependent chemiluminescent emission of the chemiluminescence reaction on SiFs and glass surfaces with multiple microwave exposures (four 30-s exposures, 100-s intervals). As previously observed in FIGS. 15 and 16, the intensity "spikes" correspond to the microwave pulses that trigger enhanced chemiluminescence from the HRP functionalized substrates. Each curve (a-e) corresponds to a different concentration of biotinylated BSA incubated on a silver substrate.

From FIG. 18, it can be determined that the chemiluminescence intensity is proportional to the concentration of HRP bound to BSA-functionalized surfaces. Thus, this result, enables the surface protein concentration to be determined. It is important to explain the characteristics of the chemiluminescent intensity versus time plot, as shown in FIG. 18. In order to determine the concentration of surface proteins without microwave heating, the change in chemiluminescent intensity was monitored after the chemiluminescent reactions were initiated (no microwave heating) in the first 100 s. It is seen that, without microwave heating, the chemiluminescent intensity is slightly increased as the concentration of BSA is increased but little difference between them is observed, which proved to be a not useful method. On the other hand, to show the benefits of microwave heating to increase the detected chemiluminescent signal, four 30-s exposures (after 100 s) were performed with 100-s intervals to drive the chemiluminescent reactions to completion within 400 s (without microwave heating the reactions studies here are completed longer than 30 min) The photon flux (in counts), area under the intensity-time plot, is an indication of the extent of the HRP-catalyzed reaction and thus provides information about the presence of surface-bound BSA. The two "peaks" seen after each microwave exposure, in FIG. 18, are a result of the microwave magnetron pulsing. During the 10- and 5-s runs, the chemiluminescent intensity increases and decreases, respectively triggered by the magnetron pulsing and the localized heating of the microwaves. The peak height and the area under one of the peaks could be increased by using shorter exposure times (<10 s) and higher initial microwave power settings. However, it was found that higher initial power setting causes surface drying and was not found reliable for use here, as surface drying causes protein denaturation. In all the experiments performed with low-power microwaves, using both SiFs and glass, there was no evidence of surface drying. This is attributed to the previously made observations [20] that the temperature increase of the aqueous solution on the surfaces due to microwave heating is only ~8° C. (to ~28° C.) for 30 μL of aqueous sample [20].

Figure 19:
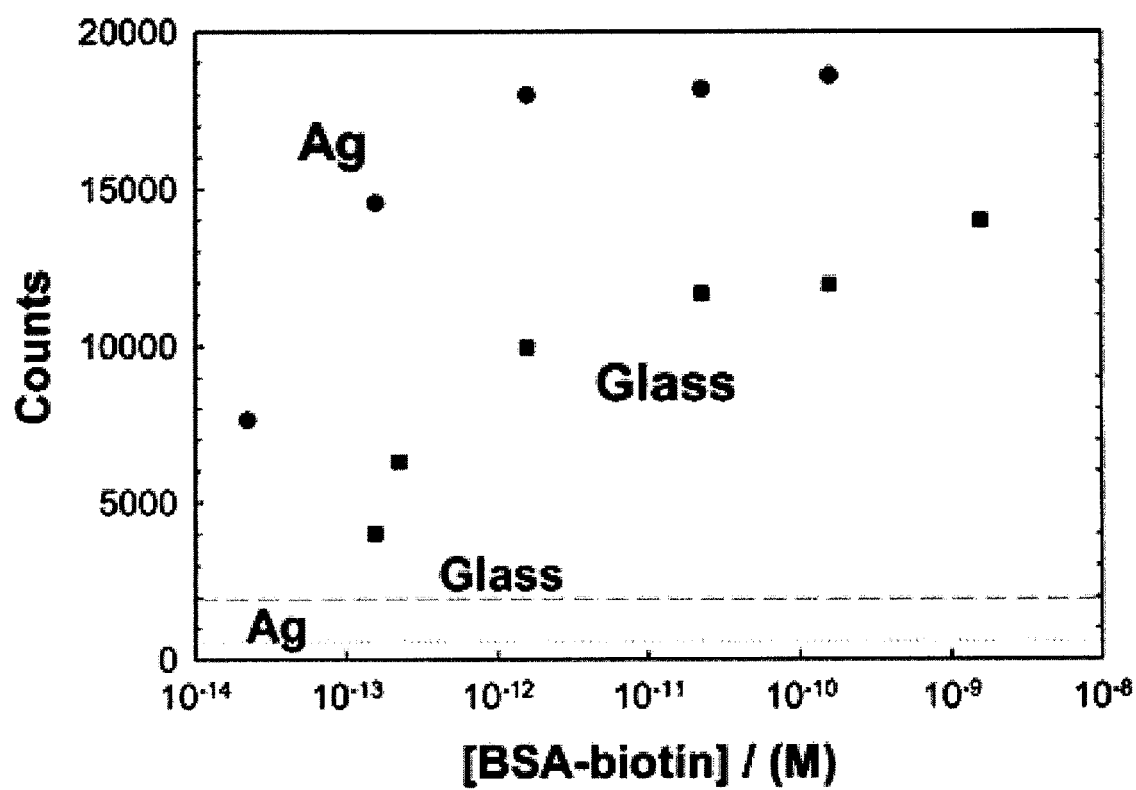
FIG. 19 shows photon flux integrated over 500 s of the assay shown in FIG. 18, for different concentrations of BSA-biotin from both glass and silvered surfaces (Ag). Baselines correspond to integrated photon flux over 500 s for glass and silvered surfaces (Ag) incubated with 1% BSA solution and streptavidin HRP.

It is interesting to compare the results of the protein concentration-dependent assays on both silvered and glass surfaces, FIG. 19. The overall signal enhancement shown in FIG. 18, for assays performed on silver substrates versus those on glass substrates, serves to confirm the benefits of using silver nanostructures for MEC. By combining the use of low-power microwaves and metal substrates to increase the rapidity of streptavidin binding to biotinylated BSA surfaces, decrease nonspecific background, and enhance and accelerate chemiluminescent reactions, FIG. 19 shows that it is possible to detect approximately femtomoles of biotinylated BSA on surfaces in less than 2 min, with a signal-to-noise ratio (S/N)

greater than 8. Signal-to-noise ratio is obtained from FIG. 19, and is equal to the ratio of the lowest counts (y-axis) obtained using HRP divided by the counts without HRP (horizontal lines): for Ag, S/N=7200/900 counts >8.

Figure 20:
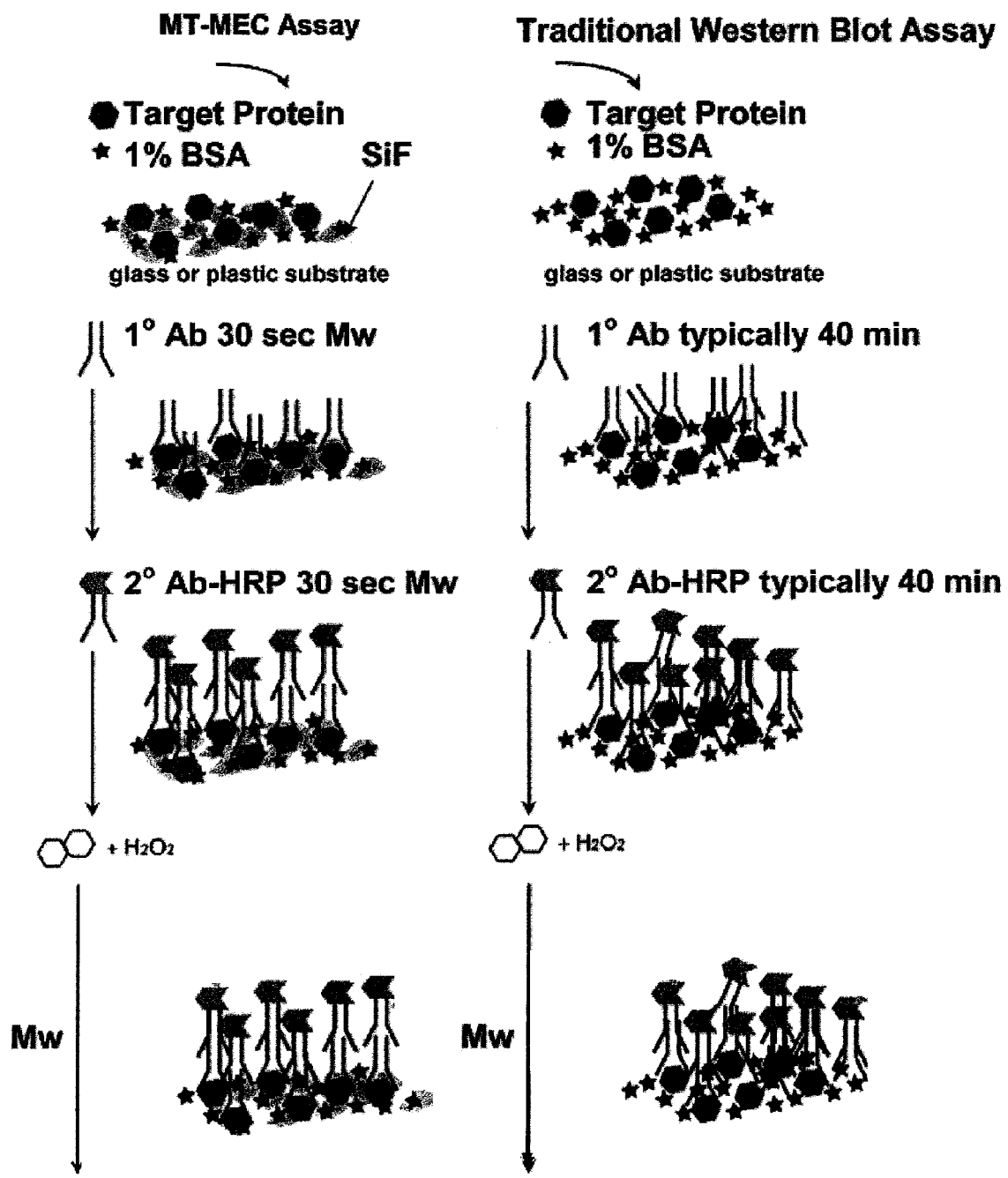
FIG. 20 shows the procedure for the MT-MEC immunoassay (Mw, low-power microwave heating).
Figure 20:
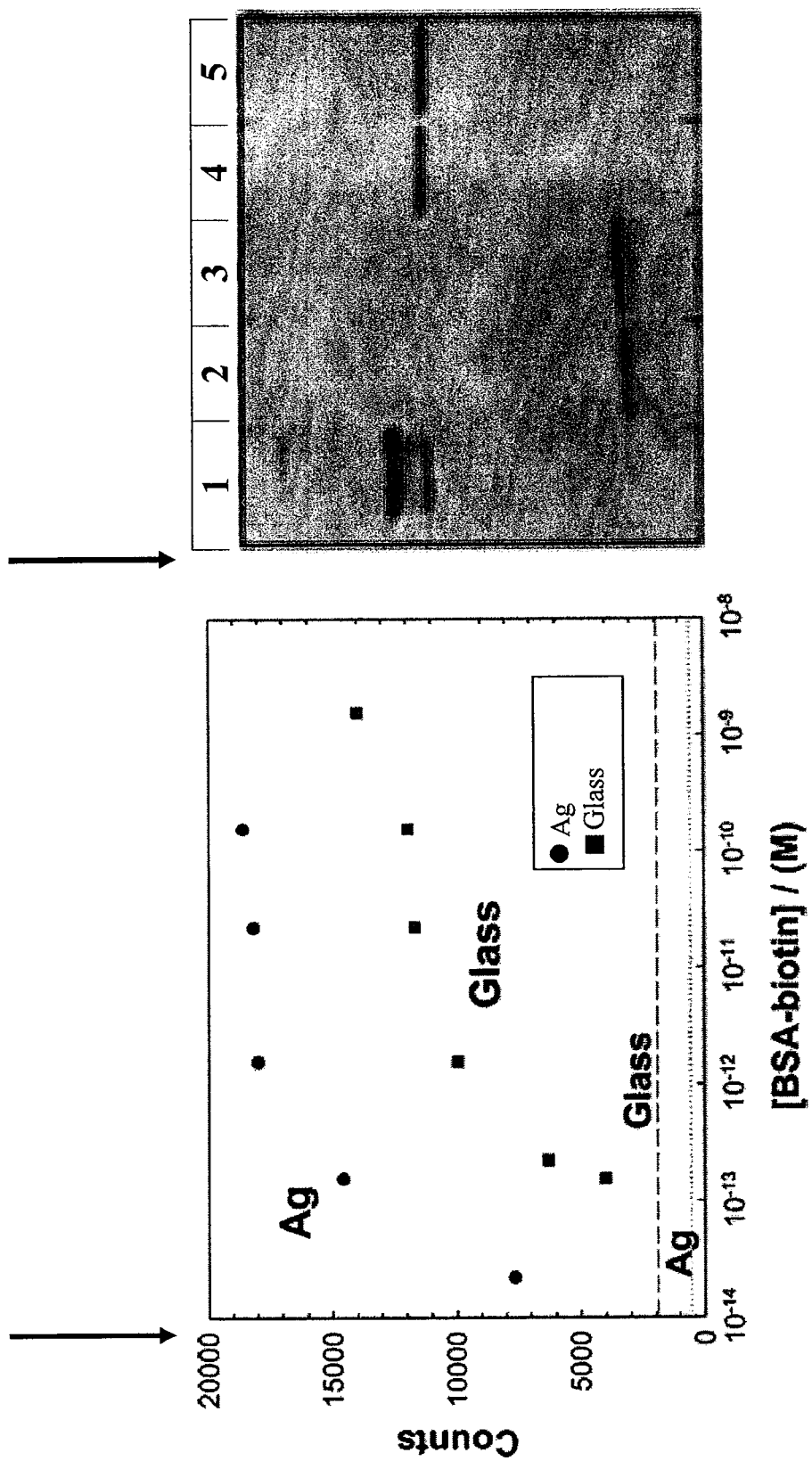

As compared to traditional western blot approaches, FIG. 20, MT-MEC offers protein quantification with ultrafast assay times, i.e., <2-min total assay time versus ~80 min.

3.8. Conclusions

Using low-power microwaves, it has been demonstrated as an inexpensive and simplistic approach to overcome some of the classical physical constraints imposed by current protein detection platforms, namely, assay rapidity, sensitivity, specificity, and accurate protein quantification. With the MT-MEC approach, the sensitivity of detection (<0.5 pg) is 1 order of magnitude greater than that available with currently standard commercially available methodologies (i.e., ECL Plus Western Blotting Detection Kit, RPN2132, Amersham Biosciences). In addition to the improved detection sensitivity, it is demonstrated herein that that these assays can be performed in a fraction of the time (in fact, less than 1 min) typically required with standard methodologies. With the application of microwaves and the subsequent acceleration of the chemiluminescent reaction, the on-demand nature of light emission not only increases the detectability of low concentrations of proteins, but photon flux is also proportional to the concentration of the protein on a surface. Thus, for immunoassays in the clinical setting, the MT-MEC approach offers a potentially powerful approach to protein detection because it substantially decreases current assay times to minutes, potentially decreases false positives due to increased specificity, and increases assay sensitivity by at least 1 order of magnitude (see FIG. 19).

With the decreased reaction times, increased sensitivity, increased specificity, and signal enhancement achieved with MT-MEC, it is shown here a dramatically decreased the volume of reagents required to perform these assays. Thus, by using MT-MEC into standard protein detection methodologies, reagent waste and overall experimental costs will be decreased. Further, with this technology, both ultrafast and ultra bright chemiluminescence assays can be realized.

4. Microwave Focused Chemiluminescence

4.1 Materials

Bovine-biotinamidocaproyl-labeled albumin (biotinlyated BSA), HRP-labeled avidin, 99.999% aluminum evaporation slugs, and premium quality APS-coated glass slides (75×25 mm) were obtained from Sigma-Aldrich. CoverWell imaging chamber gaskets with adhesive (2.5 mm diameter, 2 mm deep and 5 mm diameter, 2 mm deep for temperature measurements) were obtained from Molecular Probes (Eugene, Oreg.). Steptavidin-HRP prediluted solution (Catalog No. 20774) was obtained from Chemicon International Inc. Chemiluminescence reagents for these experiments were purchased from Amersham Biosciences (ECL Plus Western blotting detection kit, RPN2132).

The commercially available glow sticks contain the necessary reacting chemicals, which are enclosed within a plastic tube, and yield a bright chemiluminescent emission when they are physically altered. The plastic tube contains a phenyl oxalate ester, a fluorescent probe, and a glass capsule containing the activating agent (hydrogen peroxide). Activation of the chemicals is accomplished with a bend, a snap, and a vigorous shake of the plastic tube which breaks the glass capsule containing the peroxide and mixes the chemicals to begin the chemiluminescence reaction. Commercially available chemiluminescence materials were purchased and used to demonstrate the utility of the inexpensive microwave reactors.

The ECL Western Blotting Detection Kit contained two solutions of reacting chemicals that yield a bright chemiluminescent emission at 430 nm upon mixing. Solutions were mixed as described in previous reports.[40, 41]

FDTD (Finite difference Time Domain) software was purchased from Lumerical Solutions, Inc., to solve Maxwell's equations for structures that have complex geometries or widely varying electromagnetic material properties for a wide variety of microwave field sources. With this software package, time domain information can be recorded at any spatial point (or group of points) and the frequency domain information at any point (or group of points). Simulations were run on a Dell 690 workstation that is equipped with two 2.66-GHz, 64-bit Dual-Core Intel Xeon 5150 series processors for a total of four execution cores in two sockets and 8 GB of RAM.

Figure 30:
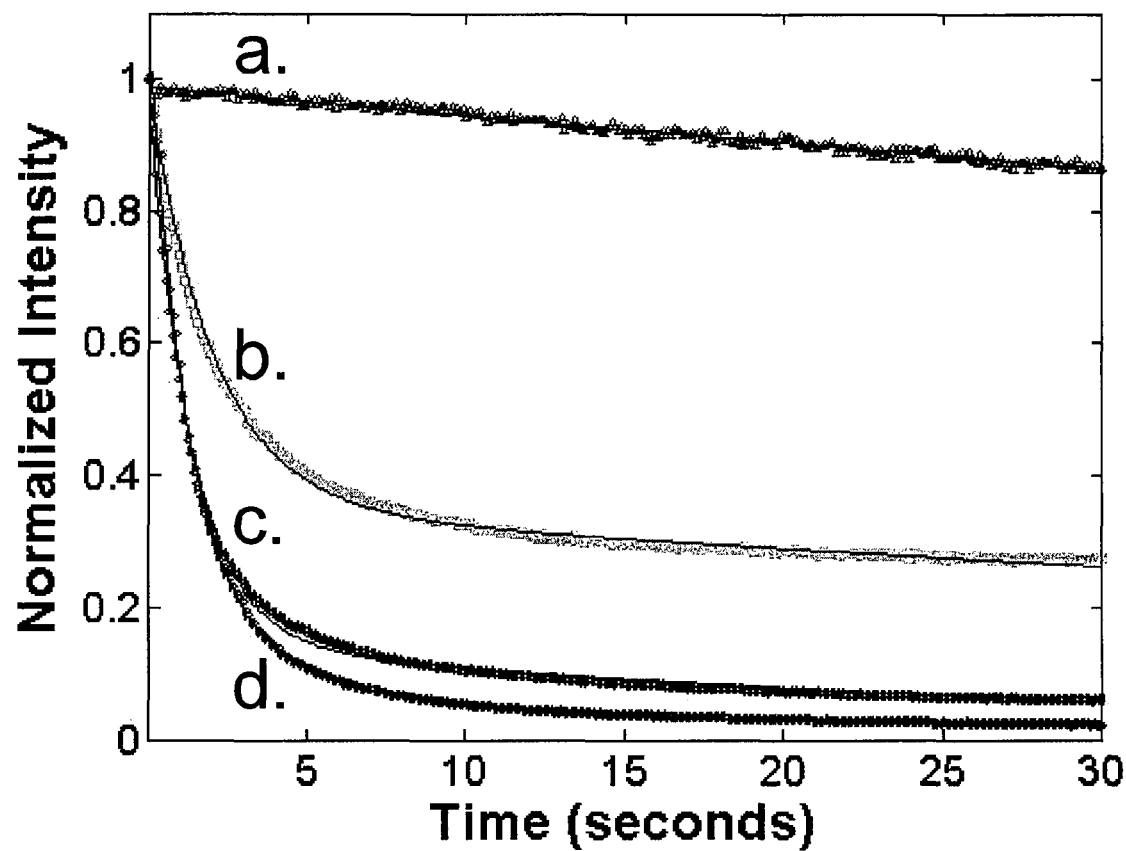
FIG. 30 shows normalized intensity decay curves for chemiluminescence signal after 5 second low power microwave exposure for (a) center of Al triangle; (b) glass substrate; (c) tip of aluminum triangle and (d) in the 1 mm gap of the 'bow-tie' geometry. Reaction decay rates were fit to a multi-exponential decay model, $$I(t) = \sum_i A_i e^{-k_i t}.$$

To establish that the spatial distributions of the fields in the xy-plane of the 2D images adequately approximate the spatial field distributions in the xy-plane for convergent three-dimensional simulations of similar structures (FIGS. 30 and 31), 3D simulations of the single triangle and disjointed 'bow-tie' geometries were performed. To avoid excessive computational times, the aspect ratio of the triangle geometry was decreased such that the equilateral triangle geometries were 5 mm long and 100 □m thick. To insure that the intensities for the images converged the mesh size was decreased in the xy and z dimensions from 0.16 mm and 0.025 mm to 0.4 mm and 0.01 mm at three intervals of 0.04 mm and 0.005 mm, respectively. Two equilateral 5 mm triangle were modeled by creating a second equilateral triangle structure and aligning its apex with the tip of the mirror triangle, such that the tips are separated by a gap distance, D. Optical properties of triangle structures were defined as perfect conductors. Thus, the total complex permittivity of a perfect conducting metal, such as aluminum, in the presence of a microwave field is given by $$\tilde{\varepsilon}(f) = \varepsilon_{REAL} + i\varepsilon_{IMAG}\frac{f_{SIM}}{f} + i\frac{\sigma}{2\pi \cdot f\varepsilon_o} \quad (4)$$

where $\varepsilon_{REAL}$ is the real part of the permittivity for the dielectric medium, $\varepsilon_{IMAG}$ is the imaginary of the dielectric medium, $f_{SIM}$ is the center frequency of all the sources in the simulation, f is the frequency of the simulation, $\varepsilon_o$ is the permittivity of free space, and σ is the conductivity of the metal. The conductivity value of the metal is approximated to be close to the d.c. value for aluminum, $3.8 \times 10^7 Sm^{-1}$, the background dielectric media is presumed to be air, and the frequency, f, is set to 2.45 GHz.

The microwave cavity source used in these experiments was a standard microwave oven that is equipped with a magnetron placed on the outside of the cavity, which is treated with white reflective coating to optimize microwave confinement, standing wave generation, and minimize absorption loss. The microwave system was modeled as a total field scattered electric field (TFSF) to best approximate the electromagnetic field in the microwave cavity during operation and assumed only $TE_{10}$ modes could propagate in the microwave cavity.[45] Subsequently, electromagnetic radiation is modeled to propagate from left to right along the x-axis across equilateral triangle(s) structures.

Since visualizing the xy spatial field distributions for the chosen planar geometries was of interest and not the absolute intensities, it was chosen to model the planar geometries in two dimensions as an infinite column and ignore the scattering effect in the z-plane. Thus, the results of 2D FDTD simulations was shown to demonstrate the relative electric field distributions for the planar geometries.[46] While it is understood that these simulations will not divulge absolute intensity enhancements, the resultant, normalized field distributions for the simulations are a useful tool to predict the expected field distributions in the xy-plane for our experimental configuration.

For 2D triangle simulations, mesh sizes were set at 0.1 mm for one triangle and disjointed 'bow-tie' simulations. The simulation time is set to 10 ns to insure that the light travels down the surface and back. The absorbing boundary conditions are of the perfectly matched layer type and are used to truncate the FDTD domain in the x and y dimensions. Final images are normalized with respect to the maximum pixel total intensity ($E_x^2+E_x^2$) for the images.

4.2. Preparation of Glass Substrates Modified with Thin-Film Aluminum Triangles

Triangle masks were prepared by cutting shapes 12.3-mm equilateral triangles in aluminum sheets ~100 um thick with the appropriate geometry; i.e., "bow-tie" masks were prepared by removing two 12.3-mm triangle pieces of aluminum such that the triangle tips are separated by a 1-mm distance. Single triangles masks were prepared in a similar fashion. Silanized glass slides were wrapped with aluminum foil masks such that 75-nm aluminum films were deposited on the exposed area of the silanized glass slides by vapor deposition with BOC Edwards Auto 306 instrument. Upon completion, masks were removed and slides modified with aluminum triangle substrates were cut into ~1×1.5 in$^2$ rectangles.

4.3. Preparation of Glass, Paper, Plastic, and Nitrocellulose (NC) Substrates Modified with Thin-Film Aluminum Triangles Equilateral 12.3-mm triangle and 8-mm square geometries were constructed by cutting structures with a stencil and blade. Triangle or square pieces of aluminum sheets were affixed to glass, plastic, paper, and nitrocellulose substrate with the same geometry, 1.5 cm×1 cm. Disjointed bow-tie geometries were constructed from two inverted 12.3-mm triangles, such that the distance between the apexes or gap size was ~1 mm. Image wells were placed at the corners of the square geometries, at the center of the square geometries, at the tip of a single aluminum triangle, between two aluminum triangles, at the center of the aluminum triangle, and on the plain glass substrates and were subsequently filled with 6 uL of blue chemiluminescence material. Photographs of the sample geometries were taken before and after the application of low-power microwave pulses and intensity counts were subsequently collected for 150 s at 100-ms time intervals.

4.4. Chemiluminescence Reaction Assays

Upon activation of chemical reaction, 6 uL of solution placed in the imaging chambers affixed to the plain glass substrate (FIG. 22A-D). Following addition of the chemicals to the imaging chambers, each sample was subsequently placed in the microwave cavity and signal intensity was monitored for ~50 s. The samples were then exposed to a 5-s low-power microwave pulse (10% power), and the signal was again monitored for the duration of the pulse and a total of 50 s before the application of a second pulse. In total, three 5-s pulses were applied to the respective sample geometries at 50-s time intervals, and the signal intensity was measured at 100-ms intervals for 200 s. For coverslip detection, the experimental and detection conditions are repeated with the same procedure outlined above with the exception of the modified sample geometry (FIG. 23A).

Reaction progress for chemiluminescent solutions on different sample geometries is determined by measuring intensity signal at 100-ms time intervals, and results are plotted as $I_o/I$ ratios versus time (seconds), where $I_o$ is the intensity before microwave pulsing and I is the intensity during pulsing. Data are fit to single-exponential decays ($e^{-kt}$) and fits are shown as solid lines. The average of two experimental values is plotted with the difference shown by error bars.

4.5. Temperature Measurements and Arrhenius Plots

In order to estimate the relative temperature increases of the solutions on the surfaces with different sample geometries, an Arrhenius curve calibration was performed with preheated chemiluminescent solution. Chemiluminescent dye solution was heated in a boiling water bath, and 50 uL was subsequently removed from the heated solution and placed in an image chamber well on a preheated microscope slide. Intensity measurements were made and plotted with the corresponding sample temperatures that were measured with a temperature probe. The natural logarithm of the intensity was plotted versus the inverse of the temperature measurements and fit to the Arrhenius equations (inset, FIG. 23B) using Matlab's nonlinear least-squares optimization routine (inset, FIG. 23B). Using the resultant fitting equation, further points were extrapolated to determine the relative corresponding temperatures for higher intensity values (dashed extension line, FIG. 23B). Normalized intensities for microwave measurements were corrected according to precalibrated room-temperature data ($I_{19.40°}/I_o=0.90$).

4.6. Ru(by)$_2$Cl$_2$ Temperature Measurements

Figure 22:
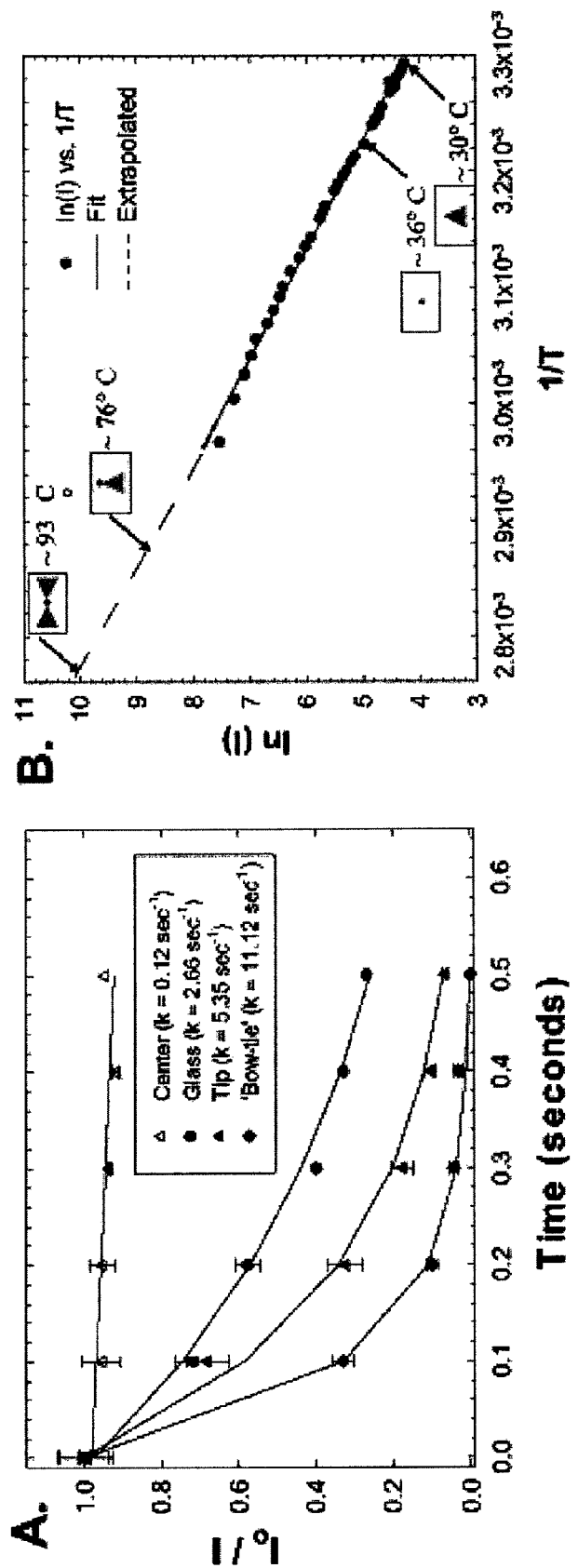
FIG. 22 shows (A) Reaction progress for chemiluminescent solutions on different sample geometries plotted as $I_o/I$ ratios versus time (seconds), where $I_o$ is the intensity before microwave pulsing and I is the intensity during pulsing. Data are fit to single-exponential decays ($e^{-kt}$), and fits are shown as solid lines. The average of two experimental values is plotted with the difference shown by error bars. (B) Arrhenius plot and fit for the chemiluminescence reaction on glass slides and the estimated temperature increase for the different sample geometries after exposure to low-power microwave pulses. Sample geometries are shown (insets). (C) Upon application of 5-s, low-power, 2.45-GHz microwave pulses, the subsequent decrease in $Ru(by)_2Cl_2$ sample emission intensity (I) was measured and normalized with respect to the pre-Mw pulse intensity ($I_o$). Subsequently, the temperature values are determined from a precalibrated intensity vs temperature plot of a $Ru(by)_2Cl_2$ sample of the same concentration. Room temperature (RT) is noted and sample geometries are shown (insets). (D) Heating rates for $Ru(by)_2Cl_2$ solutions on different sample geometries are plotted as temperature (° C.) versus time (seconds). Data are linearly fit according to $T=(dT/d\tau)\tau+1$, and fits are shown as solid lines. The average of two experimental values is plotted.
Figure 22:
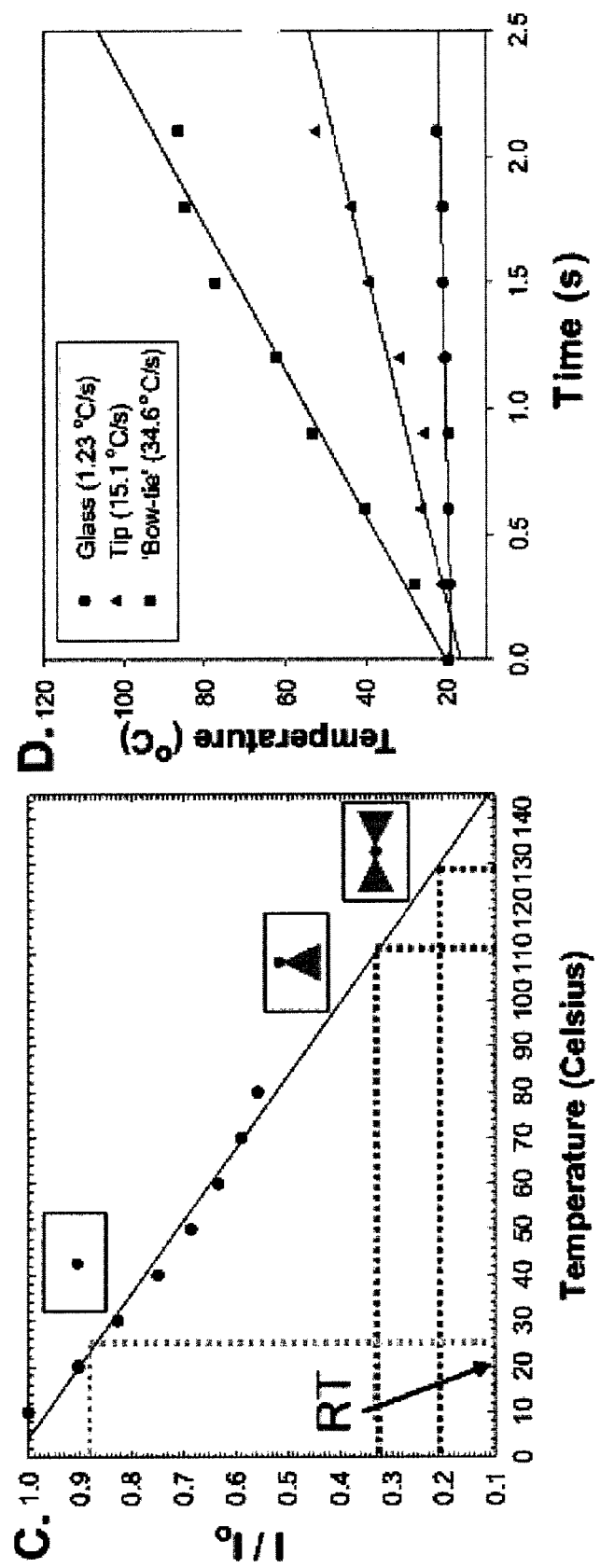

In order to estimate the relative temperature increases of the solutions on the surfaces with different sample geometries, the intensity of fluorescence emission was measured from 0.1 uM aqueous solutions of Ru(by)$_2$Cl$_2$ on glass substrates in the presence and absence of the planar metallic single triangle and bow-tie geometries.[47] Ru(by)$_2$Cl$_2$ aqueous solutions were excited with a 473-nm laser source, and the resulting emission intensity was monitored at 300-ms time intervals. Upon application of a 5-s, low-power, 2.45-GHz microwave pulses, the maximum decrease in fluorescence intensity from the Ru(by)$_2$Cl$_2$ aqueous solutions was recorded and normalized with respect to the room temperature (pre-Mw pulse) emission intensity. Subsequently, the corresponding temperature values were determined from a precalibrated intensity versus temperature plot of a Ru(by)$_2$Cl$_2$ sample of the same concentration using a Cary Eclipse fluorescence spectrometer with temperature controller. Calibration temperatures were 10, 20, 30, 40, 50, 60, and 70° C. Heating rates for Ru(by)$_2$Cl$_2$ samples on different sample geometries were determined by measuring fluorescent intensity from solutions at 300-ms time intervals. Data are corrected for room-temperature measurements from precalibrated Ru(by)$_2$Cl$_2$ intensity data. Data are linearly fit according to $T=(dT/d\tau)\tau+1$ using Matlab's nonlinear least-squares optimization routine, and fits are shown as solid lines. The average of two experimental values is plotted (FIG. 22 C, D).

4.7. Preparation of the Model Protein Assay (Biotin-Streptavidin) on Glass Coverslips The model assay is based on the well-known interactions of biotin and avidin. Biotin groups are introduced to the glass coverslips (No. 1) through biotinylated BSA, which readily forms a monolayer on the surfaces of glass.[48,49] Glass coverslips were cleaned with dilute solutions of detergent, soaked in concentrated nitric acid, rinsed with deionized, distilled water, and plasma cleaned for 30 s. Coverslips were incubated with 50 uL of 1 uM biotinylated BSA solutions for ~1 h. Coverslips were washed with water to remove the unbound material. Coverslips were then incubated with 50 uL of 1.5% aqueous BSA (w/v) for 1 h to minimize nonspecific binding of HRP-streptavidin to surfaces. Coverslips were again washed with water to remove excess BSA blocking solution. BSA-biotin functionalized coverslips were incubated with 50 uL of 1 uM HRP-streptavidin and were typically microwaved for 20 s in the microwave cavity (0.7 ft$^3$, GE compact microwave model JES735BF, maximum power 700 W). Control coverslips were incubated with only 1.5% BSA solutions and subsequently incubated with 50 uL of 1 uM HRP-streptavidin and exposed to low-power microwave pulsing for 20 s.[50] In all the experiments performed with low-power microwaves, there was no evidence of surface drying. Following incubation, imaging chambers were again washed with water to remove unbound HRP-streptavidin material prior to the chemiluminescence experiments. Imaging chambers were then affixed over incubation area prior to the addition of chemiluminescence experiments.

4.8. Chemiluminescence from Reagents on HRP-Functionalized Glass Coverslips

In order to obtain the same initial chemiluminescence emission for all measurements, all chemiluminescent assays were undertaken by combining 40 uL of solution A (peroxide mixture from ECL Plus Detection Kit Reagents) with 2.0 uL of solution B (acridan mixture from ECL Plus Detection Kit Reagents), incubated for 5 min, and then added to the imaging chambers. The final sample geometry is the HRP-functionalized coverslip with an imaging chamber filled with chemiluminescence solution. The coverslip is then placed on the top of glass substrates, whereby the center of the imaging chamber is positioned proximal to triangle structures, if present. (see sample geometry, FIG. 23A). Data collection commenced immediately following the addition of the reagents to the imaging chambers. The chemiluminescence signal was over 1-s discrete time intervals for 350 s before, during, and after microwave heating inside the microwave cavity (0.7 ft$^3$, GE compact microwave model JES735BF, maximum power 700 W). Microwave acceleration was achieved by applying four 10-s microwave pulses at 50-s time intervals. Data collection was terminated after 350 s.

Figure 21:
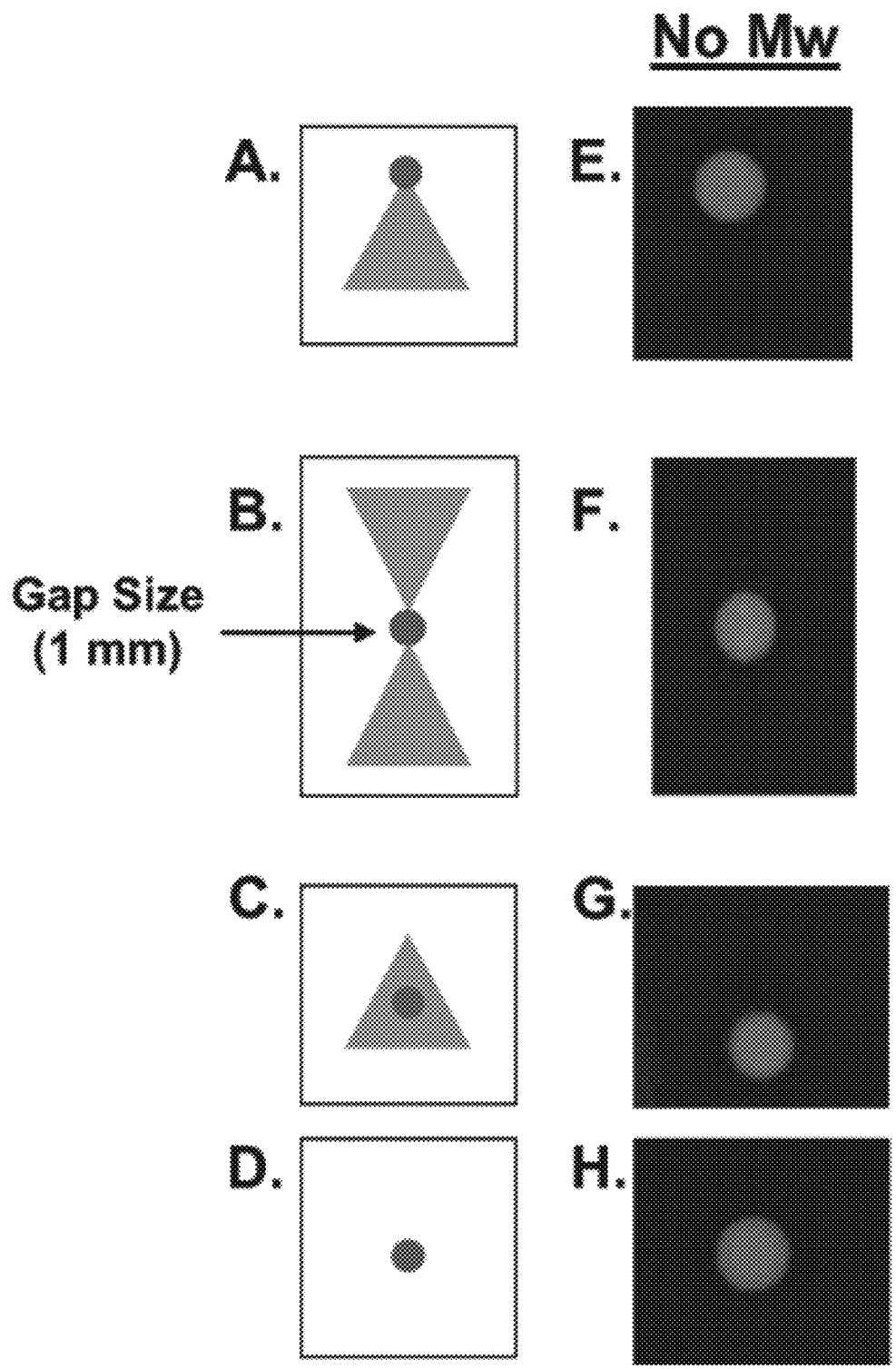
FIG. 21 shows (A-D) sample geometry depicting the chemiluminescence sample (circle), glass substrate (square), and aluminum triangle geometries (12.3-mm length; 1-mm gap size for disjointed bow-tie geometry); (E-H) before the application of a low-power microwave pulse (no Mw), the chemiluminescence signal is approximately equivalent for all sample geometries; (I, J) simulated intensity ($I_x+I_y$) images for a TE polarized 2.45-GHz total field scattered field source incident upon a 3D 12.3-mm equilateral triangle (left) and 3D disjointed bow-tie geometry with a gap size (arrow) of 1 mm (right) 100 um thick. The images shown are a xy plane cross section of the middle of the 3D simulated structure (z=0 um). (K-N) Upon application of low-power, 2.45-GHz microwave pulses (Mw), the experimental localized signal enhancement (triggered chemiluminescence) is shown.
Figure 21:
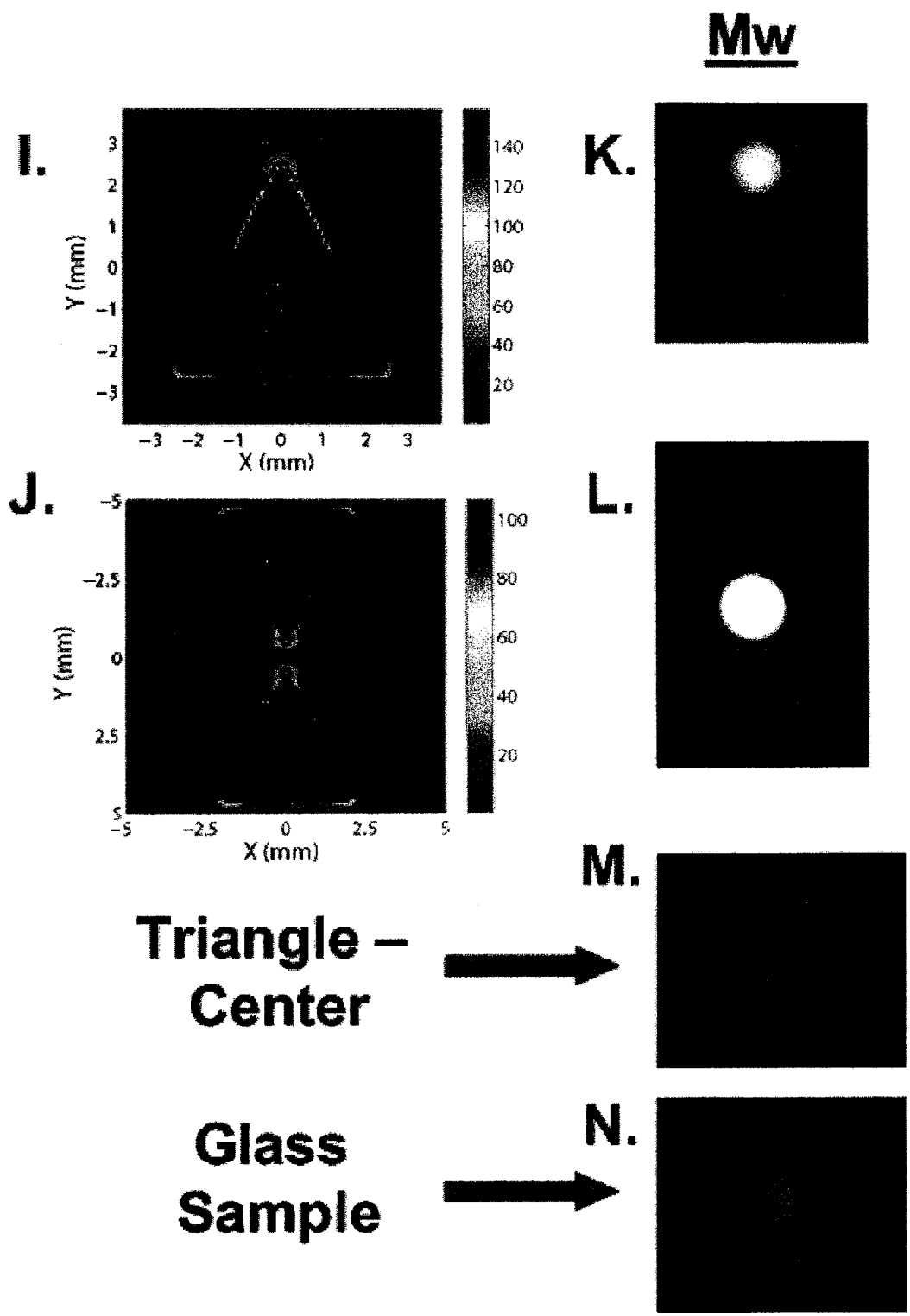

4.9. Chemiluminescence Reaction Assays from Glass, Paper, Plastic, and Nitrocellulose Substrates Modified with Disposable Aluminum Triangle Structures Upon activation of chemical reaction, 6 uL of solution was added to the imaging chambers affixed to respective positions in proximity to single aluminum triangle, bow-tie, or square structures (FIG. 21, far left). Following addition of the chemicals to the imaging chambers, each sample was subsequently placed in the microwave cavity and signal intensity was monitored for ~150 s. For all chemically induced chemiluminescent experiments, glass, plastic, paper, and NC substrates were cut into equal-sized samples to minimize variations of the convective microwave heating that may arise due to variations in the size of the glass substrates. The samples were exposed to a 5-s, low-power microwave pulse (10% power), and the signal was again monitored for the duration of the pulse and a total of 50 s before the application of a second pulse. In total, three 5-s pulses were applied to the respective sample geometries at 50-s time intervals, and the signal intensity was measured at 100-ms intervals for 200 s. Reported intensity measurements represent the mean of the maximum intensity values recorded during the application of the microwave pulse.

Figure 27:
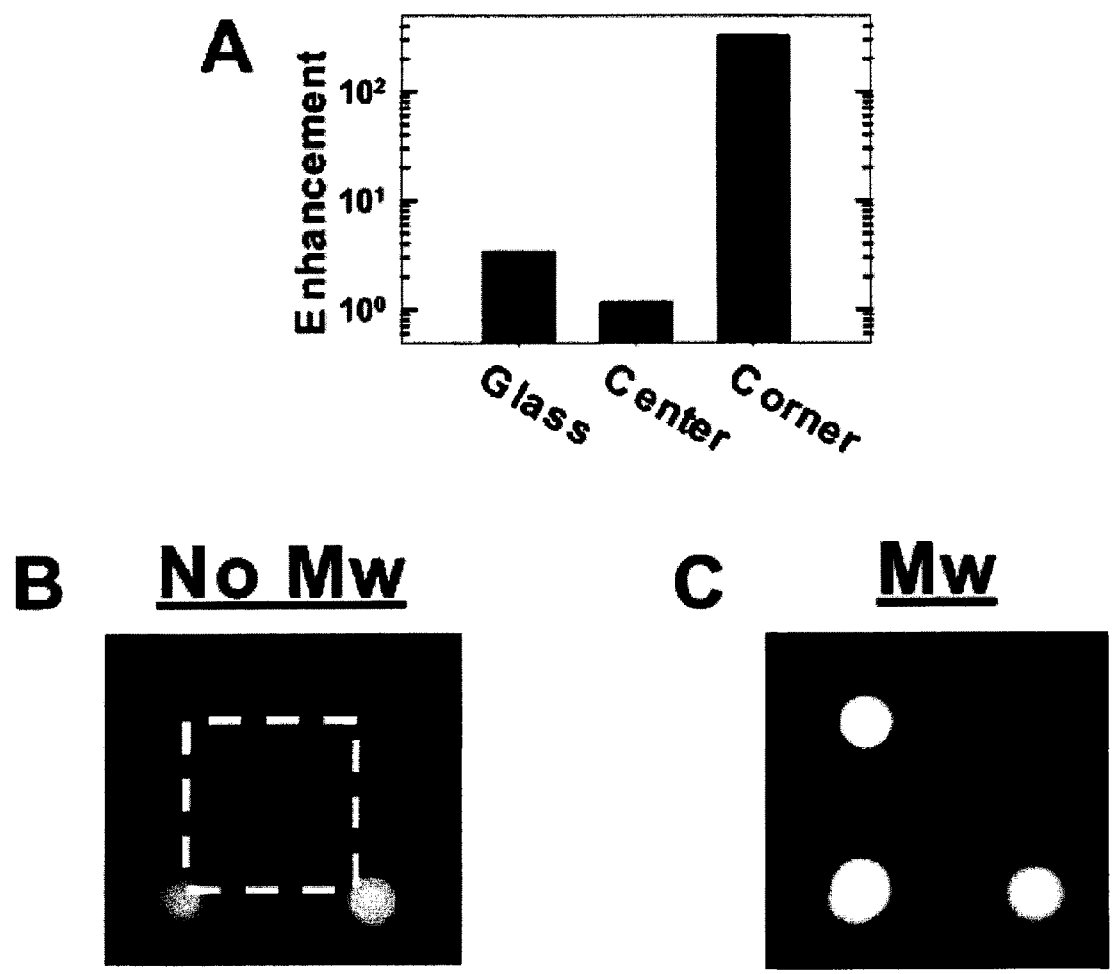
FIG. 27 show (A) Ratio of chemiluminescent intensities after Mw pulses to intensity before Mw pulses for glass, the center of the square geometry, and the corner. (B) Chemiluminescence signal in a multiplexed format is approximately equivalent from all positions on the 8-mm square aluminum foil structure (dashed box) before the application of low-power pulses and (C) significantly enhanced after the application of low-power microwave pulses.

For multiplexed assay experiments, 6-uL samples of four different colored chemiluminescent (green, red, blue, yellow) solutions were placed at the corners of an 8-mm aluminum foil square affixed to a glass substrate (FIG. 27). Prior to the application of a low-power microwave pulse, similar luminescent intensities were observed from the four samples. Upon the application of a 5-s, low-power microwave pulse (70 W), similar enhancements from the four chemiluminescent solutions were observed at the corners of the aluminum square.

4.10 Preparation of the Model Protein Assay on Nitrocellulose Membranes

PVDF membranes were obtained from Biorad and are considered a suitable substrate substitute for NC membranes. [51] Membranes were cut into 1-cm squares and were immersed in 100% methanol for a few seconds until translucent. Membranes were transferred to transfer buffer and incubated until equilibrated (2-3 min) Ten microliters of HRP dilutions was spotted on the center of the membrane to yield an approximately 100 ng, 10 ng, 1 ng, and 200 pg of protein. Control samples were prepared by spotting 10 uL of transfer buffer onto the membrane. Upon spotting the protein to the membranes, membranes were allowed to dry to completion. Round imaging chambers (~2 cm round) were affixed to glass slides, and dried membrane was placed at the center of the chamber.

4.11. Chemiluminescence from Reagents on Nitrocellulose Membranes with Immobilized HRP In order to obtain the same initial chemiluminescence emission for all measurements, all nitrocellulose chemiluminescent assays were undertaken by combining 80 uL of solution A (peroxide mixture from ECL Plus Detection Kit Reagents) with 2.0 uL of solution B (acridan mixture from ECL Plus Detection Kit Reagents), added to the imaging chambers, and incubated for 5 min. For membranes modified with triangle geometries, 12.3-mm aluminum foil triangle structures were affixed to the membrane at the perimeter of the HRP-spotted regions. Data collection commenced immediately following the addition of the reagents to the imaging chambers. The chemiluminescence signal was collected over 1-s discrete time intervals for 50 s before, during, and after microwave heating inside the microwave cavity (0.7 ft$^3$, GE compact microwave mode JES735BF, maximum power 700 W). Microwave acceleration was achieved by applying three 10-s microwave pulses at 50-s time intervals. Pulses were applied at 10% power. Data collection was terminated after 200 s.

4.12. Chemiluminescence Detection

Chemiluminescence spectra were collected using an Ocean Optics spectrometer, model HD 2000 (Dunedin, Fla.), connected to an Ocean Optics 1000-um-diameter fiber with an NA of 0.22. The fiber was positioned vertically on top of the slides containing the chemiluminescent reagents inside the microwave cavity. Chemiluminescent spectra and time-dependent emission intensities were collected with an integration time of 100 ms for ~200 s unless otherwise noted. For reactions performed directly on substrate surfaces (no coverslips, FIG. 21), signal intensities from reaction substrates with triangle, and bow-tie geometries were collected in the presence of a neutral density filter (ND 0.9). Resultant intensity values displayed in Table 1 for these two geometries were appropriately scaled (multiplication factor of ~8) to facilitate the direct comparisons of intensity measurements for all sample geometries. Integration time was kept constant between the control and silver island film sample measurements. The real-color photographs were taken with an Olympus digital camera (C-740, 3.2 Mega Pixel, 10× Optical Zoom) without the need for optical filters.

4.13. Reaction Rate Decays

Reaction rate decay curves for all samples were collected at a time interval of 100 milliseconds over an approximately 50 second time inteval. Reaction decay rates were fit to a multi-exponential decay model, $$I(t) = \sum_i A_i e^{-k_i t},$$

using Matlab's nonlinear least squares optimization routine where $k_i$ is the decay rate of component i and $A_i$ is its amplitude such that $$\sum_i A_i = 1.0.$$

The contribution of each component to the steady-state decay rate is given by $$f_i = \frac{A_i k_i}{\sum_i A_i k_i} \quad (5)$$

the mean decay rate is given by $$\bar{k} = \sum_i f_i k_i \quad (6)$$

and the amplitude weighted decay rate is given by $$\langle k \rangle = \sum_i A_i k_i. \quad (7)$$

Reaction decay results for all sample geometries are shown in Table 2.

4.14. Results

Figure 28:
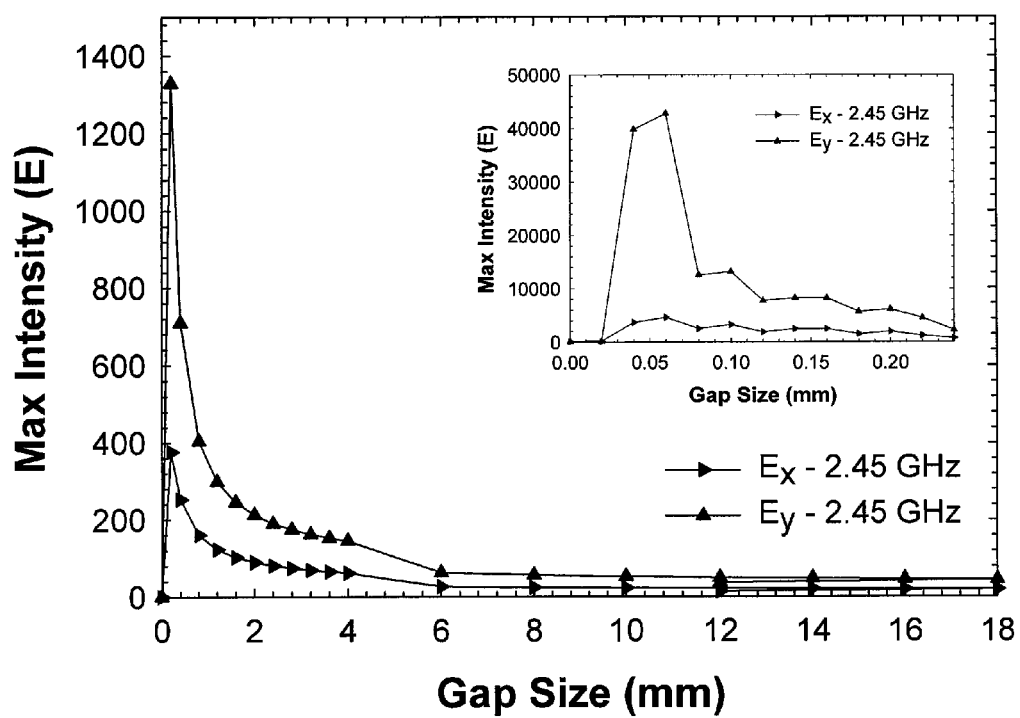
FIG. 28 shows maximum I $(I_x(E_y^2)+I_y(E_y^2))$ pixel intensity versus gap size for the 2 triangle configurations shown in FIG. 29. Inset, expanded view of maximum pixel intensity versus gap size.
Figure 29:
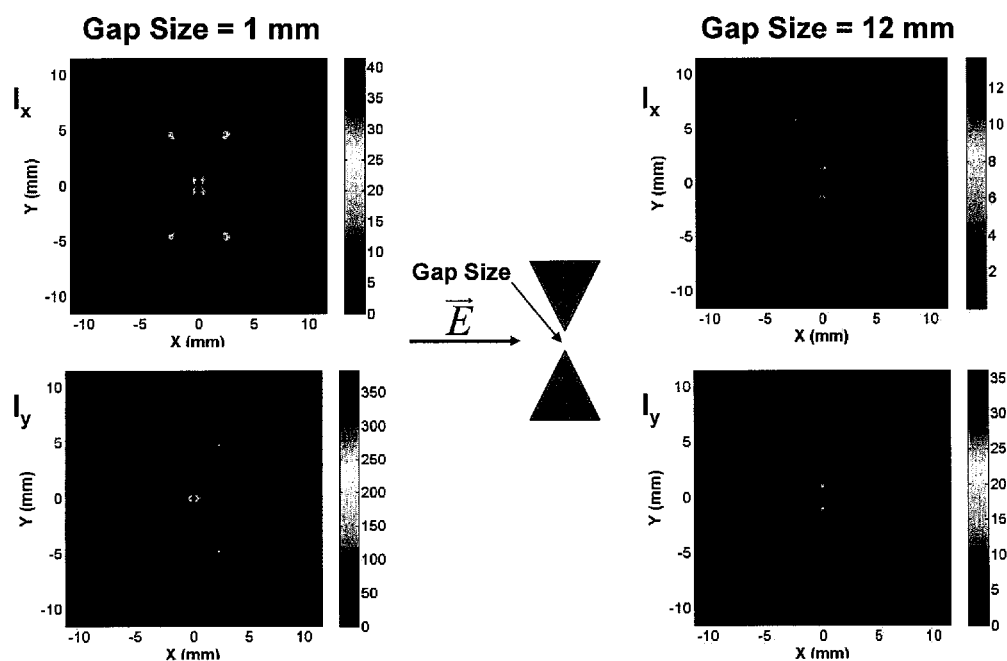
FIG. 29 shows simulated intensity images, $I_x$ (top) and $I_y$ (bottom) of the electromagnetic field distribution for 2.45 GHz microwave frequencies incident upon (2) 2-D equilateral triangles with 12.3 mm length and oriented with the sample geometry shown (middle). The incident field is held constant and the gap size is varied in subsequent simulations, 1 mm (left) and 12 mm (right) gap size examples are shown.

To design small inexpensive microwave structures that locally accelerate chemical reactions, FDTD simulation software was used to visualize electric field distributions for aluminum structures in a microwave field (FIG. 21 I, J). It was determined that the electric field distributions for a single aluminum 12.3-mm triangle structure (FIG. 21 I) 100 um thick (approximate thickness of the disposable aluminum structures described above) in a simulated 2.45-GHz total field scattered field (TFSF) that propagates from left to right. For a 2D cross section at the middle of the 3D structure (at z=0 um), intense field enhancements were observed proximal to the tips of the triangles and the maximum enhancement is observed at the triangle's apex (FIG. 21 I). Due to their simple design and single point focused electric field enhancements, bow-tie antenna geometries (two triangle geometries that are mirror images and joined at the apex) are commonly implemented to receive radio frequency transmissions. This structure was adapted to design a disjointed bow-tie configuration, such that the two triangles are separated by a gap distance, D, of 1 mm (FIG. 21 B). With this configuration, in theory, it is believed that the propagation of the 2.45-GHz microwave field (TFSF, TE-polarized) is short circuited across the metal surface, such that charge builds up in the gap of the bow-tie. The electric field intensity distribution ($E_x^2 + E_y^2$) of a 2D cross section (at z=0 um) for the disjointed bow-tie geometry with a 1-mm gap size is shown (FIG. 21 J). With this configuration, it was observed that the maximum field enhancement was localized at the gap between the two triangles. While additional gap sizes were simulated, 1-mm gap sizes were found to provide convergent solutions and substantial field enhancements, which diminish for larger gap sizes and lead to dielectric breakdown for smaller gaps, as shown in FIGS. 28 and 29.

In order to demonstrate that regions of maximum field enhancements for triangle and disjointed bow-tie geometries spatially correlate with regions of maximum chemiluminescent enhancements, 12.3-mm aluminum triangles of 75 nm thick were vapor deposited onto silanized glass microscope slides. For two triangle substrates, the gap sizes were set to be ~1 mm Glass and aluminum triangle-modified substrates were cut into equal sized samples to minimize variations of the convective microwave heating that may arise from variations in the size of the glass substrates. For bow-tie and triangle structures, image wells were affixed to the substrates, such that the tip of single triangle and junction of the bow-tie geometry were exposed to the solution in the well (FIG. 21 A, B). Wells on the respective sample geometries were subsequently filled with 6 uL of blue chemiluminescence material (FIG. 21 A-D, circles).

Photographs of each of the sample geometries before the application of low-power microwave pulses were taken and show that the pre-microwave intensities for each of the samples are approximately equivalent (FIG. 21 E-H). Samples were subsequently exposed to a short, low-power microwave pulse, and photographs of each of the sample geometries after the application of low-power microwave pulses were taken (FIG. 21 K-N). The spatial profile of the resultant chemiluminescent signal enhancements for the glass substrates modified with Al geometries (FIG. 21 K-N) correlate with regions of maximum field enhancements for simulated structures (FIG. 21 I, J). For glass surfaces modified with the aluminum triangle substrates, greater than 100-fold enhancement was observed in "on-demand" photon flux for the single triangle geometry and >500-fold enhancement for the bow-tie geometry, as shown in Table 1.

TABLE 1

| Substrate | Glass | Plastic | NC | Paper |
|---|---|---|---|---|
| no structure control | 3.4 (40, 135) | 5.2 (72, 377) | 5.6 (37, 209) | 8.7 (80, 700) |
| triangle, center | 1.4 (47, 68) | 1.14 (87, 100) | 1.5 (34, 53) | 1.4 (77, 110) |
| triangle, tip | 120 (58, 6925) | 256 (59, 15317) | 260 (38, 9760) | 81 (81, 6440) |
| triangle, 2 tips | 571 (50, 28970) | 580 (59, 34190) | 447 (56, 20230) | 395 (80, 31453) |
| square, center | 1.4 (101, 116) | | | |
| square, corner | 327 (107, 35000) | | | |

Tabulated Intensities before and after Microwave Exposure (value in ( )) and Subsequent Enhancements for Chemiluminescent Solutions, respectively on Glass, Paper, Nitrocellulose (NC), and Plastic Substrates Modified with Square, Triangle, or Disjointed "Bow-Tie" Sample Geometries For the chemiluminescence solution placed at the center of the triangle, almost no enhancement was observed in on-demand photon flux (Table 1), which is consistent with the absence of any electric field distribution in the simulated images at the center of the one triangle geometry (FIG. 21 I).

Since the signal intensities for all samples prior to microwave exposure are approximately equivalent (FIG. 21 E-H, Table 1), it is important to note that this lack of signal enhancement is not due to the quenching of the chemiluminescence emission. Furthermore, spectral shifts in chromophore emission are not observed after exposure to microwave pulses. Thus, it is concluded that the reported observations of intensity enhancements are not due to unsuspected changes in photophysical properties, including the destruction of the chromophores (data not shown).

To determine the corresponding increases in reaction rates of the chemiluminescent reactions during microwave pulsing for the different sample geometries, the inverse normalized intensities of the chemiluminescent solutions were plotted as a function of time. During the application of low-power, 5-s microwave pulses, the signal intensities were measured at 100-ms time intervals. Since intensity indicates the extent of reaction progress, $I_o/I$ versus time was plotted, where $I_o$ is the intensity before microwave pulsing and I is the intensity during pulsing (FIG. 22 A). The curves are fit to single-exponential decays ($I_o/I = e^{-kt}$) using a least-squares fitting algorithm to determine the reaction decay rates for the different sample geometries. While the reaction rates on the center of the triangle structures are indicative of the steady-state decays for chemiluminescent solutions at room temperature (0.12 $s^{-1}$), a 20-fold enhancement was shown for microwave-triggered chemiluminescent reaction rates on glass substrates (2.66 $s^{-1}$). In the presence of the aluminum structures, a 45- and 95-fold enhancements was reported for chemiluminescent reaction rates for the single triangle (5.35 $s^{-1}$) and bow-tie geometries (11.12 $s^{-1}$), respectively (FIG. 22 A).

The reaction decay rates was also recorded after the application of low-power. 5-s microwave pulses, as shown in Table 2.

sured intensity values of these samples correlate with significant temperature increases at the tip of a single aluminum triangle structure (76° C., FIG. 22 B inset) and in the gap of the disjointed bow tie geometry (93° C., FIG. 22 B inset). It is also noted that the temperature of the glass sample (36° C., FIG. 22 B inset) is higher than the temperature of the sample at the center of the triangle (30° C., FIG. 22 B inset).

To determine the corresponding changes in heating rates and final temperature of aqueous solutions for the different sample geometries, the intensity of fluorescence emission was recorded from aqueous solutions of $Ru(by)_2Cl_2$.[47] It is well-established that the intensity of the fluorescence emission from an aqueous solutions of $Ru(by)_2Cl_2$ is inversely proportional to the temperature of the solution. From precalibrated normalized intensity versus temperature plot of a $Ru(by)_2Cl_2$ sample of the same concentration that was fit to a linear function, $I/I_o=(dI/dT)T+1$, where $I_o$ is the intensity before microwave pulsing and I is the intensity during pulsing (FIG. 22 C).

From these results, the corresponding temperature increases were calculated for the different sample geometries at discrete time points to determine the relative heating rates, as shown in FIG. 22 D. In the absence of the aluminum triangle structures, the heating rate for the $Ru(by)_2Cl_2$ solution on glass was determined to be 1.23° C./s. In the presence of a single triangle structure, the heating rate is 15.1° C./s and the heating rate is more than doubled (34.6° C./s) in the presence of the bow-tie or two-triangle geometry. Although the final calculated temperatures for the triangle (~110° C.) and bow-tie (130° C.) geometries indicate that the aqueous solutions are superheated, it is important to note that these values are beyond the range of the linear dependence of the emission intensity of $Ru(by)_2Cl_2$ solutions. Thus, these values are only rough approximations of the final temperatures.

TABLE 2

| Sample: | $A_1$ | $k_1 (s^{-1})$ | $A_2$ | $k_2 (s^{-1})$ | $A_3$ | $k_3 (s^{-1})$ | $\bar{k}$ | $\langle k \rangle$ |
|---|---|---|---|---|---|---|---|---|
| Glass | 0.648 | 0.35 | 0.482 | $9.86 \times 10^{-2}$ | — | — | 0.306 | 0.274 |
| Al - Center | 1.00 | $4.45 \times 10^{-3}$ | — | — | — | — | $4.45 \times 10^{-3}$ | $4.45 \times 10^{-3}$ |
| Al - Tip | 0.851 | 0.73 | 0.149 | $3.22 \times 10^{-2}$ | — | — | 0.725 | 0.626 |
| Al - 2 Tips | 0.787 | 0.86 | 0.171 | 0.25 | 0.0420 | $2.75 \times 10^{-2}$ | 0.822 | 0.721 |

Chemiluminescence decay rates after 5 second exposure to low power microwaves. All data fit with $$I(t) = \sum_i A_i e^{-k_i t}.$$

Reaction decay rates were fit to a multiexponential decay model, $I(t)=\Sigma_i A_i e^{-k_i t}$, where $k_i$ is the decay rate of component i and $A_i$ is its amplitude such that $\Sigma_i A_i$ 1.0. After microwave pulsing, it was observed that the amplitude-weighted decay rates, $\langle k \rangle = \Sigma_i A_i$, are increased by >2-fold and almost 3-fold for the chemiluminescence samples at the tips of a single triangle, as shown in Table 2 and in FIG. 30 and the gap of the disjointed bow-tie geometries as shown in Table 2 and FIG. 30, respectively.

Figure 23:
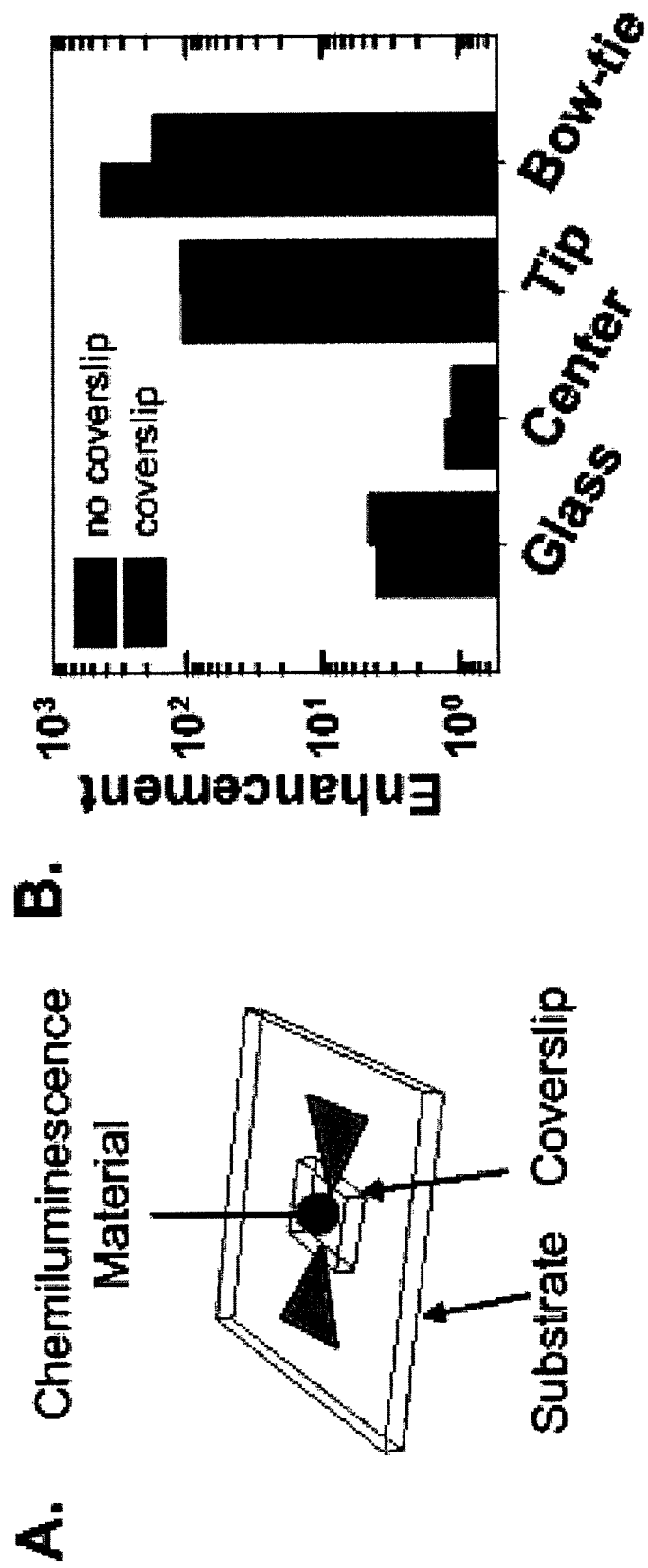
FIG. 23 shows (A) Coverslip chemiluminescence reaction geometry scheme. Imaging chambers are affixed to No. 1 coverslips and filled with 6 μL of chemiluminescent material (circle). Coverslips are positioned on plain glass substrates and glass substrates modified with aluminum triangle (12.3-mm length; 75 nm thick; 1 mm-gap size for two triangles geometry) geometries (insets, middle). (B) Enhancement is calculated from the ratio of chemiluminescence.
Figure 24:
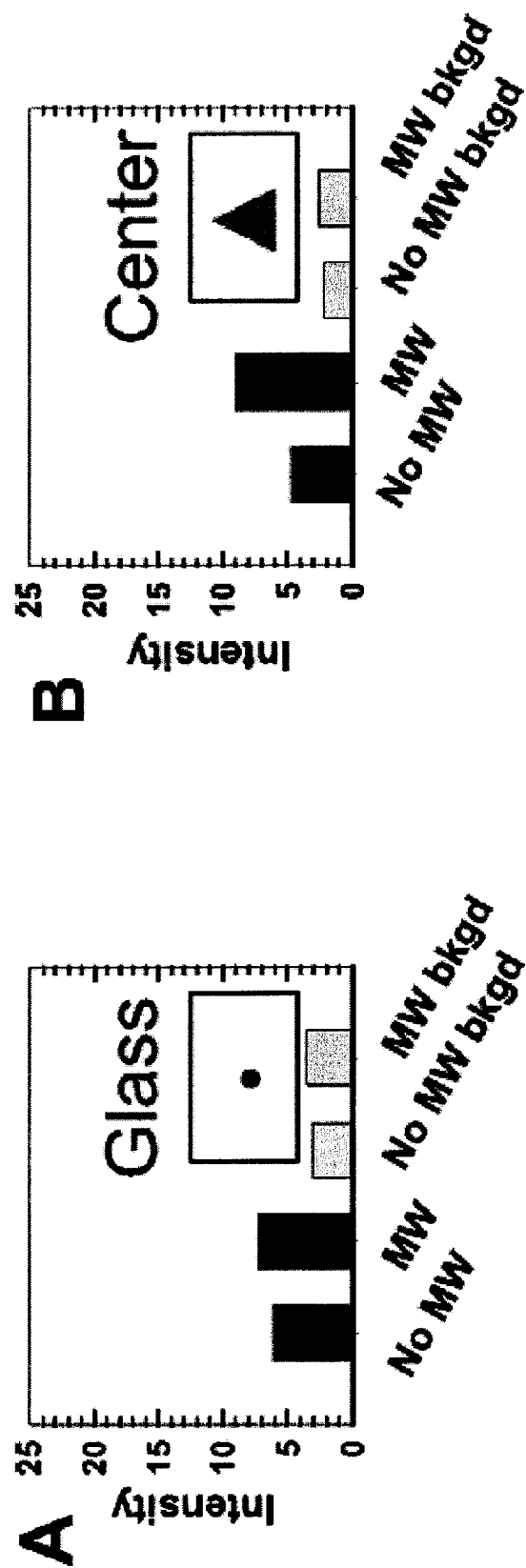
FIG. 24 shows (A-D) Chemiluminescence emission before (No MW bars) and after (MW bars) exposure to low-power microwave (Mw) pulses from glass coverslips incubated with 1 uM BSA-biotin and 1 uM HRP-streptavidin positioned on glass substrates modified with and without 12.3-cm Al triangle 75 nm thick (top 4 panels). Chemiluminescence emission before and after exposure to low-power microwave (Mw) pulses from control glass coverslips incubated with 1.5% BSA and 1 uM HRP-streptavidin (No MW Bkgd and MW bkgd columns bars) (E) Chemiluminescent microwave (Mw) enhancement ratios (Mw/no Mw) upon application of low-power microwave pulses (Mw) for different sample geometries.
Figure 24:
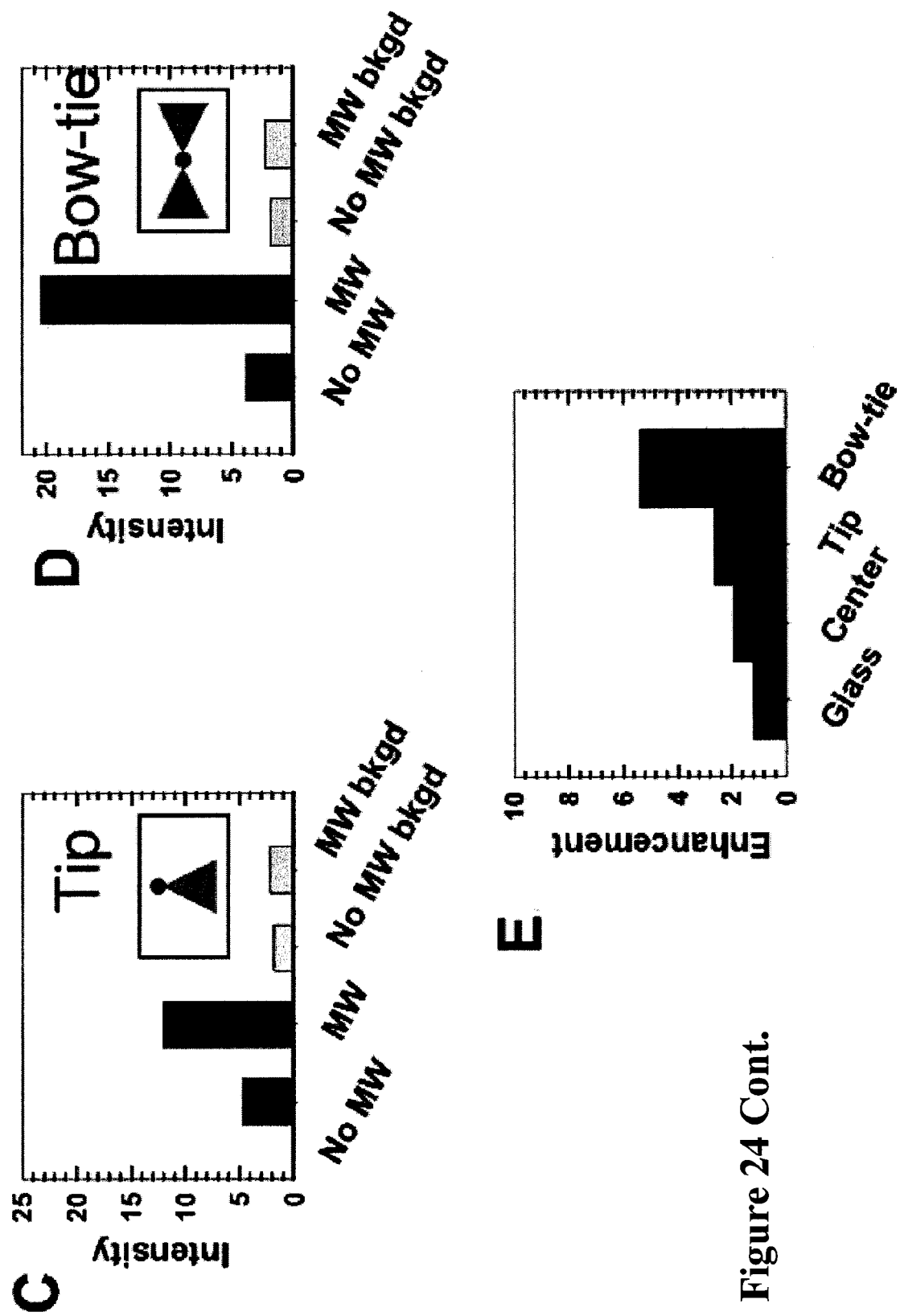
Figure 31:
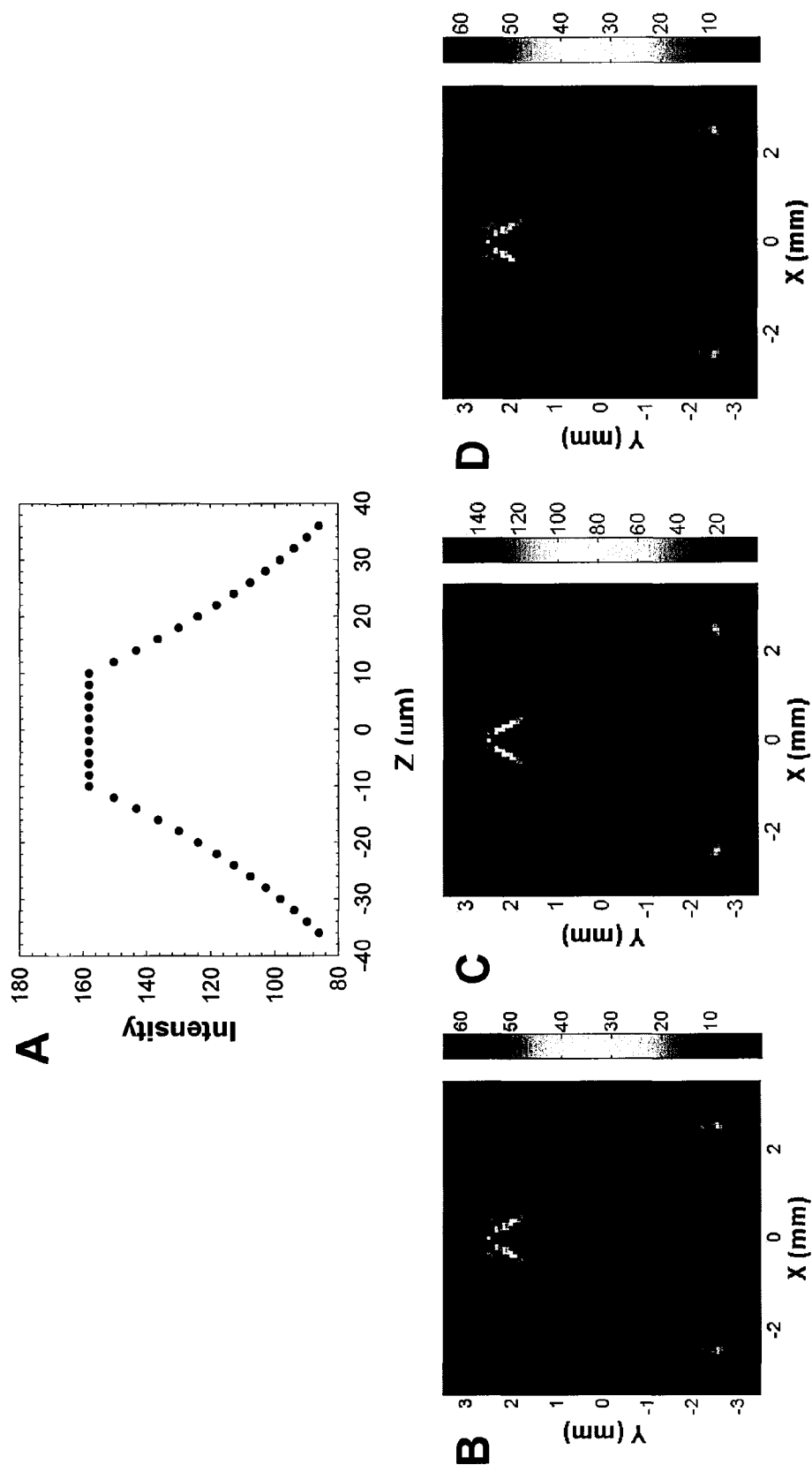
FIG. 31 shows (A) Simulated field intensity (Ix+Iy) distribution in the z plane for a TE polarized 2.45 GHz total field scattered field source incident upon a 3D 5 mm equilateral triangle 0.10 mm thick, whereby the x,y,z mesh sizes are 10, 10, and 2.5 um respectively. The triangle regions are modeled as perfect conductors and simulated images represent field distributions for cross sections in the z-plane at (B)-0.40, (C) 0, and (D) 40 um.
Figure 32:
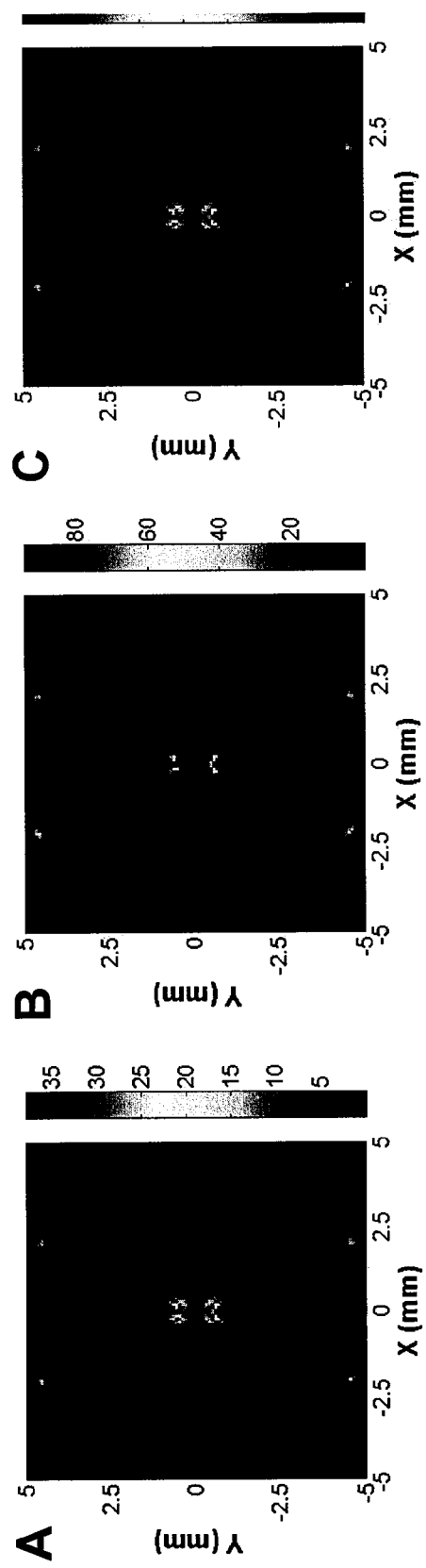
FIG. 32 shows simulated field intensity (Ix+Iy) distribution in the z plane for a TE polarized 2.45 GHz total field scattered field source incident upon a 3D disjointed 'bow-tie' geometry composed of (2) 5 mm equilateral triangles 0.10 mm thick with a 1 mm gap size, whereby the x,y,z mesh sizes are 10, 10, and 2.5 um respectively. The triangle regions are modeled as perfect conductors and simulated images represent field distributions for cross sections in the z-plane at (A)-0.40, (B) 0, and (C) 40 um.

To estimate the relative temperature increases of the chemiluminescent solutions on the surfaces with different sample geometries, an Arrhenius calibration curve was constructed using a preheated chemiluminescent solution. The natural logarithm of the intensity was plotted versus the inverse of the temperature measurements and fit to the Arrhenius equation (inset, FIG. 22 B). Using the fitting function, further points were extrapolated to determine the relative corresponding temperatures for higher signal intensity values (dashed extension line, FIG. 22 B). It is noted that the measured Since three-dimensional FDTD simulation data of the triangle geometries, as shown in FIGS. 31 and 32, show that the enhanced field also persists in the z dimension, i.e., vertically, imaging chambers were affixed to No. 1 coverslips (Corning Labware & Equipment) and added 6 uL of chemiluminescent solution. The imaging chamber and solution on top of the coverslip were placed on the top of glass substrates, whereby the center of the imaging chamber was positioned proximal to triangle structures, if present, as shown in FIG. 23 A. The samples were again exposed to short, low-power microwave pulses. With the coverslip sample geometries the same trend was observed for increases in on-demand photon flux that was documented for the reactions that were placed directly on the modified metal substrates, as shown in FIG. 21 K-N. In order to compare signal enhancements for the two sample geometries, the ratio of the signal after microwave pulsing to signal before microwave pulsing was calculated and compared the relative signal enhancement ratios, as shown in FIG. 23 B. It was observed that the presence of the coverslip did result in minor signal enhancement loss for the bow-tie geometry (~2-fold). Although great strides were taken to position the coverslip samples exactly at the center of the triangle tips such that the position of the samples placed directly on the substrates was reproduced, it is also possible that some signal loss could be due in part to the variance in position of the coverslip over the triangle tips, as well as the decrease in the electric field intensity above the sample surface. With the observation that enhancements could be created on coverslips placed above the sample geometries, the utility of this result was demonstrated. Coverslips were incubated with a 1 uM BSA-biotin solution and subsequently incubated the functionalized coverslips with HRP-streptavidin to create a model protein detection assay. Acridan/peroxide mixture was subsequently added to the imaging well affixed to the functionalized coverslip to simulate a typical HTS well format. Without microwave heating, a weak, steady "slow glow" chemiluminescent intensity was observed due to the presence of BSA-biotin/HRP-streptavidin complexes, as shown in FIG. 24 A. Due to the 1-s integration times and the limited detection sensitivity of the system, the weak signal is characteristic of the photon flux from a HRP-triggered chemiluminescent reactions. The limited detection sensitivity was due to the use a 300 □m fiber which only affords the collection of less than 0.2% of the total emitted light, a relative comparison inbetween the standard detection method and 'triggered' methods was still possible. More importantly, similar pre-microwave intensities were observed for the coverslip samples on the different sample geometries, as shown in FIG. 24 A-D (No MW Bkgd and MW bkgd columns). Thus, it can be deduced that the relative surface HRP concentrations for each of the samples is approximately equivalent and subsequent intensity enhancements are due to the exposure to microwave fields, not varying surface HRP concentrations. In addition, it was shown that the control samples (surfaces modified with 1.5% BSA and HRP-streptavidin) show no initial intensity counts, as viewed in FIG. 24 A-D (No MW Bkgd and MW bkgd columns).

Figure 33:
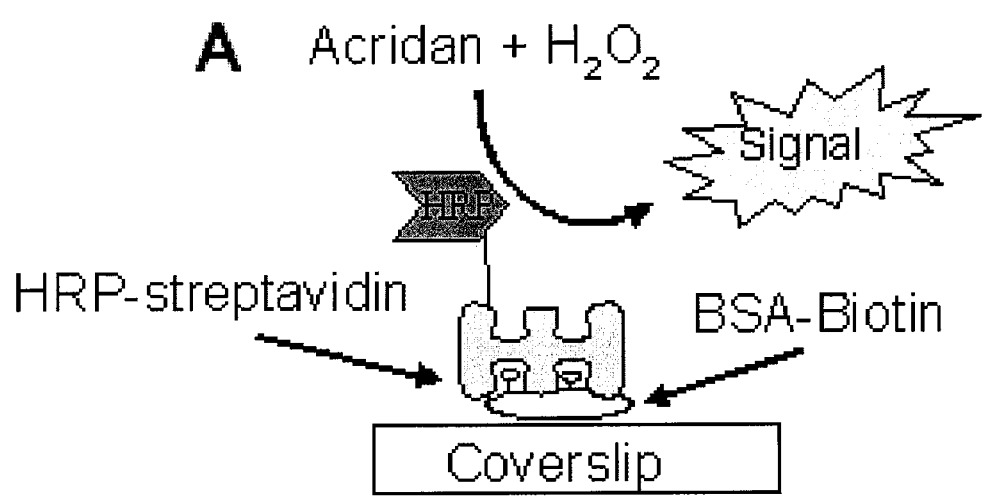
FIG. 33 shows (A) Model BSA-biotin, HRP-streptavidin chemiluminescent assay scheme. (B) Acridan chemiluminescence emission as a function of time from HRP modified glass coverslips coated treated with 1 uM BSA-biotin and 1 uM HRP-streptavidin and positioned glass substrate geometries with and without 12.3 cm Al triangle 75 nm thick (left). (C) Acridan chemiluminescence background emission as a function of time for glass coverslips incubated with 1.5% BSA and 1 uM HRP-streptavidin (control) positioned on glass substrate geometries with and without 12.3 cm Al triangle 75 nm thick shapes (right). All samples were exposed to four 10 second microwave pulses (Mw pulse) at 10% power.
Figure 33:
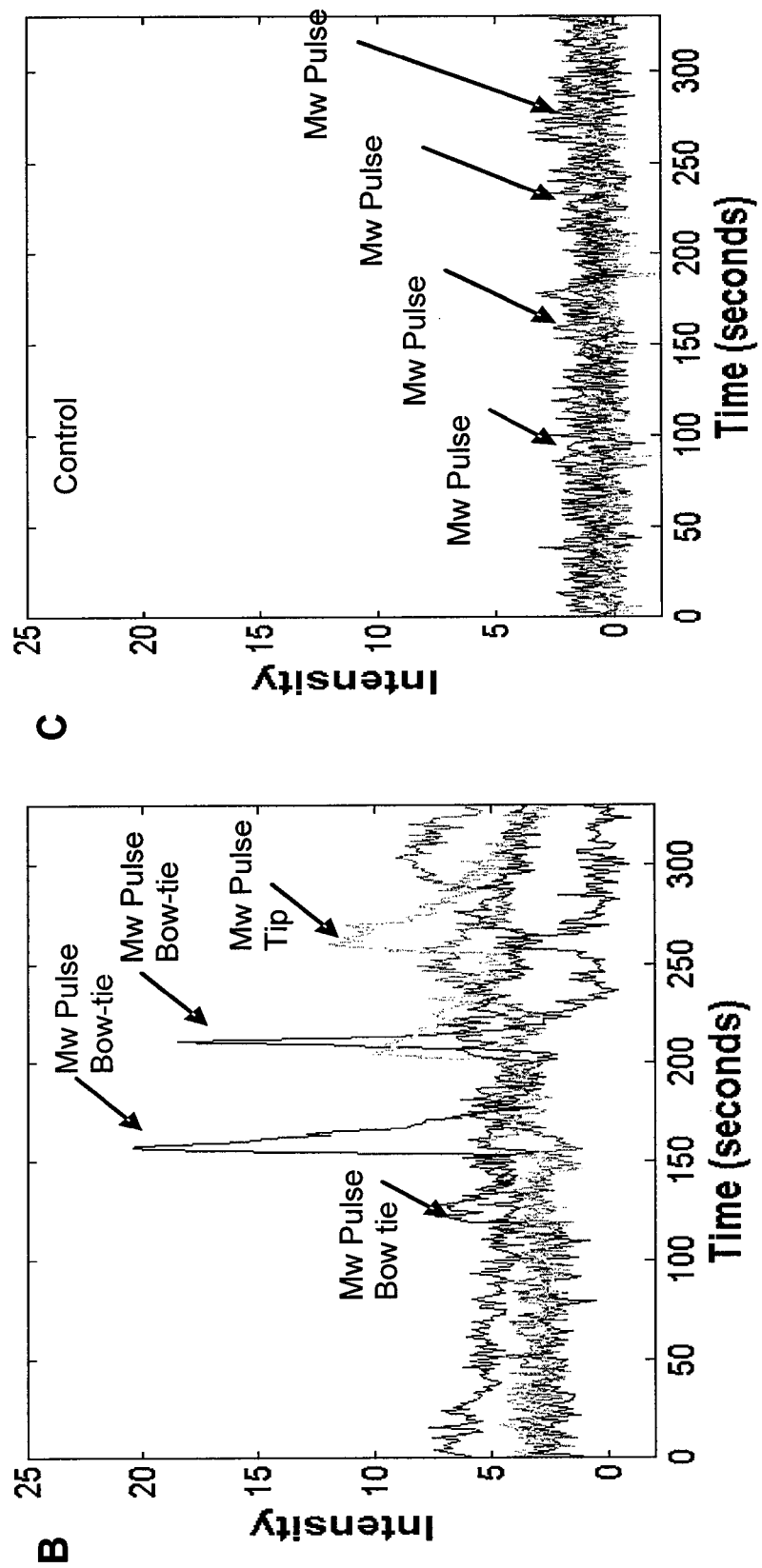

To demonstrate the benefits of microwave heating to increase the detected chemiluminescent signal from the surface assays, the photon flux was monitored (in counts) which is the area under the curve of the intensity-time plot, as shown in FIG. 33 cont. The photon flux indicates the extent of the HRP-catalyzed reaction and thus provides information about the presence of surface-bound BSA. The triggered "peaks" seen after each microwave exposure, FIG. 33 cont. are due to the application of the low-power microwave magnetron pulse. During the 10-s microwave exposures, the chemiluminescent intensity is triggered by the magnetron pulsing and the localized heating of the microwaves. It is clear from the signal intensity time traces. As shown in FIG. 33 cont. and the and the histogram plots (FIG. 24 A-D, MW bars) that the maximum photon flux was generated from the disjointed bow tie geometry samples. The microwave pulses were also applied to control samples, and no intensity enhancements are evident in the absence of BSA-biotin/HRP-streptavidin complexes. In comparison to the sample that was placed on the glass substrate alone, a significant signal-to-noise benefit from the modified sample substrates was shown and it was shown that the chemiluminescence reaction can be uniquely locally trigger to occur on demand.

Figure 25:
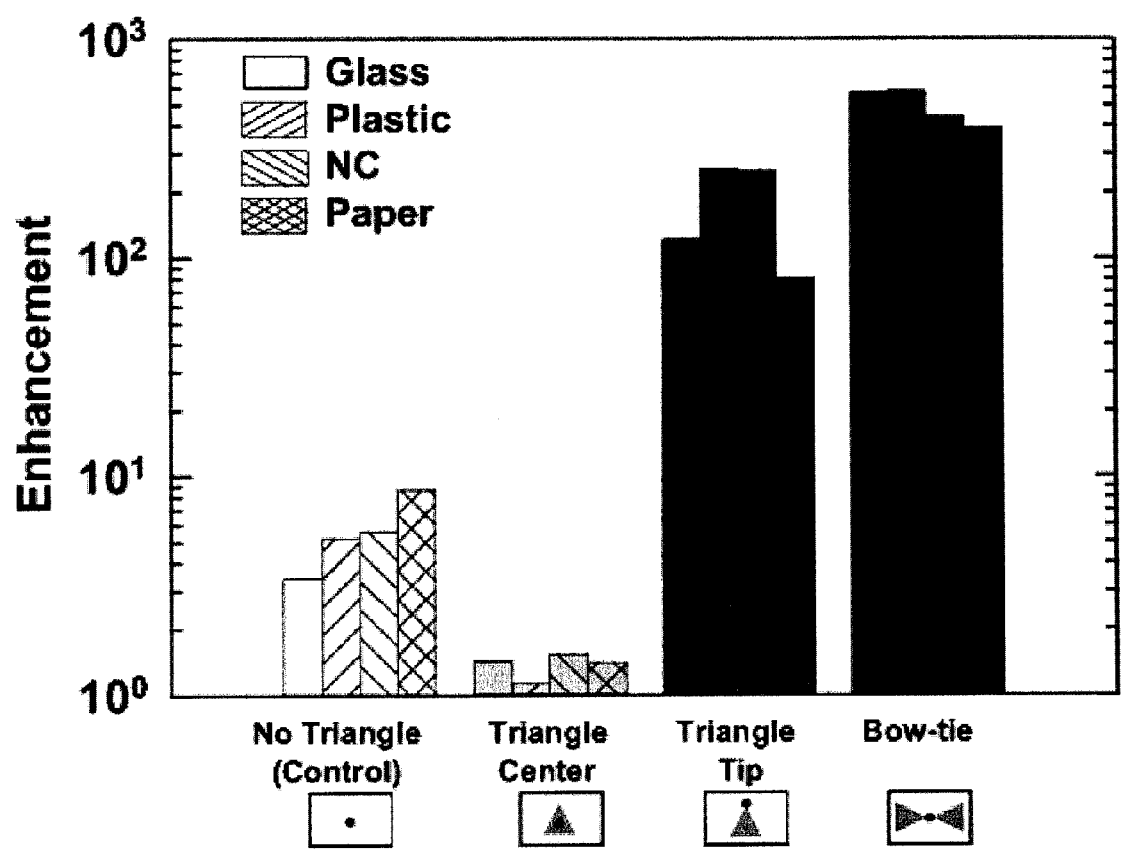
FIG. 25 shows chemiluminescent microwave (Mw) enhancement ratios (Mw/no Mw) upon application of low-power microwave pulses (Mw) for different sample geometries on various dielectric substrates.

In addition to the possibility of creating transferable aluminum structures for disposable sensing applications, the feasibility of creating disposable aluminum structures to increase the sensitivity of protein detection on common sensing substrates was demonstrated. 12.3-mm triangle geometries were cut from aluminum sheets (~100 um thick) and affixed to different substrates, as shown in FIG. 25, such that the gap size was ~1 mm for the disjointed bow tie geometry. Image wells were again placed at the tip of a single aluminum triangle, between two aluminum triangles, at the center of the aluminum triangle, and on plain substrates. Wells on the respective sample geometries were filled with 6 uL of blue chemiluminescence material and subsequently exposed to a 5-s microwave pulse. From recorded intensity data, almost equivalent enhancement trends were observed when the technology is adapted to common protein detection sensing substrates, most notably nitrocellulose and plastic.

Figure 26:
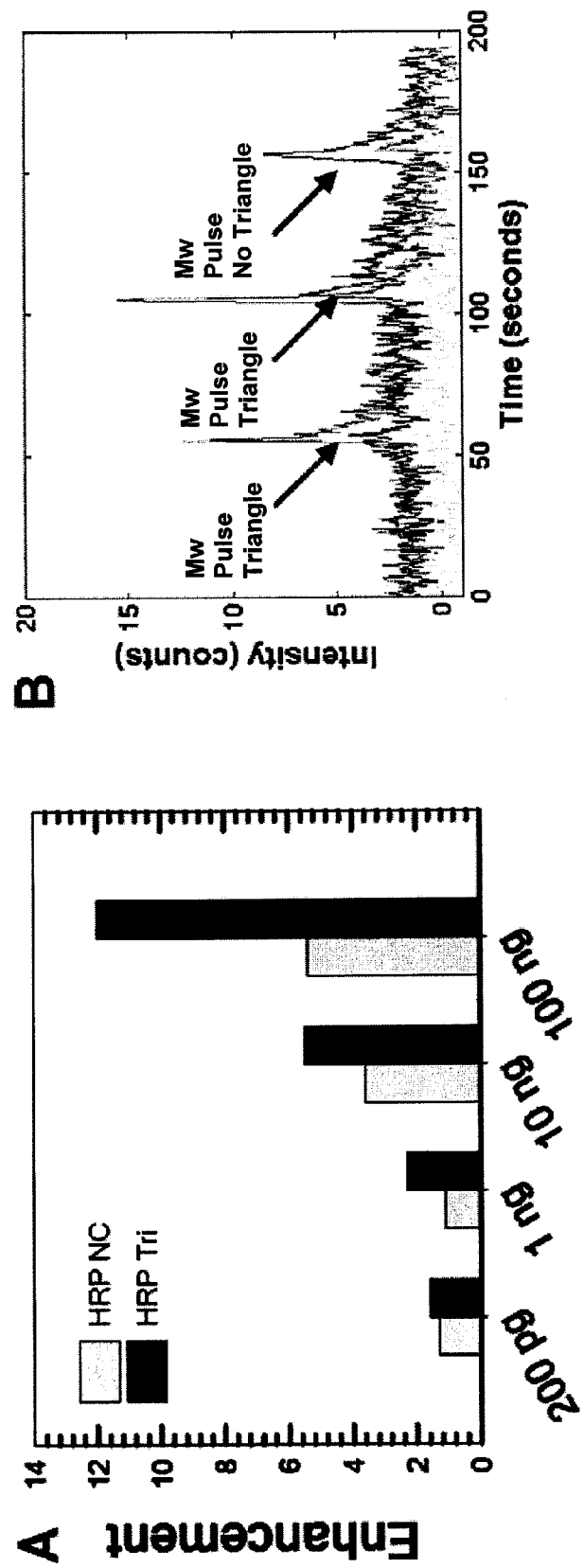
FIG. 26 shows (A) HRP assay enhancement as a ratio of maximum chemiluminescent emission to steady-state chemiluminescent emission before application of Mw power HRP assays. Enhancements with (dark gray bars) and without affixed aluminum foil triangle (light gray bars) are shown. Chemiluminescence signal intensity time traces for (B) 10 ng of HRP on NC membrane samples, whereby 100 uL of chemiluminescence solution (acridan/peroxide) was added, and a train of three 5-s microwave pulses (Mw pulse) at 50-s time intervals were applied at low microwave power to induce triggered increases in photon flux. Chemiluminescence signal was recorded for samples with a single affixed aluminum triangle, no triangle, and background signal.

To demonstrate another biologically relevant application of spatially triggered chemiluminescence from a variety of dielectric substrates, NC HRP dot blots were used to model a typical Western blot scheme, whereby proteins are transferred and immobilized on nitrocellulose membranes. The detection limit for this detection scheme without microwave induced enhancement is ~10 ng of HRP. With the application of the low-power microwave pulse train, in the absence of aluminum structures, enhancements were observed for 100- and 10-ng samples as shown in FIG. 26 A (light gray bars), but relatively no enhancement for the 1 ng and 200 pg samples. This is dually noted by a representative emission time traces for the nitrocellulose samples treated with 10 ng of HRP, whereby peaks correspond to microwave (Mw pulse)-induced increases in photon flux, as shown in FIG. 26 B. In the presence of the affixed aluminum triangle, not only were increases in photon flux observed from the sample, as shown in FIG. 26 B, but also the sensitivity of detection is increased by a factor of 50, as shown in FIG. 26 A (dark bars). Although detectability was improved for low protein concentrations on nitrocellulose membranes by 50-fold, it is believed that sensitivity improvements can be achieved beyond 50-fold with more efficient signal detection means.

It was further demonstrated that aluminum structures can be implemented to create highly sensitive multiplexed chemiluminescent assays for high-throughput screening with readily available and inexpensive materials. At the corners of the 8-mm square structures ~100 um thick, the microwave enhancement of the chemiluminescence emission is >300-fold, as shown in FIG. 27 A. While on a plain glass substrate in the absence of aluminum foil structures, there was only a 3-fold enhancement, as shown in Table 1. Thus, the on-demand photon flux at the corners of the aluminum square geometries is 100-fold greater than the on-demand photon flux achieved with conventional microwave heating. For the solution placed on the center of the aluminum structure, negligible enhancement was observed (1.4-fold) upon exposure to a low-power microwave pulse. Images of four chemiluminescence solutions of different colors at the corners of 8-mm square aluminum structures are shown before (FIG. 27 B) and after (FIG. 27 C) the application of microwave pulses to demonstrate the ability to easily adapt this technology to a multiplexed or high-throughput chemiluminescent assay platform.

4.15. Discussion

Since the simulated aluminum structures are modeled as perfect conductors, maximum spatial field distributions are localized at the corners or tips of the aluminum structures, and "ohmic" loss to the metal and its subsequent heating due to plasmon effects is negligible. As a result, maximum dielectric loss to the solution is proximal to the corners or tips of the aluminum structures. Thus, the increased reaction rates of the chemiluminescent reaction is caused by the subsequent heating of the solution due to dielectric loss, which is also confirmed by Arrhenius plots for the chemiluminescent solutions and increased heating rates and temperatures of the Ru(by)$_2$Cl$_2$ aqueous solutions.[47] On the other hand, the relative lack of any signal enhancement from the center of the triangle structures confirms a negligible plasmon effect and subsequent ohmic heating on the metal structures. With minimal effort, materials, and equipment, a new platform technology has been demonstrated to locally trigger chemiluminescent reactions from a variety of dielectric substrates and achieve >500-fold increases in reactivity.

Since the HRP reactions sustain activity during exposure to microwave pulses and in proximity to the metal structures, the heating of the solution does not deactivate HRP, which suggests other proteins, i.e., alkaline phosphatase, will maintain stability under similar conditions. While intensely focused microwave fields of the prior art can lead to uncontrolled temperature increases and, potentially, denature or damage proteins and small molecules, the presently disclosed technology affords many practical controls for this effect. The >95-fold increase in heating rates of aqueous solutions is combined with pronounced cooling of solutions proximal to the conductive metal structures. Subsequently, this technology potentially offers temperature jumps and rapid cooling rates that exceed denaturation rates of proteins. In this regard, it is also conceivable that optimized structures can be designed to adequately balance the heating and cooling rates to develop inexpensive monomode reactors for microwave organic synthesis reactions. Furthermore, the extent of heating can be changed by changing the volume of solution or positioning sample distal from the region of maximum electric field enhancements. While the applicability of this technology has been demonstrated using 2.45-GHz radiation, preliminary data suggest the general applicability of the technology over a range of microwave frequencies, which implies selective heating of different dielectric media and materials.

Figure 34:
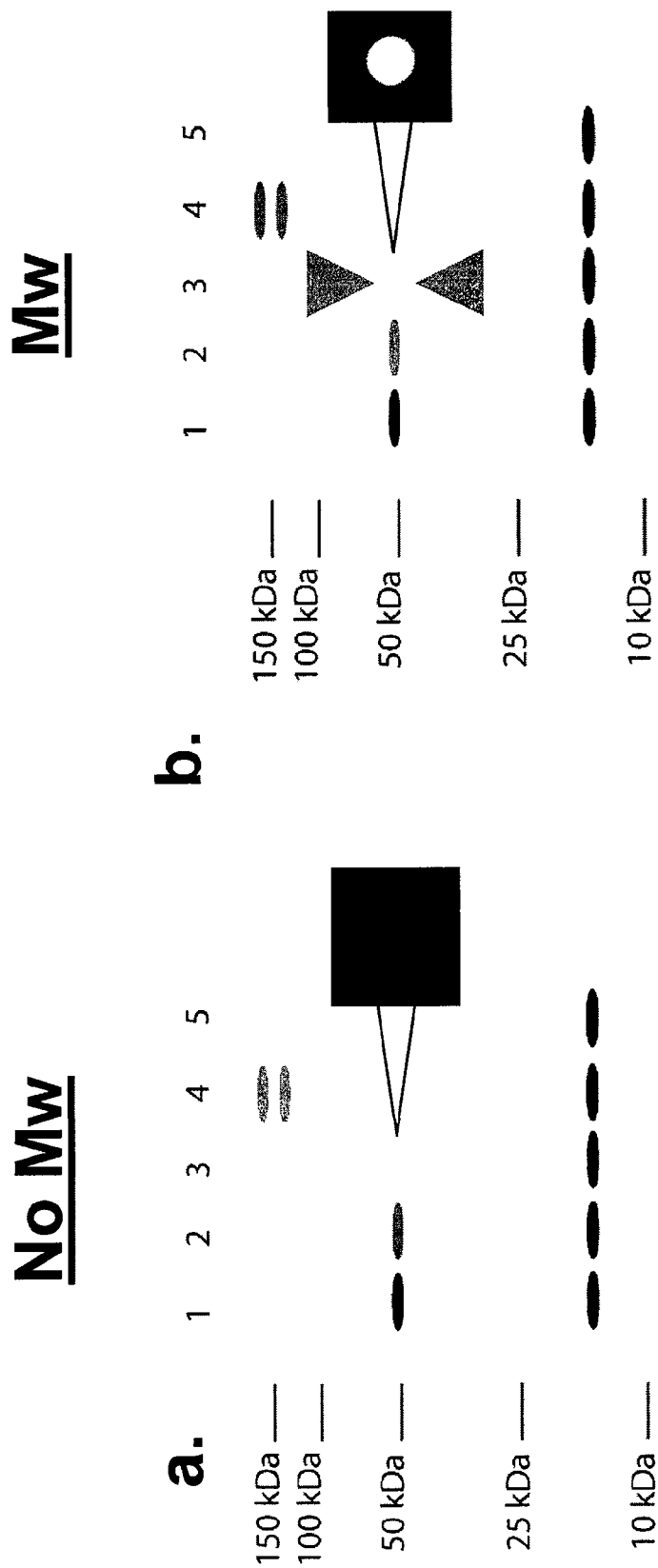
FIG. 34 illustrates a potential application of the technology by amplifying dim bands from a hypothetical Western blot scheme, whereby weak chemiluminescence signal from a Western blot (A) without affixed triangle geometries (left, inset) can be hypothetically amplified (B) with a disjointed 'bow-tie' geometry attached.

The triggering of HRP surface reactions not only provides advantages in terms of signal-to-noise ratios for sensing and biological reactions, but reduced detection times were observed for assays performed in the presence of the triangle substrates, as shown in FIG. 33 cont. In addition, it has been shown that disposable planar aluminum structures can be affixed to common sensing substrates, i.e., nitrocellulose membranes, to locally trigger enzyme (HRP)-catalyzed chemiluminescent reactions. Further, a Western blot, as shown in FIG. 34 demonstrates the potential utility of this technique to amplify weak bands from nitrocellulose membranes by affixing aluminum triangle geometries to regions of interest.

4.16. Conclusions

Thus, this relatively inexpensive approach to focusing microwave fields can facilitate the general utility of microwave technology in many scientific disciplines. More specifically, aluminum geometric substrates can be used to directionally amplify microwave radiation to accelerate solution-based chemical reactions. In addition, it has been shown herein the potential utility of this generic approach to microwave sensing to provide another means for not only dramatic improvement of signal-to-noise ratios for surface assays but also the potential application of these focused microwaves for the increased specificity, sensitivity, and rapidity of clinical sensing applications, chemical synthesis, biological assays, biosensing, and chemical sensing technologies.

5. Planar Geometrical Aluminum Substrates 5.1 Materials

Bovine-biotinamidocaproyl-labeled Albumin (biotinlyated BSA), HRP-labeled avidin, 99.999% aluminum evaporation slugs, silicon monoxide pieces, and premium quality APS-coated glass slides (75×25 mm) were obtained from Sigma-Aldrich. CoverWell imaging chamber gaskets with adhesive (5 mm diameter, 2 mm deep) were obtained from Molecular Probes (Eugene, Oreg.). Steptavidin-HRP pre-diluted solution (Catalog #20774) was obtained from Chemicon® International Inc. Chemiluminescence reagents for these experiments were purchased from Amersham Biosciences (ECL Plus™ Western blotting detection kit, RPN2132).

5.2. Preparation of Glass Substrates Modified with Thin Film Aluminum Triangles

Aluminum films approximately 50 nm thick were vapor deposited on silanized glass slides with an EMF Corp. (Ithaca, N.Y.) instrument. Upon completion, a thin silicon monoxide layer 5 nm thick was vapor deposited to insure that surface protein interactions are approximately equivalent for glass and metal substrates. Square geometries, with lengths 2.5, 5, 10 and 20 mm, were etched into the thin film aluminum substrates for metal surface and solution chemiluminescence emission enhancement comparisons. Slides modified with aluminum square substrates were cut into approximately 1×1.5 in$^2$ rectangles.

5.3. Preparation of the Model Protein Assay (Biotin-Avidin) on Aluminum Films and Glass Substrates The model assay used in this paper is based on the well-known interactions of biotin and avidin. Biotin groups are introduced to the glass and metal surfaces through biotinylated-BSA, which readily forms a monolayer on the surfaces of glass. Surface luminescent decay experiments were carried out by incubating 5 μl of 10 nM biotinylated-BSA solutions in the Al and glass imaging chambers for approximately 1 hour. Chambers were washed with water to remove the unbound material. Imaging chambers were then incubated with 20 μl of 1% aqueous BSA (w/v) for one and a half hours to minimize non-specific binding of HRP-streptavidin to surfaces. Chambers were again washed with water to remove the BSA blocking solution. Stock solutions of HRP-streptavidin were diluted 1:25 to a final approximate concentration of 10 μg/ml. Five microliters of the HRP-streptavidin solution was subsequently added into the imaging chambers affixed to the biotinylated-BSA coated glass and Al modified substrates and typically incubated at room temperature for approximately 30 minutes. Following incubation, imaging chambers were again washed with water to remove unbound HRP-streptavidin material and the chemiluminescence solution was subsequently added. In all of the experiments performed with low power microwaves, there was no evidence of surface drying. Solution assays were performed by mixing the chemiluminescence and 2 μl of 200 ng/ml of HRP-streptavidin solution, to the chemiluminescence reagents to trigger the reaction.

5.4. HRP-Catalyzed Chemiluminescence from Reagents on al and Glass Surfaces

The chemiluminescence experiments were performed with and without microwave (Mw) heating inside the microwave cavity (0.7 cu ft, GE Compact Microwave Model: JES735BF, max power 700 W). During microwave heating, 10 second pulses were applied at three or four 50 second intervals. The pulses were applied at 10%, 20%, 30% or 40% power respectively, which corresponded to 70, 140, 210, and 280 W over the entire cavity. Solutions A and B were mixed in different proportions to optimize chemiluminescence signal for these experiments. As a result, the maximum emission signal was measured from a 20:1 mixture of solution A to B. Subsequently, all reactions were performed by combining 40 μl of solution A with 2.0 μl of solution B and immediately adding the entire solution to the imaging chamber. Data collection commenced immediately following addition of reagents, and terminated when the photon counts returned to baseline. Histogram plots (FIGS. 36 and 37) reflect maximum signal counts detected before an initial microwave pulse (no Mw) and after the application of microwave pulse trains (Mw).

5.5. Chemiluminescence Reagents (Chemical Reaction Assay)

The commercially available glow-sticks contain the necessary reacting chemicals, which are enclosed within a plastic tube, and yield a bright chemiluminescent emission when they are physically altered. The plastic tube contains a phenyl oxalate ester and a fluorescent probe, where the choice of dye simply determines the color of the luminescence. Inside the plastic tube lies a glass capsule containing the activating agent (hydrogen peroxide). Activation of the chemicals is accomplished with a bend, snap, and a vigorous shake of the plastic tube which breaks the glass capsule containing the peroxide and mixes the chemicals to begin the chemiluminescence reaction. The hydrogen peroxide oxidizes the phenyl oxalate ester to a peroxyacid ester and phenol. The unstable peroxyacid ester decomposes to a peroxy compound and phenol, the process chemically inducing an electronic excited state. Commercially available chemiluminescence materials were purchased and used to demonstrate the utility of the microwave-focused chemiluminescence approach.

Figure 39:
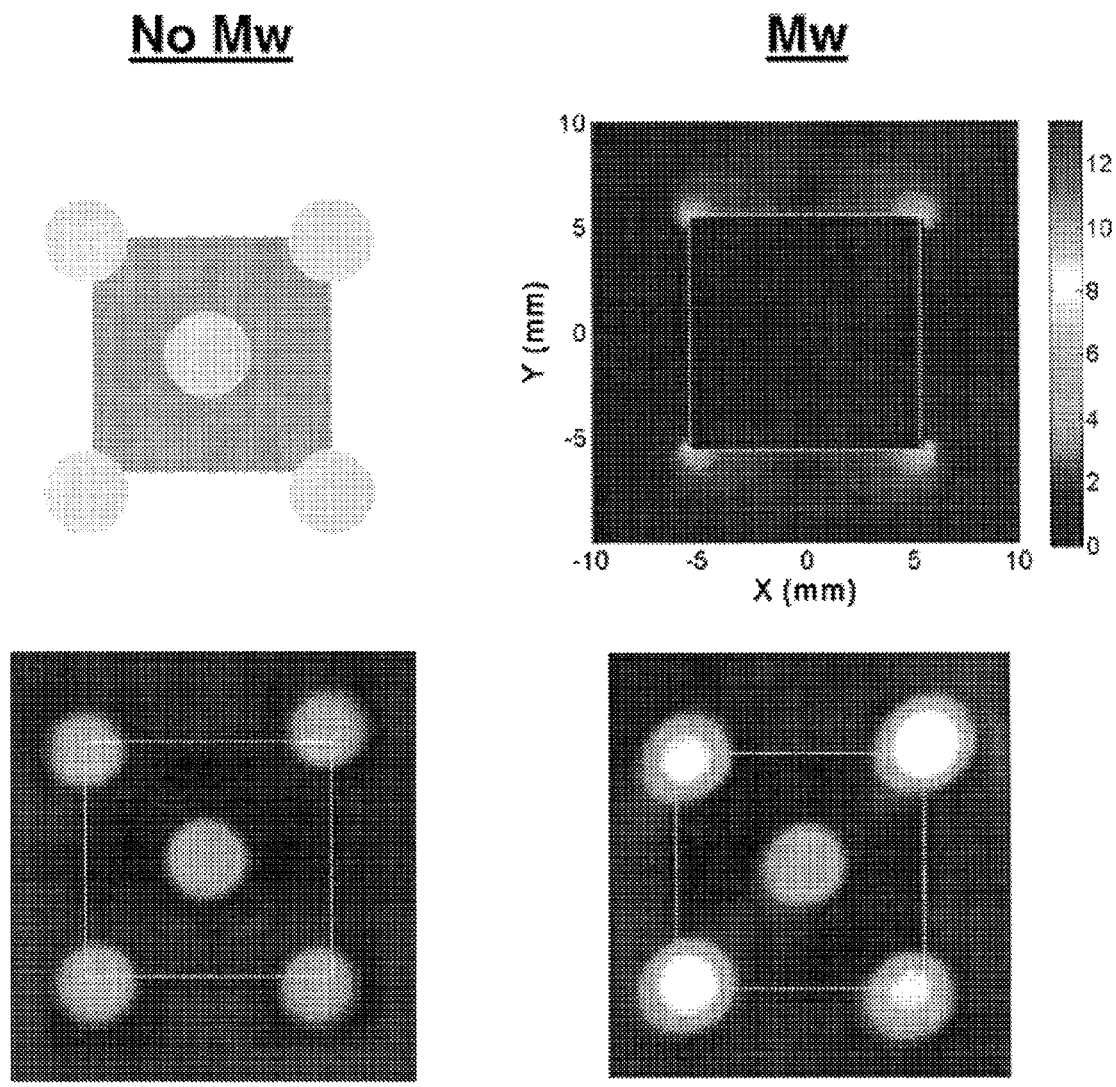
FIG. 39 shows the ample geometry that depicts the chemiluminescence sample and aluminum/SiOx square substrate. Without an incident low power microwave pulse, the chemiluminescence signal is approximately equivalent for all sample geometries (left bottom). Upon application of low power 2.45 GHz microwave pulses (for simulation results, E field is simulated as a TE polarized TFSF and propagates across the geometries from left to right), the experimental localized signal enhancement at the corners of the square aluminum substrate (right bottom) correlates with simulated total field intensity distributions (top right)

Chemiluminescence images, as shown in FIG. 39, from square aluminum substrates with a length of 11 mm were acquired by affixing 2.5 mm imaging chambers at the 4 corners of the etched square geometry and one chamber at the center of the square. Subsequently, 6 µl of solution was placed in each of the imaging chambers and the images were recorded before and after the application of a 5 second, low power (70 W) microwave pulse.

5.6. Results

Figure 35:
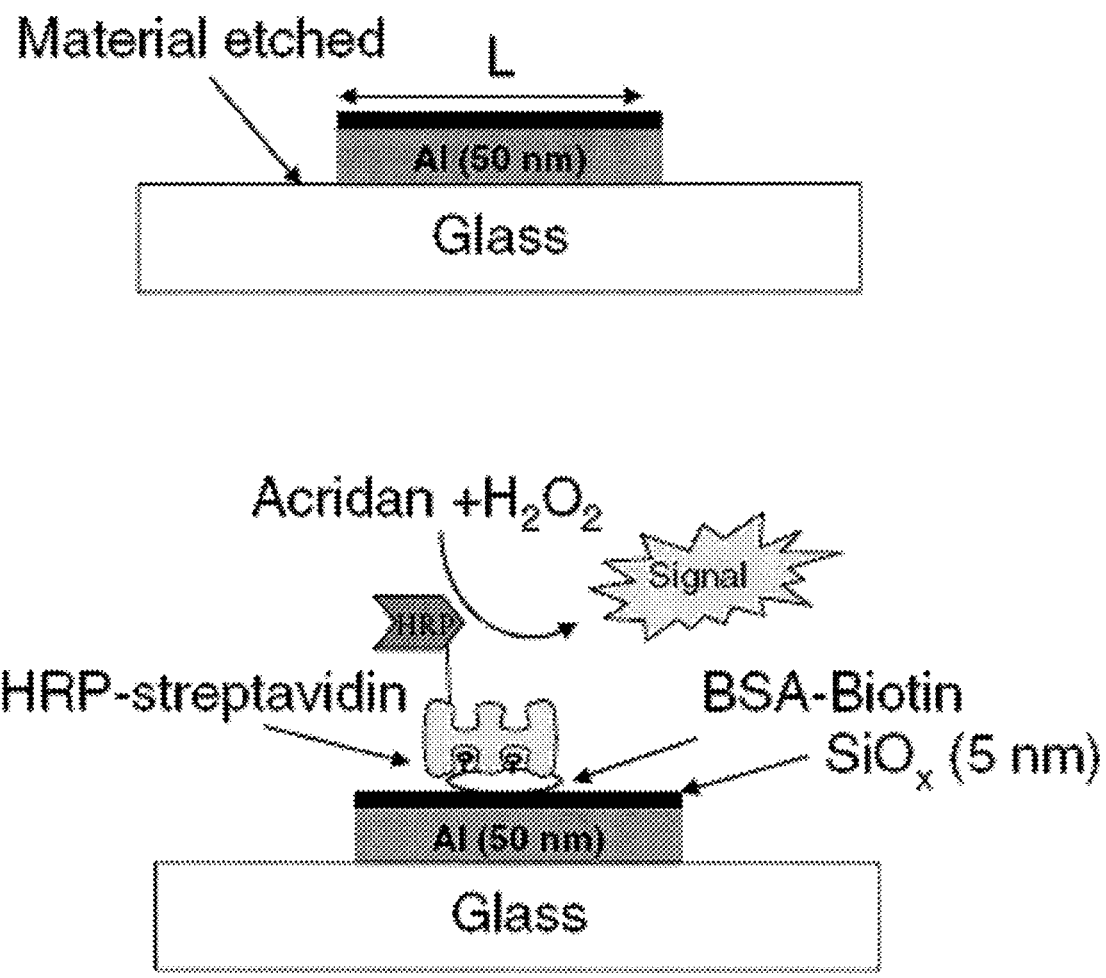
FIG. 35 shows the sample geometry scheme for aluminum square substrates (top) that are used for surface and solution assays as shown in FIG. 37. Aluminum and SiOx layers are vapor deposited with thicknesses of 50 and 5 nm respectively. The material is then etched to form square Al/SiOx substrate geometries with a length (L). Scheme for BSA-biotin/HRP-streptavidin chemiluminescence surface assay is also shown (bottom)

In order to demonstrate the potential utility of aluminum substrates to further increase enhancements observed for the MT-MEC platform, a simple surface assay was constructed as described in the experimental section and shown in FIG. 35. Briefly, aluminum thin films 50 nm thick were vapor deposited onto silanated glass slides. In addition, silicon monoxide layers 5 nm thick were also deposited onto the aluminum substrates, such that surface protein interactions to aluminum and glass are similar.

Figure 36:
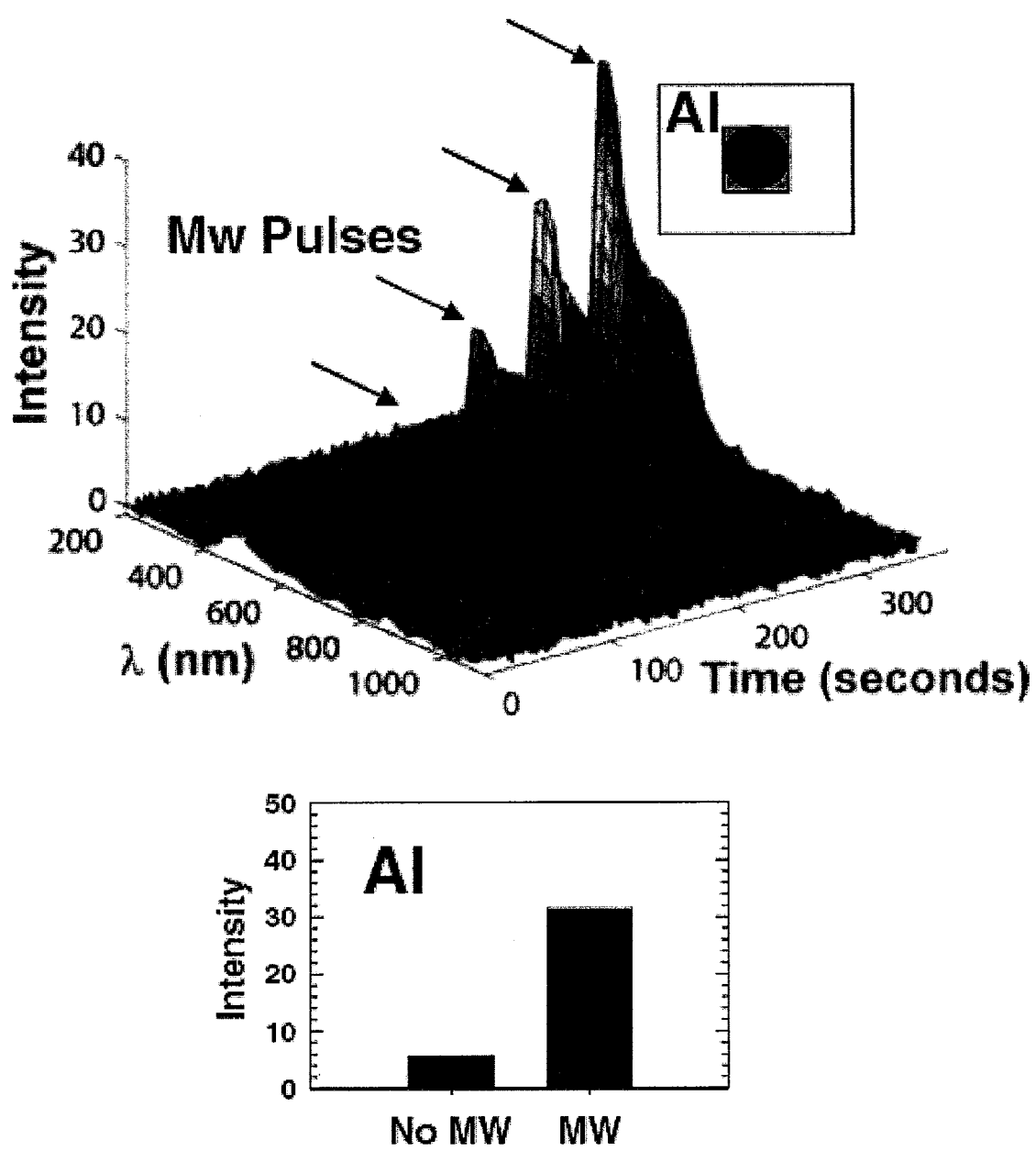
FIG. 36 shows 3D time traces of chemiluminescence emission spectra from 40 µl acridan/peroxide solution (insets, blue circles) on aluminum/SiOx (Al, top; inset, light grey box) and glass (G1, FIG. 36 Cont. top, inset, white rectangle) substrates incubated with BSA-biotin/HRP-streptavidin complexes. Low power microwave pulses (Mw pulses) are applied at 50 second intervals for 10 seconds at 70 W, 140 W, 210 W and 280 W. Chemiluminescence emission intensity histograms before (no MW) and after (Mw) exposure to microwave pulses from aluminum (bottom) and glass substrates (FIG. 36 cont. bottom) coated with BSA-biotin/HRP-streptavidin complexes. Aluminum films 50 nm thick and a subsequent SiOx 5 nm thick layer were vapor deposited onto glass substrates. Substrate surfaces were then incubated with 50 nM BSA-biotin and 10 mg/ml solution of HRP-streptavidin
Figure 36:
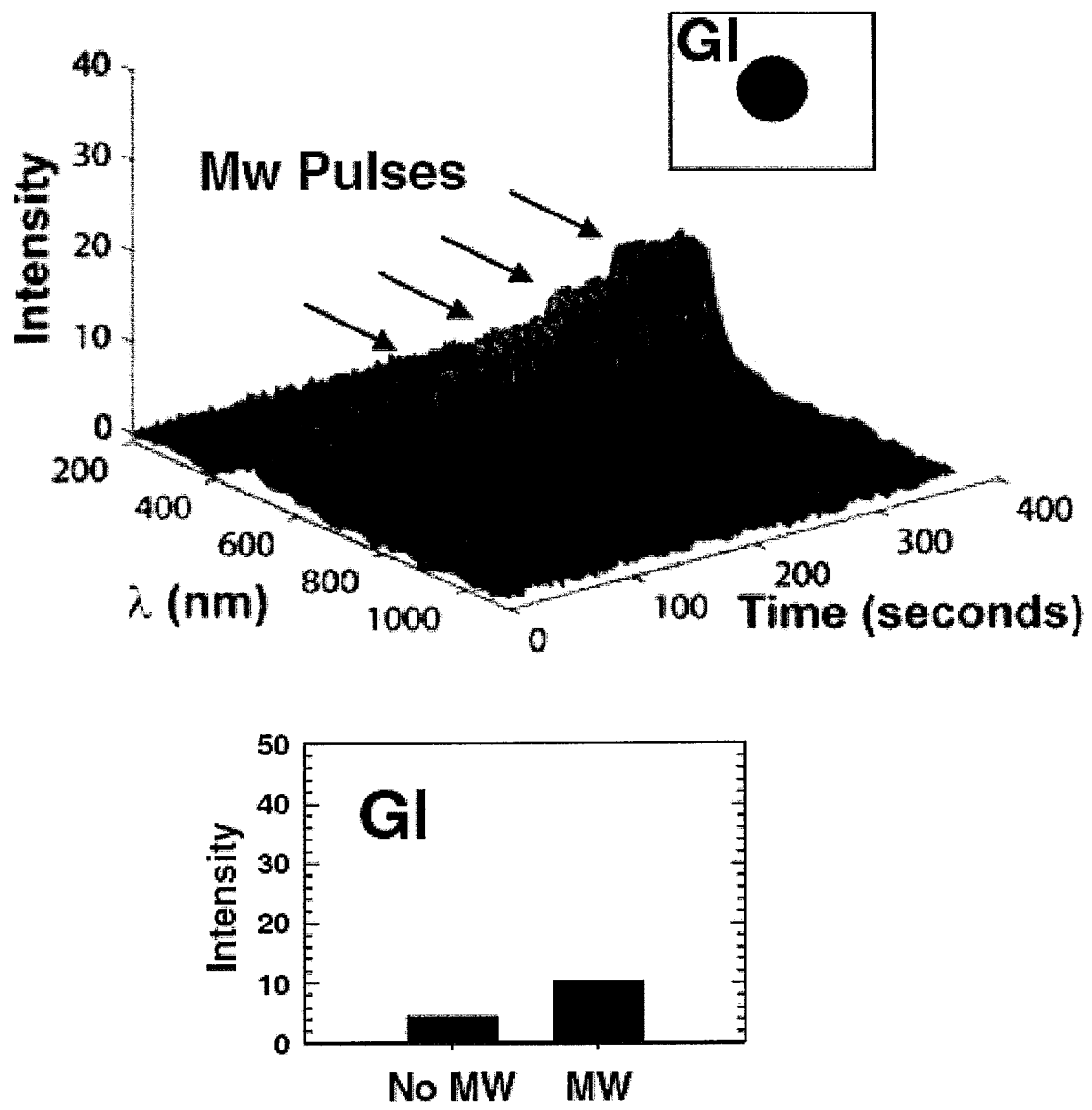

To demonstrate the relative enhancements achieved with aluminum substrates, 10 nM biotinylated-BSA was incubated onto glass substrates and aluminum substrates etched to best approximate the area of an affixed imaging chamber, which is 5 mm diameter. HRP-streptavidin was then added to the surface, localizing the enzyme catalyst in close proximity to the aluminum substrate. The peroxide and acridan (lumophore) were then added to initiate the chemiluminescence reaction. Subsequently, spectral traces was recorded for the reaction on the aluminum, as shown in FIG. 36 top left and glass substrates, top right, t 1 second time intervals for 400 seconds. During the 400 second detection times, the aluminum (Al) and glass (Gl) substrates were exposed to four, 10 second low power microwave pulses (70 W, 140 W, 210 W, and 280 W respectively) at fifty second time intervals (arrows, FIG. 36, top). Prior to the application of equivalent microwave pulse trains to glass and aluminum protein treated substrates, the maximum signal achieved from the steady chemiluminescence emission was measured that is reflective of the HRP catalyzed chemiluminescence reaction (FIG. 36, No MW bottom). Following the application of the low power Mw pulses, the maximum signal achieved from the 'triggered' enzyme catalyzed chemiluminescence reaction was measured. In the presence of the aluminum substrate, the application of low power microwave pulses dramatically increases the photon flux from the chemiluminescence reaction, as shown in FIG. 36 for Al).

It was observed that upon application of low power microwave pulses, $10\times10$ mm$^2$ aluminum substrates were slightly warmer than the glass substrates that were not treated with aluminum films. Thus, it was questioned whether the relative enhancement that was observed for the aluminum substrate was a heating effect, and the relative enhancements from aluminum substrates are dependent on the size of the aluminum substrates, i.e. larger enhancements arose from larger aluminum surface area. Subsequently, $20\times20$ mm$^2$ aluminum squares were etched on glass substrates and prepared the surface assay as shown in FIG. 35.

Upon application of the low power microwave pulses, sparking or dielectric breakdown was noted of the aluminum substrate. Consequently, it is appropriate to maintain a minimum size for aluminum substrates. Thus, aluminum square geometries with lengths 10 mm, 5 mm and 2.5 mm were prepared and functionalized with the BSA-biotin/HRP-streptavidin complexes and exposed to three 10 second microwave pulses (70 W, 140 W, and 210 W, respectively) at 50 second time intervals. In addition, solution assays were performed and also exposed to the aforementioned microwave pulse trains. Solution experiments were performed to determine if the heating is localized to the surface, strictly due to solution heating, or a combination of both phenomena.

Figure 37:
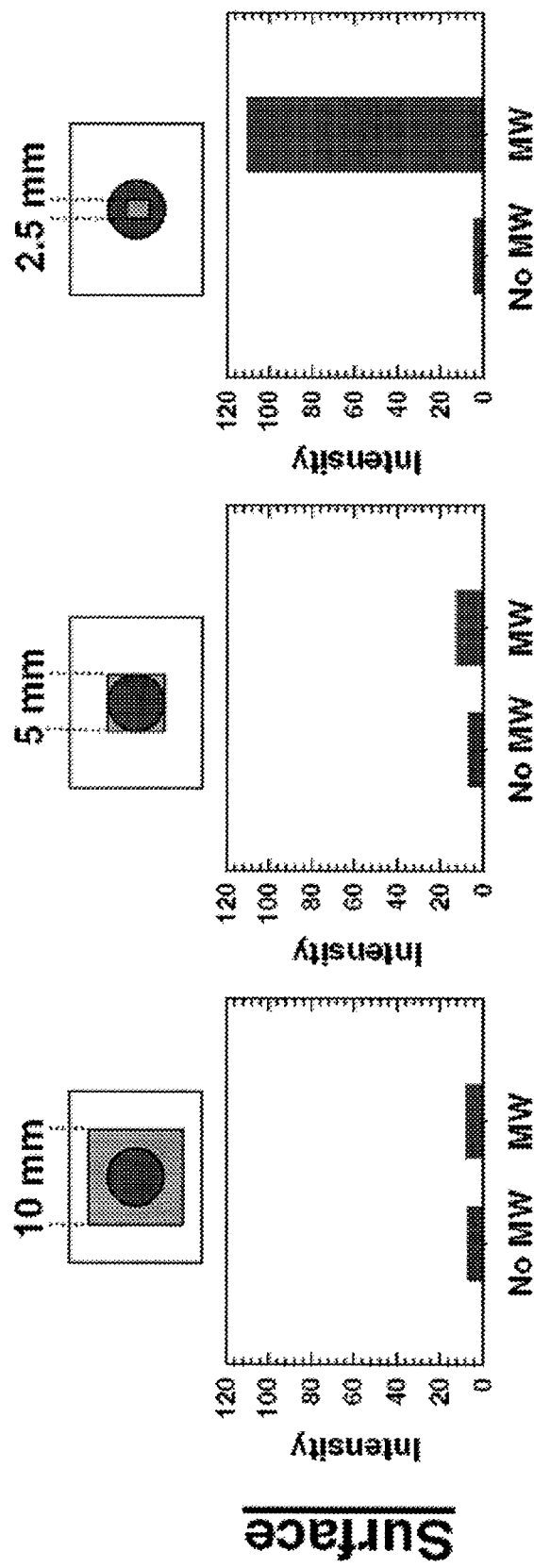
FIG. 37 shows chemiluminescence intensity histograms before (No Mw) and after (Mw) exposure to microwave (Mw) pulses for surface bound HRP (top panels) and HRP in solution (middle panels) on continuous Al films 50 nm thick with 5 nm thick SiOx layers with square geometries of lengths 10, 5, and 2.5 mm Surfaces were treated with 10 nM BSA-biotin and 20 µg/ml solution of HRP-streptavidin, and 40 µl of acridan/peroxide solution was subsequently added to an imaging chamber affixed to metal substrates. For solution assays, 2 µl of a 20 µg/ml HRP solution was added to 40 µl of acridan/peroxide. Maximum intensity after Mw is divided by maximum intensity before initial Mw pulse to give enhancement ratios (FIG. 37 cont. bottom)
Figure 37:
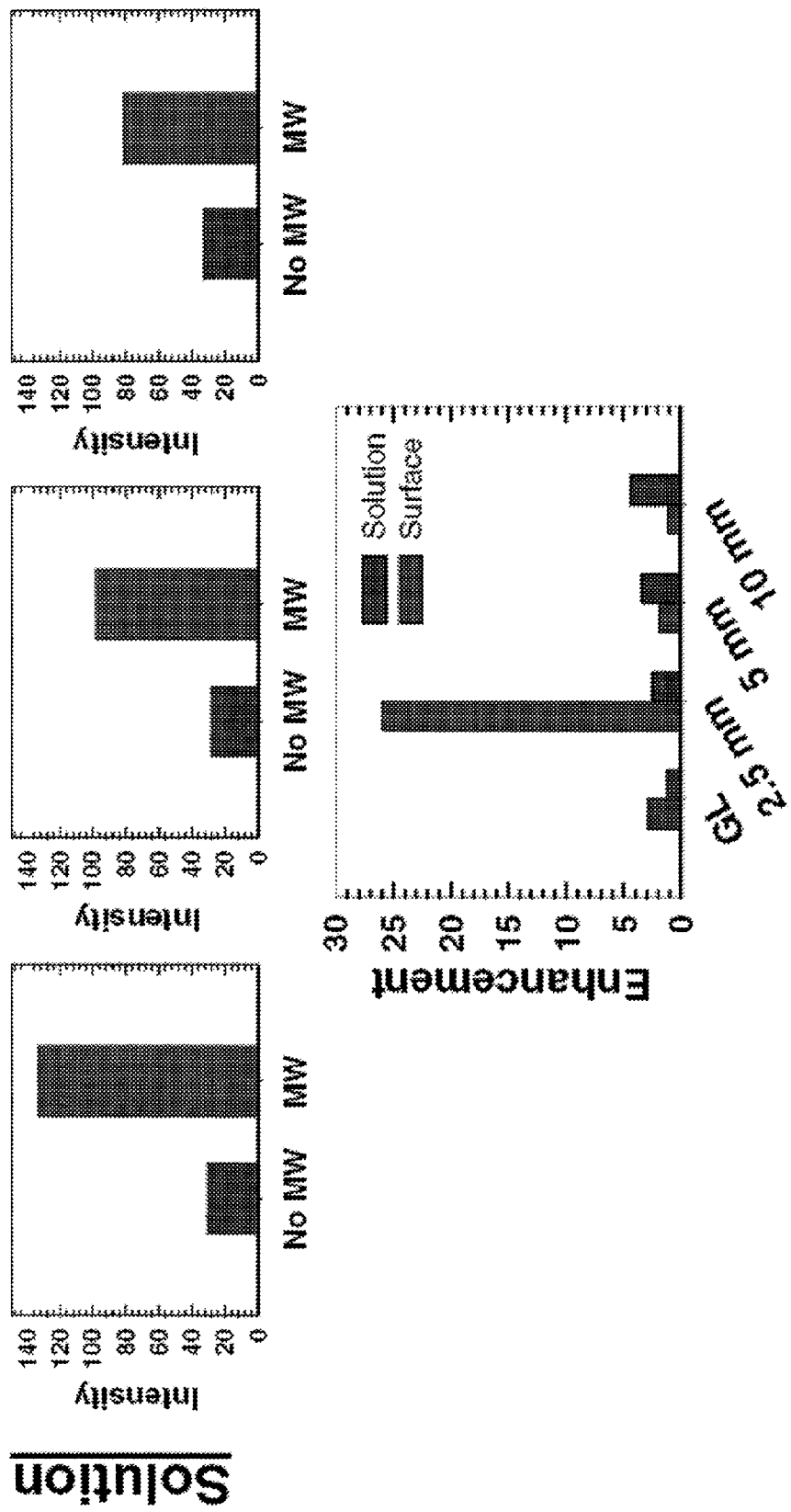

Prior to the application of equivalent microwave pulse trains to glass and aluminum protein treated substrates, the maximum signal achieved from the steady chemiluminescence emission was again measured that is reflective of the HRP catalyzed chemiluminescence reaction, as shown in FIG. 37, No MW bars. Following the application of pulses, the maximum signal achieved from the 'triggered' enzyme catalyzed chemiluminescence reaction was measured (Mw bars). In the presence of the 2.5×2 5 mm$^2$ square aluminum substrates, maximum photon flux is achieved from the surface chemiluminescence reactions, as shown in FIG. 37, top right, while minimum enhancements were noted for the 5×5 mm$^2$ (center) and 10×10 mm$^2$ square aluminum substrates (left). On the other hand, solution studies show an opposing trend, as shown in FIG. 37 cont. top panels. In the presence of the 10×10 mm$^2$ square aluminum substrates, maximum 'triggered' photon flux is achieved from the solution based chemiluminescence reactions (left top), while minimum enhancements are noted for the 5×5 mm$^2$ (middle top) and 2.5×2 5 mm$^2$ square aluminum substrates. The maximum enhancements for surface (>25-fold,) and solution (>4-fold,) reactions demonstrate marked increases in photon flux for microwave triggered enzyme catalyzed chemiluminescent reactions from aluminum substrates, as shown in FIG. 37 cont., bottom.

Figure 38:
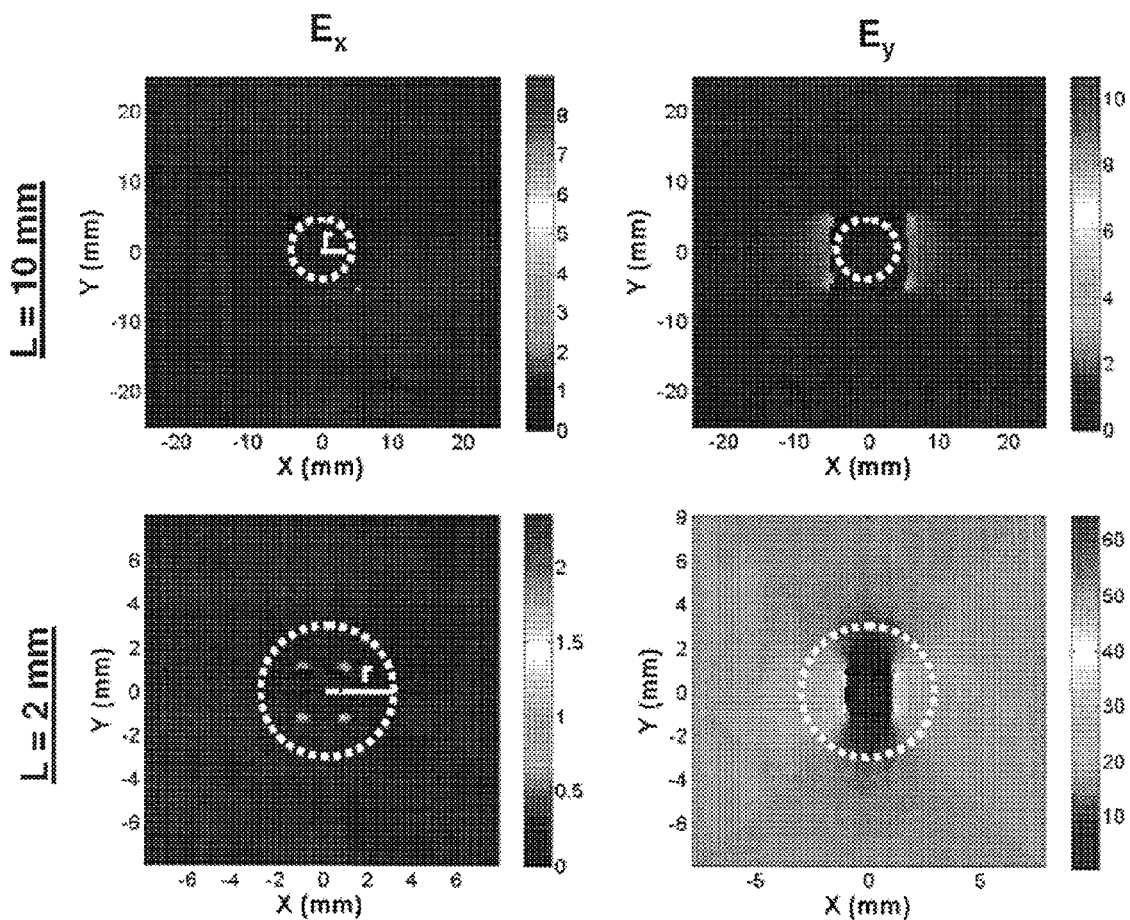
FIG. 38 shows representative simulated intensity images of the electromagnetic field distribution for 2.45 GHz microwave frequencies incident upon aluminum squares with lengths of 10 mm and 2 mm. The incident field is modeled as a total field scattered field (TFSF) with TE polarization and propagates from left to right. Dashed black region approximates simulation region defined as planar aluminum square. Dotted white region approximates the relative coverage area (r=2.5 mm) of the imaging chamber with chemiluminescence solution that yielded the experimental results as shown in FIGS. 36 and 37.

The performed FDTD calculations showed that the four corners of the square geometries exhibit the maximum electric field enhancements, as shown in FIG. 38. Because similar radiation maxima locations were observed for 2 D and 3 D simulations (data not shown), the 2D FDTD simulations was used to demonstrate the relative electric field distributions. Square planar structures are assumed to be an infinite column and act as an electromagnetic condenser. Thus, these structures are acting as lightening rods for charge buildup at the corners of the squares to drive the chemical reactions. Since the fields for the square geometries are localized at the corners, it is evident that the field enhancements for the larger square geometries will lie outside the region of the imaging chamber, which is approximately 5 mm in diameter (FIG. 38, dotted circles). On the other hand, the smaller square geometries will have field enhancements within the region of the imaging chamber. Since the field enhancements for the smaller geometries exist within the sample region (white dotted circle) and enhancements spread into surrounding areas, it is believed that these fields are the source of the significant surface enhancements noted for the 2.5×2 5 mm² square geometries. In contrast, for the larger geometries, the fields lie well outside the sample region and the solution signal enhancements can be explained by ohmic heating of the aluminum and glass substrates.

Finally, a square aluminum/SiOx substrate with a length of 11 mm was etched on a glass slide as previously described. Subsequently 2.5 mm chamber wells were affixed at the four corners of the square geometry and one chamber well at the center of the square and filled them with 6 µl of green chemiluminescence solution, as shown in FIG. 39 top. Prior to applying low power microwave pulse, an image of the luminescent material was recorded. The intensity of the material at the five positions on the squares was approximately equivalent, as shown in FIG. 39 left bottom. Upon application of a five second, low power microwave pulse (70 W), dramatic signal enhancements was observed from the chemiluminescence solution at the four corners of the square Al/SiOx substrate, as shown in right bottom, and a slight intensity increase for the solution at the center of the square.

5.7 Conclusion

Combining the advantages of MT-MEC with optimized aluminum planar geometries, the sensitivity and rapidity of surface and solution protein detection with chemiluminescence is improved. Using optimized aluminum geometrical planar structures to localize microwave field enhancements, focus microwave fields can be focused and thus control the extent and location of field enhancements, such that not only can chemiluminescent reactions be temporally 'triggered' but also these reactions can be spatially 'triggered'. A >25-fold and >4-fold enhancements was observed for surface and solution reactions respectively. Thus, Microwave Triggered Metal-Enhanced Chemiluminescence (MT-MEC) on aluminum planar geometrical substrates, can be used to improve sensitivity, rapidity, specificity, and quantification of macromolecules, organic syntheses, cancer detection, cancer treatments, cellular studies and a host of other sensing technologies.

Further, the system and technology of the present invention can be used in multiple areas including spatial and temporal control of chemically and enzymatically catalyzed chemiluminescence reactions to increase or decrease sensitivity and rapidity of reactions including small molecule reactions, including DNA, RNA, Protein, Viruses, Toxins, Pathogens, etc.; organic synthesis; and/or combination chemistry. An assay system can be constructed to create high-throughput system for any of the above detection systems. Further, the assay system can be manipulated to act as a circuit that can be turned on or off depending on the exposure of microwaves and placement of the metallic structures. It is further envisioned that the creations of a reactive zone that can be trigger to be in on or off positions, can be used in powering low-power devices for medical or general use, such as LED, low power portable devices for detecting fluorescence, phosphorescence, electroluminescence and/or electromagnetic radiation.

REFERENCES

All references cited herein are hereby incorporated by reference herein for all purposes.

[1] O. Hofmann, P. Miller, P. Sullivan, T. S. Jones, J. C. deMello, D. D. C. Bradley, A. J. deMello (2005). Thin-film organic photodiodes as integrated detectors for microscale chemiluminescence assays. *Sensors and Actuators BChemical* 106 (2), 878-884.

[2] O. Myhre, J. M. Andersen, H. Aarnes, F. Formum (2003). Evaluation of the probes 2',7'-dichlorofluorescin diacetate, luminol, and lucigenin as indicators of reactive species formation. *Biochemical Pharmacology* 65(10), 1575-1582.

[3] I. Bronstein, C. S. Martin, J. J. Fortin, C. E. M. Olesen, J. C. Voyta (1996). Chemiluminescence: Sensitive detection technology for reporter gene assays *Clinical Chemistry* 42 (9), 1542-1546.

[4] P. Moris, I. Alexandre, M. Roger, J. Remacle (1995). Chemiluminescence Assays of Organophosphorus and Carbamate Pesticides. *Analytica Chimica Acta* 302 (1), 53-59.

[5] A. M. Garcia-Campana, Willy R. Baeyens (2001). *Chemiluminescence in Analytical Chemistry*, Marcel Dekker. New York.

[6] J. E. Wampler (1985). Instrumentation: Seeing the Light and Measuring It, in *Chemi-and Bioluminescence*, J. G. Burr, Ed. Marcel Dekker, New York. pp. 1-44.

[7] F. Berthold (1990). Instrumentation for Chemilunescence Immunoassays, in *Luminescence immunoassays and Molecular Applications*, K. Van Dyke and R. Van Dyke, eds., CRC Press, Boca Raton, pp. 11-25.

[8] T. Nieman (1995). Chemiluminescence: Theory and Instrumentation, Overview, in *Encyclopedia of Analytical Science*, Academic Press, Orlando, pp. 608-613.

[9] J. R. Lakowicz (1999). Principles of Fluorescence Spectroscopy, Kluwer, New York.

[10] K. Aslan, I. Gryczynski, J. Malicka, E. Matveeva, J. R. Lakowicz, C. D. Geddes (2005). Metal-enhanced fluorescence: an emerging tool in biotechnology. *Current Opinion in Biotechnology.* 16(1), 55-62.

[11] K. Aslan, J. R. Lakowicz, C. D. Geddes (2005). Plasmon Light Scattering in Biology and Medicine: New Sensing Approaches, Visions and Perspectives, *Current Opinions in Chemical Biology: Analytical Techniques,* 9, 538-544.

[12] C. D. Geddes, K. Aslan, I. Gryczynski, J. Malicka, J. R. Lakowicz (2005). Radiative Decay Engineering, Review Chapter for Topics in Fluorescence Spectroscopy, Eds. C. D. Geddes and J. R. Lakowicz, Kluwer Academic/Plenum Publishers, New York, USA, pp. 405-448.

[13] C. D. Geddes, K. Aslan, I. Gryczynski, J. Malicka, E. Matveeva, J. R. Lakowicz (2005). In Topics in Fluorescence in Fluorescence Spectroscopy, C. D. Geddes, J. R. Lakowicz, Eds; Kluwer Academic/Plenum Publishers, New York, USA; pp. 401-448.

[14] J. R. Lakowicz, I. Gryczynski, J. Malicka, Z. Gryczynski, C. D. Geddes (2002) Enhanced and localized multiphoton excited fluorescence near metallic silver islands: metallic islands can increase probe photostability *J. Fluoresc.,* 12, 299-302.

[15] C. D. Geddes, H. Cao, I. Gryczynski, Z. Gryczynski, J. Fang, and J. R. Lakowicz (2003). Metal-enhanced fluorescence due to silver colloids on a planar surface: Potential applications of Indocyanine green to in vivo imaging. *J. Phys. Chem. A.* 107, 3443-3449.

[16] K. Aslan, J. R. Lakowicz, C. D. Geddes (2005). Rapid deposition of triangular silver nanoplates on planar surfaces: Application to metalenhanced fluorescence. *J. Phys. Chem. B.* 109, 6247-6251.

[17] K. Aslan, Z. Leonenko, J. R. Lakowicz, C. D. Geddes (2005). Fast and slow deposition of silver nanorods on planar surfaces: Application to metalenhanced fluorescence *J. Phys. Chem. B.* 109(8), 3157-3162.

[18] C. D. Geddes, A. Parfenov, D. Roll, J. Fang, and J. R. Lakowicz (2003). Electrochemical and laser deposition of silver for use in metal enhanced fluorescence. *Langmuir* 19, 6236-6241.

[19] K. Aslan, R. Badugu, J. R. Lakowicz, C. D. Geddes (2005). Metal-enhanced fluorescence from plastic substrates. *J. Fluoresc.*, 15(2), 99-104.

[20] K. Aslan, C. D. Geddes. Microwave-Accelerated Metal-Enhanced Fluorescence (MAMEF): A New Platform Technology for Ultra Fast and Ultra Bright Assays. *Anal. Chem.* 77(24), 8057-8067.

[21] J. R. Lakowicz (2001). Radiative decay engineering: Biophysical and biomedical applications. *Anal. Biochem.* 298, 1-24.

[22] J. R. Lakowicz, C. D. Geddes, I. Gryczynski, J. Malicka, Z. Gryczynski, K. Aslan, J. Lukomska, E. Matveeva, J. Zhang, R. Badugu, J. Huang (2004). Advances in surface-enhanced fluorescence, *J. Fluoresc.*, 14(4), 425-441.

[23] K. Aslan, Z. Leonenko, J. R. Lakowicz, C. D. Geddes (2005). Annealed Silver-Island Films for Applications in Metal-Enhanced Fluorescence: Interpretation in Terms of Radiating Plasmons, *J. of Fluores.*, 15(5), 643-654.

[24] I. Gryczynski, J. Malicka, Z. Gryczynski, J. R. Lakowicz, (2004). Radiative Decay Engineering 4. Experimental studies of surface plasmon-coupled directional emission. *Anal. Biochem.*, 324, 170-182.

[25] C. D. Geddes, I. Gryczynski, J. Malicka, Z. Gryczynski, J. R. Lakowicz (2004). Directional surface plasmon coupled emission, *J. Fluoresc.*, 14, 119-123.

[26] J. Yguerabide; W Yguerabide; (1998) *Anal Biochem.* 262, 137-176.

[27] L. Rivas, S. Sanchez-Cortes, J. V. Garcia-Ramos and G. Morcillo G., (2001) Growth of Silver Colloidal Particles Obtained by Citrate Reduction to Increase the Ramen Enhancement Factor, *Langmuir*, 17(3), 574-577.

[28] N. Shirtcliffe, U. Nickel and S. Schneider, (1999) Reproducible preparation of silver sols with small particle size using borohydride reduction: For use as nuclei for preparation of large particles, *J. Colloid Interface Sci.*, 211(1), 122-129.

[29] I. Pastoriza-Santos, and L. M> Liz-Marzan, (2000) Reduction of silver nanoparticles in DMF. Formation of monolayers and stable colloids, *Pure Appl. Chem.*, 72(1-2), 83-90 (2000).

[30] Pastoriza-Santos, C. Serra-Rodriquez and L. M. Liz-Marzan, (2000) Self-assembly of silver particle monolayers on glass from Ag.sup.+ solutions in DMF, *J. Colloid Interface Sci.*, 221(2), 236-241.

[31] R. Bright, M. D. Musick. and MJ. Natan, (1998) Preparation and characterization of Ag colloid monolayers, *Langmuir*, 14(20), 5695-5701.

[32] F. Ni and T. M., (1986) Chemical procedure for preparing surface-enhanced Raman scattering active silver films, *Anal. Chem.*, 58(14), 3159-5163.

[33] U. Krelbig, M. Gartz and A. Hilger, (1997) Mie resonances: Sensors for physical and chemical cluster interface properties, Ber. Bunsenges, *Phys. Chem.*, 101(11), 1593-1604.

[34] R. G. Freeman, K. C. Grabar, K. J. Allison, R. M. Bright R., J. A. Davis, A. P. Guthrie, M. B. Hommer, M. A. Jackson, P. C. Smith, D. G Walter and M. J. Natan, (1995) Self-assembled metal colloid monolayers: An approach to SERS substrates, *Science*, 267, 1629-1632.

[35] K. C. Grabar, R. G Freeman, M. B. Hommer and M. J. Natan, (1995) Preparation and characterization of Au colloid monolayers, *Anal. Chem.*, 67, 735-743.

[36] Lakowicz, J. R. *Anal. Biochem.* 2004, 324, 153-169.

[37] Aslan, K.; Perez-Luna, V. H. *Langmuir* 2002, 18, 6059-6065.

[38] Cormier, M. J.; Prichard, P. M. *J Biol. Chem.* 1968, 243, 4706-4714.

[39] Methods in Enzymology, Vol. VLII, A. Deluca 1978.

[40] Previte, M. J. R.; Aslan, K.; Malyn, S.; Geddes, C. D. *J. Fluoresc.* 2006, 16, 641-647.

[41] Previte, M. J. R.; Aslan, K.; Malyn, S.; Geddes, C. D. *Anal. Chem.* 2006, 78, 8020-8027.

[42] Catherall, C. L. R.; Palmer, T. F.; Cundall, R. B. *J. Chem. Soc., Faraday Trans. I* 1984, 80, 823-836.

[43] Akins, R. E.; Tuan, R. S. *Mol. Biotechnol.* 1995, 4, 17-24.

[44] Aslan, K.; Malyn, S. N.; Geddes, C. D. *J. Am. Chem. Soc.* 2006, 128, 13372-13373.

[45] Iwabuchi, K.; Kubota, T.; Kashiwa, T. *Journal of Microwave Power and Electromagnetic Energy* 1996, 31, 188-196.

[46] Radzevicius, S. J.; Chen, C. C.; Peters, L.; Daniels, J. J. *Journal of Applied Geophysics* 2003, 52, 75-91.

[47] Filevich, O.; Etchenique, R. *Anal. Chem.* 2006, 78, 7499-7503.

[48] Wilchek, M.; Bayer, E. A. *Anal. Biochem.* 1988, 171, 1-32.

[49] Wilchek, M.; Bayer, E. A. *Methods Enzymol.* 1990, 184, 14-45.

[50] Aslan, K.; Geddes, C. D. *J. Fluoresc.* 2006, 16, 3-8.

[51] Chen, L. M.; Liang, Y.; Tai, J. H.; Chern, Y. J. *Biotechniques* 1994, 16, 600-601.

That which is claimed is:

1. A reactive zone system for placement and containment of a molecule, cells, pathogens, bugs, or bacteria in a sample comprising:

a non-metallic substrate surface comprising at least two immobilized metallic structures, wherein each metallic structure is shaped as a triangle, wherein an apex of each of the two triangles is arranged in alignment and opposite from each and adjacent to a formed reactive zone surface on the non-metallic substrate surface between the apexes, wherein the formed reactive zone positioned on the non-metallic substrate surface is of sufficient size for placement and containment of molecules, cells, pathogens, bugs, nucleic acid or bacteria and has a diameter of about 1 mm to about 5 mm, wherein the at least two immobilized metallic structures are fabricated from silver, gold, copper, platinum, aluminum or combinations thereof and exhibit surface plasmons upon excitation, and wherein the at least two immobilized metallic structures are positioned in an assay well.

2. The reactive zone system of claim 1 wherein the at least two immobilized metallic structures and the formed reactive zone are used for detecting fluorescence, phosphorescence, or chemiluminescence in an assay.

3. The reactive zone system of claim 2, wherein the at least two immobilized metallic structures and the formed reactive zone are used to modify, perturb or mutate any of the physical, chemical or molecular integrity of the molecules, cells, pathogens, bugs, or bacteria.

4. A reactive zone system comprising:

a non-metallic substrate surface comprising at least two immobilized metallic structures, wherein each metallic structure is shaped as a triangle, wherein an apex of each of the two triangles is arranged in alignment and opposite from each and adjacent to a reactive zone formed between the apexes, wherein the reactive zone has sufficient size for placement and containment of molecules, cells, pathogens, bugs, nucleic acid or bacteria and has a diameter of about 0.05 mm to about 5 mm, wherein the non-metallic substrate surface is glass, polymeric, paper or combination thereof, wherein the at least two immobilized metallic structures are fabricated from silver, gold, copper, platinum, aluminum or combinations thereof and exhibit surface plasmons upon excitation, and wherein the at least two immobilized metallic structures are positioned in an assay well.

* * * * *